United States Patent [19]

Albertsen et al.

[11] Patent Number: 5,691,454
[45] Date of Patent: Nov. 25, 1997

[54] APC ANTIBODIES

[75] Inventors: Hans Albertsen, Salt Lake City, Utah; Rakesh Anand, Sandbach, England; Mary Carlson; Joanna Groden, both of Salt Lake City, Utah; Philip John Hedge, Winsford, England; Geoff Joslyn, Salt Lake City, Utah; Kenneth Kinzler, Baltimore, Md.; Alexander Fred Markham, Crewe, England; Yusuke Nakamura, Tokyo, Japan; Andrew Thliveris, Salt Lake City, Utah; Bert Vogelstein, Baltimore, Md.; Raymond L. White, Salt Lake City, Utah

[73] Assignees: The Johns Hopkins University, Baltimore, Md.; University of Utah, Salt Lake City, Utah; the Cancer Institute, London, England; Imperial Chemical Industries PLC, Tokyo, Japan

[21] Appl. No.: 452,654

[22] Filed: May 25, 1995

Related U.S. Application Data

[62] Division of Ser. No. 289,548, Aug. 12, 1994, which is a division of Ser. No. 741,940, Aug. 8, 1991, Pat. No. 5,352,775.

[30] Foreign Application Priority Data

| Jan. 16, 1991 | [GB] | United Kingdom | 9100962 |
| Jan. 16, 1991 | [GB] | United Kingdom | 9100963 |
| Jan. 16, 1991 | [GB] | United Kingdom | 9100974 |
| Jan. 16, 1991 | [GB] | United Kingdom | 9100975 |

[51] Int. Cl.$^6$ .................... C07K 16/32; C12N 5/12; C12N 15/12
[52] U.S. Cl. ............... 530/387.7; 530/387.9; 530/388.8; 530/389.7; 536/23.5
[58] Field of Search .............. 530/387.1, 387.7, 530/387.9, 388.8, 389.7; 424/130.1, 138.1, 141.1, 174.1; 435/240.27; 536/23.5

[56] References Cited

U.S. PATENT DOCUMENTS 5,098,823  3/1992  Bodmer et al. .
5,137,806  8/1992  LeMaistre et al. .
5,244,801  9/1993  Tobi .

FOREIGN PATENT DOCUMENTS

WO 89/01481  8/1988  WIPO .

OTHER PUBLICATIONS

Kinzler et al, Science 253: 661–665, 1991.

Groden, et al., "Identification and Characterization of the Familial Adenomatous Polyposis Coli Gene", *Cell*, 66:589–600 (1991).

Joslyn, et al., "Identification of Deletion Mutations and Three New Genes at the Familial Polyposis Locus", *Cell*, 66:601–613 (1991).

Kinzler, et al., "Identification of FAP Locus Genes From Chromsome 5q21", *Science*, 253:661–665 (1991).

Nishisho, et al., "Mutations of Chromosome 5q21 Genes in FAP and Colorectal Cancer Patients", *Science*, 253:665–669 (1991).

Orita, et al., Genomics, vol. 5, pp. 874–879, 1989.

Stanbridge, et al., "Identifying Tumor Suppressor Genes in Human Colorectal Cancer", *Science*, 247:12–13 (1990).

Fearon et al., "Identification of a Chromosome 18q Gene That is Altered in Colorectal Cancer", *Science*, 247:49–56 (1990).

Baker et al., "Chromosome 17 Deletions and p53 Gene Mutations in Colorectal Carcinomas", *Science*, 244:217–221 (1989).

Bodmer et al., "Localization of the Gene for Familial Adenomatous Polyposis on Chromosome 5", *Nature*, 328:614–616 (1987).

*Primary Examiner*—Lila Feisee
*Assistant Examiner*—Nancy A. Johnson
*Attorney, Agent, or Firm*—Banner & Witcoff, Ltd.

[57] ABSTRACT

A human gene termed APC is disclosed. Methods and kits are provided for assessing mutations of the APC gene in human tissues and body samples. APC mutations are found in familial adenomatous polyposis patients as well as in sporadic colorectal cancer patients. APC is expressed in most normal tissues. These results suggest that APC is a tumor suppressor.

8 Claims, 40 Drawing Sheets

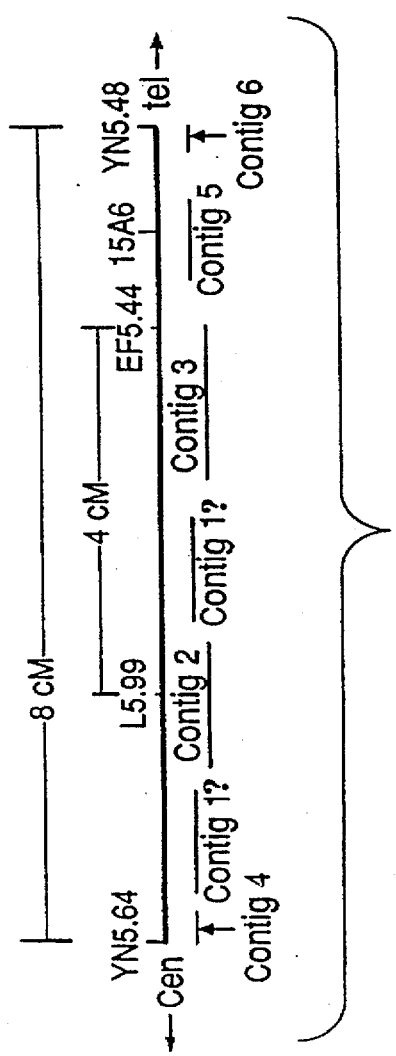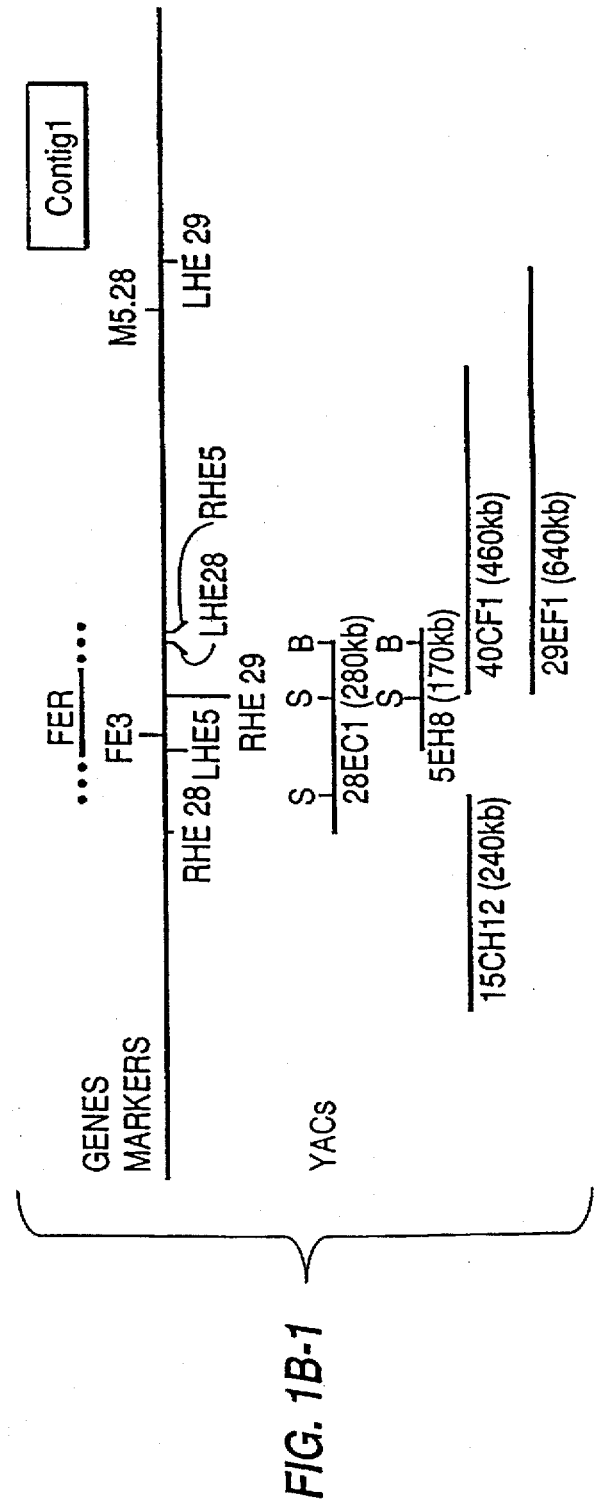
FIG. 1A
FIG. 1B-1

FIG. 2A

TB1 Amino Acid Sequence

```
VAPVVVGSGR APRHPAPAAM HPRRPDGFDG LGYRGGARDE QGFGGAFPAR SFSTGSDLGH   60
WVTTPPDIPG SRNLHWGEKS PPYGVPTTST PYEGPTEEPF SSGGGGSVQG QSSEQLNRFA  120
GFGIGLASLF TENVLAHPCI VLRRQCQVNY HAQHYHLTPF TVINIMYSFN KTQGPRALWK  180
GMGSTFIVQG VTLGAEGIIS EFTPLPREVL HKWSPKQIGE HLLLKSLTYV VAMPFYSASL  240
IETVQSEIIR DNTGILECVK EGIGRVIGMG VPHSKRLLPL LSLIFPTVLH GVLHYIISSV  300
IQKFVLLILK RKTYNSHLAE STSPVQSMLD AYFPELIANF AASLCSDVIL YPLETVLHRL  360
HIQGIRTIID NTDLGYEVLP INTQYEGMRD CINTIRQEEG VFGFYKGFGA VIIQYTLHAA  420
VLQITKIIYS TLLQ                                                   434
```

FIG. 2B

TB2 Amino Acid Sequence

```
ELRRFDRFLH EKNCMTDLLA KLEAKTGVNR SFIALGVIGL VALYLVFGYG ASLLCNLIGF    60
GYPAYISIKA IESPNKEDDT QWLTYWVYG VFSIAEFFSD IFLSWFPFYY ILKCGFLLWC   120
MAPSPSNGAE LLYKRIIRPF FLKHESQMDS VVKDLKQKAK ETADAITKEA KKATVNLLGE  180
EKKST                                                             185
```

FIG. 3A

```
Met Ala Ala Ala Ser Tyr Asp Gln Leu Leu Lys Gln Val Glu Ala Leu
 1               5                  10                  15
Lys Met Glu Asn Ser Asn Leu Arg Gln Glu Leu Glu Asp Asn Ser Asn
            20                  25                  30
His Leu Thr Lys Leu Glu Thr Glu Ala Ser Asn Met Lys Glu Val Leu
        35                  40                  45
Lys Gln Leu Gln Gly Ser Ile Glu Asp Glu Ala Met Ala Ser Ser Gly
        50                  55                  60
Gln Ile Asp Leu Leu Glu Arg Leu Lys Glu Leu Asn Leu Asp Ser Ser
    65                  70                  75              80
Asn Phe Pro Gly Val Lys Leu Arg Ser Lys Met Ser Leu Arg Ser Tyr
            85                  90                  95
Gly Ser Arg Glu Gly Gly Ser Val Ser Ser Arg Ser Gly Glu Cys Ser Pro
            100                 105                 110
```

FIG. 3B

```
Val Pro Met Gly Ser Phe Pro Arg Arg Gly Phe Val Asn Gly Ser Arg
        115                 120                 125

Glu Ser Thr Gly Tyr Leu Glu Leu Glu Lys Glu Arg Ser Leu Leu
        130                 135                 140

Leu Ala Asp Leu Asp Lys Glu Glu Lys Glu Lys Asp Trp Tyr Tyr Ala
        145                 150                 155                 160

Gln Leu Gln Asn Leu Thr Lys Arg Ile Asp Ser Leu Pro Leu Thr Glu
        165                 170                 175

Asn Phe Ser Leu Gln Thr Asp Leu Thr Arg Arg Gln Leu Glu Tyr Glu
        180                 185                 190

Ala Arg Gln Ile Arg Val Ala Met Glu Gln Leu Gly Thr Cys Gln
        195                 200                 205

Asp Met Glu Lys Arg Ala Gln Arg Arg Ile Ala Arg Ile Gln Gln Ile
        210                 215                 220
```

FIG. 3C

Glu Lys Asp Ile Leu Arg Ile Arg Gln Leu Leu Gln Ser Gln Ala Thr
225                     230                    235                    240

Glu Ala Glu Arg Ser Ser Gln Asn Lys His Glu Thr Gly Ser His Asp
            245                    250                    255

Ala Glu Arg Gln Asn Glu Gly Gln Gly Val Gly Glu Ile Asn Met Ala
                260                    265                    270

Thr Ser Gly Asn Gly Gln Gly Ser Thr Thr Arg Met Asp His Glu Thr
        275                    280                    285

Ala Ser Val Leu Ser Ser Ser Ser Thr His Ser Ala Pro Arg Arg Leu
            290                    295                    300

Thr Ser His Leu Gly Thr Lys Val Glu Met Val Tyr Ser Leu Leu Ser
        305                    310                    315                    320

Met Leu Gly Thr His Asp Lys Asp Asp Met Ser Arg Thr Leu Leu Ala
                325                    330                    335

FIG. 3D

Met Ser Ser Ser Gln Asp Ser Cys Ile Ser Met Arg Gln Ser Gly Cys
                340                 345                 350

Leu Pro Leu Leu Ile Gln Leu Leu His Gly Asn Asp Lys Asp Ser Val
            355                 360                 365

Leu Leu Gly Asn Ser Arg Gly Ser Lys Glu Ala Arg Ala Arg Ala Ser
        370                 375                 380

Ala Ala Leu His Asn Ile Ile His Ser Gln Pro Asp Asp Lys Arg Gly
    385                 390                 395                 400

Arg Arg Glu Ile Arg Val Leu His Leu Leu Glu Gln Ile Arg Ala Tyr
                405                 410                 415

Cys Glu Thr Cys Trp Glu Trp Gln Glu Ala His Glu Pro Gly Met Asp
            420                 425                 430

Gln Asp Lys Asn Pro Met Pro Ala Pro Val Glu His Gln Ile Cys Pro
        435                 440                 445

FIG. 3E

Ala Val Cys Val Leu Met Lys Leu Ser Phe Asp Glu His Arg His
450                     455                     460

Ala Met Asn Glu Leu Gly Gly Leu Gln Ala Ile Ala Glu Leu Leu Gln
465                     470                 475                 480

Val Asp Cys Glu Met Tyr Gly Leu Thr Asn Asp His Tyr Ser Ile Thr
                485                     490                 495

Leu Arg Arg Tyr Ala Gly Met Ala Leu Thr Asn Leu Thr Phe Gly Asp
            500                     505                 510

Val Ala Asn Lys Ala Thr Leu Cys Ser Met Lys Gly Cys Met Arg Ala
        515                     520                 525

Leu Val Ala Gln Leu Lys Ser Glu Ser Glu Asp Leu Gln Gln Val Ile
    530                     535                 540

Ala Ser Val Leu Arg Asn Leu Ser Trp Arg Ala Asp Val Asn Ser Lys
545                     550                 555                 560

FIG. 3F

Lys Thr Leu Arg Glu Val Gly Ser Val Lys Ala Leu Met Glu Cys Ala
565                                 570                             575

Leu Glu Val Lys Lys Glu Ser Thr Leu Lys Ser Val Leu Ser Ala Leu
580                                 585                             590

Trp Asn Leu Ser Ala His Cys Thr Glu Asn Lys Ala Asp Ile Cys Ala
595                                 600                             605

Val Asp Gly Ala Leu Ala Phe Leu Val Gly Thr Leu Thr Tyr Arg Ser
610                                 615                             620

Gln Thr Asn Thr Leu Ala Ile Ile Glu Ser Gly Gly Ile Leu Arg
625                                 630                             635                             640

Asn Val Ser Ser Leu Ile Ala Thr Asn Glu Asp His Arg Gln Ile Leu
645                                 650                             655

Arg Glu Asn Asn Cys Leu Gln Thr Leu Leu Gln His Leu Lys Ser His
660                                 665                             670

FIG. 3G

Ser Leu Thr Ile Val Ser Asn Ala Cys Gly Thr Leu Trp Asn Leu Ser
                675                 680                 685

Ala Arg Asn Pro Lys Asp Gln Glu Ala Leu Trp Asp Met Gly Ala Val
        690                 695                 700

Ser Met Leu Lys Asn Leu Ile His Ser Lys Met Ile Ala Met
705                 710                 715                 720

Gly Ser Ala Ala Leu Arg Asn Leu Met Ala Asn Arg Pro Ala Lys
            725                 730                 735

Tyr Lys Asp Ala Asn Ile Met Ser Pro Gly Ser Ser Leu Ser Leu
                740                 745                 750

His Val Arg Lys Gln Lys Ala Leu Glu Ala Leu Asp Ala Gln His
        755                 760                 765

Leu Ser Glu Thr Phe Asp Asn Ile Asp Asn Leu Ser Pro Lys Ala Ser
            770                 775                 780

FIG. 3H

His Arg Ser Lys Gln Arg His Lys Gln Ser Leu Tyr Gly Asp Tyr Val
785                     790                 795                 800

Phe Asp Thr Asn Arg His Asp Asn Arg Ser Asp Asn Phe Asn Thr
        805                 810                 815

Gly Asn Met Thr Val Leu Ser Pro Tyr Leu Asn Thr Thr Val Leu Pro
820                     825                 830

Ser Ser Ser Ser Arg Gly Ser Leu Asp Ser Ser Arg Ser Glu Lys
        835                 840                 845

Asp Arg Ser Leu Glu Arg Glu Arg Gly Ile Gly Leu Gly Asn Tyr His
850                     855                 860

Pro Ala Thr Glu Asn Pro Gly Thr Ser Ser Lys Arg Gly Leu Gln Ile
865                     870                 875                 880

Ser Thr Thr Ala Ala Gln Ile Ala Lys Val Met Glu Glu Val Ser Ala
        885                 890                 895

FIG. 3I

Ile His Thr Ser Gln Glu Asp Arg Ser Ser Gly Ser Thr Thr Glu Leu
                900                 905                 910

His Cys Val Thr Asp Glu Arg Asn Ala Leu Arg Arg Ser Ala Ala
            915                 920                 925

His Thr His Ser Asn Thr Tyr Asn Phe Thr Lys Ser Glu Asn Ser Asn
                930                 935                 940

Arg Thr Cys Ser Met Pro Tyr Ala Lys Leu Glu Tyr Lys Arg Ser Ser
                945                 950                 955                 960

Asn Asp Ser Leu Asn Ser Val Ser Ser Asn Asp Gly Tyr Gly Lys Arg
                965                 970                 975

Gly Gln Met Lys Pro Ser Ile Glu Ser Tyr Ser Glu Asp Asp Glu Ser
                980                 985                 990

Lys Phe Cys Ser Tyr Gly Gln Tyr Pro Ala Asp Leu Ala His Lys Ile
                995                 1000                 1005

FIG. 3J

His Ser Ala Asn His Met Asp Asn Asp Gly Glu Leu Asp Thr Pro
1010                          1015                     1020

Ile Asn Tyr Ser Leu Lys Tyr Ser Asp Glu Gln Leu Asn Ser Gly Arg
1025                      1030                    1035           1040

Gln Ser Pro Ser Gln Asn Glu Arg Trp Ala Arg Pro Lys His Ile Ile
           1045                      1050                     1055

Glu Asp Glu Ile Lys Gln Ser Glu Gln Arg Gln Ser Arg Asn Gln Ser
                1060                      1065                 1070

Thr Thr Tyr Pro Val Tyr Thr Glu Ser Thr Asp Asp Lys His Leu Lys
           1075                      1080                  1085

Phe Gln Pro His Phe Gly Gln Gln Glu Cys Val Ser Pro Tyr Arg Ser
                1090                      1095              1100

Arg Gly Ala Asn Gly Ser Glu Thr Asn Arg Val Gly Ser Asn His Gly
           1105                      1110                  1115           1120

FIG. 3K

Ile Asn Gln Asn Val Ser Gln Ser Leu Cys Gln Glu Asp Asp Tyr Glu
                1125                    1130                   1135

Asp Asp Lys Pro Thr Asn Tyr Ser Glu Arg Tyr Ser Glu Glu Gln
        1140                    1145                   1150

His Glu Glu Arg Pro Thr Asn Tyr Ser Ile Lys Tyr Asn Glu
        1155                    1160               1165

Glu Lys Arg His Val Asp Gln Pro Ile Asp Tyr Ser Leu Lys Tyr Ala
        1170                    1175                   1180

Thr Asp Ile Pro Ser Ser Gln Lys Gln Ser Phe Ser Lys Ser
        1185                    1190           1195        1200

Ser Ser Gly Gln Ser Ser Lys Thr Glu His Met Ser Ser Ser Ser Glu
                1205                    1210                   1215

Asn Thr Ser Thr Pro Ser Ser Asn Ala Lys Arg Gln Asn Gln Leu His
        1220                    1225                   1230

FIG. 3L

Pro Ser Ser Ala Gln Ser Arg Ser Gly Gln Pro Gln Lys Ala Ala Thr
1235                          1240                      1245

Cys Lys Val Ser Ser Ile Asn Gln Glu Thr Ile Gln Thr Tyr Cys Val
         1250                      1255                      1260

Glu Asp Thr Pro Ile Cys Phe Ser Arg Cys Ser Ser Leu Ser Ser Leu
1265                          1270                      1275                 1280

Ser Ser Ala Glu Asp Glu Ile Gly Cys Asn Gln Thr Thr Gln Glu Ala
         1285                      1290                      1295

Asp Ser Ala Asn Thr Leu Gln Ile Ala Glu Ile Lys Gly Lys Ile Gly
1300                          1305                      1310

Thr Arg Ser Ala Glu Asp Pro Val Ser Glu Val Pro Ala Val Ser Gln
         1315                      1320                      1325

His Pro Arg Thr Lys Ser Ser Arg Leu Gln Gly Ser Ser Leu Ser Ser
1330                          1335                      1340

FIG. 3M

Glu Ser Ala Arg His Lys Ala Val Glu Phe Pro Ser Gly Ala Lys Ser
1345                          1350                          1355                     1360

Pro Ser Lys Ser Gly Ala Gln Thr Pro Lys Ser Pro Pro Glu His Tyr
1365                          1370                          1375

Val Gln Glu Thr Pro Leu Met Phe Ser Arg Cys Thr Ser Val Ser Ser
1380                          1385                          1390

Leu Asp Ser Phe Glu Ser Arg Ser Ile Ala Ser Ser Val Gln Ser Glu
1395                          1400                          1405

Pro Cys Ser Gly Met Val Ser Gly Ile Ile Ser Pro Ser Asp Leu Pro
1410                          1415                          1420

Asp Ser Pro Gly Gln Thr Met Pro Pro Ser Arg Ser Lys Thr Pro Pro
1425                          1430                          1435                     1440

Pro Pro Pro Gln Thr Ala Gln Thr Lys Arg Glu Val Pro Lys Asn Lys
1445                          1450                          1455

FIG. 3N

Ala Pro Thr Ala Glu Lys Arg Glu Ser Gly Pro Lys Gln Ala Ala Val
1460                          1465                         1470

Asn Ala Ala Val Gln Arg Val Gln Val Leu Pro Asp Ala Asp Thr Leu
           1475                          1480                    1485

Leu His Phe Ala Thr Glu Ser Thr Pro Asp Gly Phe Ser Cys Ser Ser
     1490                          1495                    1500

Ser Leu Ser Ala Leu Ser Leu Asp Glu Pro Phe Ile Gln Lys Asp Val
1505                          1510                    1515       1520

Glu Leu Arg Ile Met Pro Pro Val Gln Glu Asn Asp Asn Gly Asn Glu
           1525                          1530                1535

Thr Glu Ser Glu Gln Pro Lys Glu Ser Asn Glu Asn Gln Glu Lys Glu
     1540                          1545                    1550

Ala Glu Lys Thr Ile Asp Ser Glu Lys Asp Leu Leu Asp Asp Ser Asp
1555                          1560                    1565

FIG. 30

Asp Asp Ile Glu Ile Leu Glu Glu Cys Ile Ile Ser Ala Met Pro
1570                          1575                    1580

Thr Lys Ser Ser Arg Lys Gly Lys Lys Pro Ala Gln Thr Ala Ser Lys
1585                    1590                    1595                    1600

Leu Pro Pro Val Ala Arg Lys Pro Ser Gln Leu Pro Val Tyr Lys
     1605                         1610                    1615

Leu Leu Pro Ser Gln Asn Arg Leu Gln Pro Gln Lys His Val Ser Phe
     1620                    1625                    1630

Thr Pro Gly Asp Asp Met Pro Arg Val Tyr Cys Val Glu Gly Thr Pro
1635                    1640                    1645

Ile Asn Phe Ser Thr Ala Thr Ser Leu Ser Asp Leu Thr Ile Glu Ser
1650                    1655                    1660

Pro Pro Asn Glu Leu Ala Ala Gly Glu Gly Val Arg Gly Gly Ala Gln
1665                    1670                    1675                    1680

FIG. 3P

Ser Gly Glu Phe Glu Lys Arg Asp Thr Ile Pro Thr Glu Gly Arg Ser
1685                               1690                              1695

Thr Asp Glu Ala Gln Gly Gly Lys Thr Ser Ser Val Thr Ile Pro Glu
1700                               1705                              1710

Leu Asp Asn Lys Ala Glu Gly Asp Ile Leu Ala Glu Cys Ile
         1715                           1720                     1725

Asn Ser Ala Met Pro Lys Gly Lys Ser His Lys Pro Phe Arg Val Lys
1730                               1735                              1740

Lys Ile Met Asp Gln Val Gln Gln Ala Ser Ala Ser Ser Ser Ala Pro
1745                               1750                    1755                  1760

Asn Lys Asn Gln Leu Asp Gly Lys Lys Lys Lys Pro Thr Ser Pro Val
                  1765                          1770                       1775

Lys Pro Ile Pro Gln Asn Thr Glu Tyr Arg Thr Arg Val Arg Lys Asn
1780                               1785                              1790

FIG. 3Q

Ala Asp Ser Lys Asn Asn Leu Asn Ala Glu Arg Val Phe Ser Asp Asn
1795                          1800                        1805

Lys Asp Ser Lys Lys Gln Asn Leu Lys Asn Asn Ser Lys Asp Phe Asn
1810                          1815                        1820

Asp Lys Leu Pro Asn Asn Glu Asp Arg Val Arg Gly Ser Phe Ala Phe
1825                          1830                        1835                1840

Asp Ser Pro His His Tyr Thr Pro Ile Glu Gly Thr Pro Tyr Cys Phe
1845                          1850                        1855

Ser Arg Asn Asp Ser Leu Ser Ser Leu Asp Phe Asp Asp Asp Asp Val
1860                          1865                        1870

Asp Leu Ser Arg Glu Lys Ala Glu Leu Arg Lys Ala Lys Glu Asn Lys
1875                          1880                        1885

Glu Ser Glu Ala Lys Val Thr Ser His Thr Glu Leu Thr Ser Asn Gln
1890                          1895                        1900

FIG. 3R

```
Gln Ser Ala Asn Lys Thr Gln Ala Ile Ala Lys Gln Pro Ile Asn Arg
1905                     1910                    1915                    1920
Gly Gln Pro Lys Pro Ile Leu Gln Lys Gln Ser Thr Phe Pro Gln Ser
1925                     1930                    1935
Ser Lys Asp Ile Pro Asp Arg Gly Ala Ala Thr Asp Glu Lys Leu Gln
1940                     1945                    1950
Asn Phe Ala Ile Glu Asn Thr Pro Val Cys Phe Ser His Asn Ser Ser
1955                     1960                    1965
Leu Ser Ser Leu Ser Asp Ile Asp Gln Glu Asn Asn Asn Lys Glu Asn
1970                     1975                    1980
Glu Pro Ile Lys Glu Thr Glu Pro Pro Asp Ser Gln Gly Glu Pro Ser
1985                     1990                    1995                    2000
Lys Pro Gln Ala Ser Gly Tyr Ala Pro Lys Ser Phe His Val Glu Asp
2005                     2010                    2015
```

FIG. 3S

Thr Pro Val Cys Phe Ser Arg Asn Ser Ser Leu Ser Ile
2020                         2025              2030

Asp Ser Glu Asp Asp Leu Leu Gln Glu Cys Ile Ser Ser Ala Met Pro
2035                         2040                    2045

Lys Lys Lys Pro Ser Arg Leu Lys Gly Asp Asn Glu Lys His Ser
2050                    2055                    2060

Pro Arg Asn Met Gly Gly Ile Leu Gly Glu Asp Leu Thr Leu Asp Leu
2065                    2070                    2075              2080

Lys Asp Ile Gln Arg Pro Asp Ser Glu His Gly Leu Ser Pro Asp Ser
2085                         2090                    2095

Glu Asn Phe Asp Trp Lys Ala Ile Gln Glu Gly Ala Asn Ser Ile Val
2100                         2105                    2110

Ser Ser Leu His Gln Ala Ala Ala Ala Cys Leu Ser Arg Gln Ala
2115              2120                        2125

FIG. 3T

Ser Ser Asp Ser Asp Ser Ile Leu Ser Leu Lys Ser Gly Ile Ser Leu
2130                                        2140

Gly Ser Pro Phe His Leu Thr Pro Asp Gln Glu Lys Pro Phe Thr
2145                                   2155                          2160

Ser Asn Lys Gly Pro Arg Ile Leu Lys Pro Gly Glu Lys Ser Thr Leu
2165                                        2170                          2175

Glu Thr Lys Lys Ile Glu Ser Glu Ser Lys Gly Ile Lys Gly Gly Lys
2180                                   2185                          2190

Lys Val Tyr Lys Ser Leu Ile Thr Gly Lys Val Arg Ser Asn Ser Glu
2195                                   2200                          2205

Ile Ser Gly Gln Met Lys Gln Pro Leu Gln Ala Asn Met Pro Ser Ile
2210                                   2215                          2220

Ser Arg Gly Arg Thr Met Ile His Ile Pro Gly Val Arg Asn Ser Ser
2225                                   2230                          2235                          2240

FIG. 3U

Ser Ser Thr Ser Pro Val Ser Lys Lys Gly Pro Pro Leu Lys Thr Pro
                    2245                2250                2255

Ala Ser Lys Ser Pro Ser Glu Gly Gln Thr Ala Thr Thr Ser Pro Arg
                2260                2265                2270

Gly Ala Lys Pro Ser Val Lys Ser Glu Leu Ser Pro Val Ala Arg Gln
            2275                2280                2285

Thr Ser Gln Ile Gly Gly Ser Ser Lys Ala Pro Ser Arg Ser Gly Ser
        2290                2295                2300

Arg Asp Ser Thr Pro Ser Arg Pro Ala Gln Gln Pro Leu Ser Arg Pro
    2305                2310                2315                2320

Ile Gln Ser Pro Gly Arg Asn Ser Ile Ser Pro Gly Arg Asn Gly Ile
                2325                2330                2335

Ser Pro Pro Asn Lys Leu Ser Gln Leu Pro Arg Thr Ser Ser Pro Ser
            2340                2345                2350

FIG. 3V

Thr Ala Ser Thr Lys Ser Ser Gly Ser Gly Lys Met Ser Tyr Thr Ser
2355                          2360                      2365

Pro Gly Arg Gln Met Ser Gln Asn Leu Thr Lys Gln Thr Gly Leu
2370                      2375                      2380

Ser Lys Asn Ala Ser Ser Ile Pro Arg Ser Glu Ser Ala Ser Lys Gly
2385                          2390                      2395                      2400

Leu Asn Gln Met Asn Asn Gly Ala Asn Lys Lys Val Glu Leu
2405                      2410                      2415

Ser Arg Met Ser Ser Thr Lys Ser Ser Gly Ser Glu Ser Asp Arg Ser
2420                          2425                      2430

Glu Arg Pro Val Leu Val Arg Gln Ser Thr Phe Ile Lys Glu Ala Pro
2435                          2440                      2445

Ser Pro Thr Leu Arg Arg Lys Leu Glu Glu Ser Ala Ser Phe Glu Ser
2450                          2455                      2460

FIG. 3W

Leu Ser Pro Ser Ser Ser Arg Pro Ala Ser Pro Thr Arg Ser Gln Ala Gln
2465                          2470                         2475                        2480

Thr Pro Val Leu Ser Pro Ser Leu Pro Asp Met Ser Leu Ser Thr His
       2485                         2490                        2495

Ser Ser Val Gln Ala Gly Gly Trp Arg Lys Leu Pro Pro Asn Leu Ser
             2500                        2505                         2510

Pro Thr Ile Glu Tyr Asn Asp Gly Arg Pro Ala Lys Arg His Asp Ile
            2515                         2520                         2525

Ala Arg Ser His Ser Glu Ser Pro Ser Arg Leu Pro Ile Asn Arg Ser
            2530                         2535                        2540

Gly Thr Trp Lys Arg Glu His Ser Lys His Ser Ser Ser Leu Pro Arg
           2545                         2550                        2555                        2560

Val Ser Thr Trp Arg Arg Thr Gly Ser Ser Ser Ser Ile Leu Ser Ala
           2565                         2570                        2575

FIG. 3X

Ser Ser Glu Ser Ser Ser Glu Lys Ala Lys Ser Glu Asp Glu Lys His Val
2580                2585                    2590

Asn Ser Ile Ser Gly Thr Lys Gln Ser Lys Glu Asn Gln Val Ser Ala
2595                2600                2605

Lys Gly Thr Trp Arg Lys Ile Lys Glu Asn Glu Phe Ser Pro Thr Asn
2610                2615                2620

Ser Thr Ser Gln Thr Val Ser Ser Gly Ala Thr Asn Gly Ala Glu Ser
2625                2630                2635                2640

Lys Thr Leu Ile Tyr Gln Met Ala Pro Ala Val Ser Lys Thr Glu Asp
2645                2650                2655

Val Trp Val Arg Ile Glu Asp Cys Pro Ile Asn Asn Pro Arg Ser Gly
2660                2665                2670

Arg Ser Pro Thr Gly Asn Thr Pro Pro Val Ile Asp Ser Val Ser Glu
2675                2680                2685

FIG. 3Y

Lys Ala Asn Pro Asn Ile Lys Asp Ser Lys Asp Asn Gln Ala Lys Gln
2690                                           2700

Asn Val Gly Asn Gly Ser Val Pro Met Arg Thr Val Gly Leu Glu Asn
2705                              2715                       2720

Arg Leu Thr Ser Phe Ile Gln Val Asp Ala Pro Asp Gln Lys Gly Thr
          2725                         2730                   2735

Glu Ile Lys Pro Gly Gln Asn Asn Pro Val Pro Val Ser Glu Thr Asn
               2740                   2745                   2750

Glu Ser Pro Ile Val Glu Arg Thr Pro Phe Ser Ser Ser Ser Ser Ser
          2755                    2760                 2765

Lys His Ser Ser Pro Ser Gly Thr Val Ala Ala Arg Val Thr Pro Phe
2770                        2775                        2780

Asn Tyr Asn Pro Ser Pro Arg Lys Ser Ser Ala Asp Ser Thr Ser Ala
2785                    2790                    2795          2800

FIG. 3Z

Arg Pro Ser Gln Ile Pro Thr Pro Val Asn Asn Asn Thr Lys Lys Arg
2805                         2810                    2815

Asp Ser Lys Thr Asp Ser Ser Thr Glu Ser Ser Gly Thr Gln Ser Pro Lys
2820                         2825                    2830

Arg His Ser Gly Ser Tyr Leu Val Thr Ser Val
2835                         2840

FIG. 4A

```
APC    203  LGTCQDMEKRAQRRIARIQQIEKDILRIRQL  233
                ||  ||  |||||| ||           |
RAL2   576  LTGAKGLQLRALRRIARIEQGGTAISPTSPL  606
```

FIG. 4B

```
APC       453  MKLSFDEEHRHAMNELGGLQAIAELLQVD   481
                 |     ||:||||   ::
M3 MAChR  249  LYWRIYKETEKRTKELAGLQASGTEAETE   277
               ||  :  |  |     |||||
MCC       220  LYPNLAEERSRWEKELAGLREENESLTAM   248
                 ||: :  ||:||   |  |
APC       453  MKLSFDEEHRHAMNELGGLQAIAELLQVD   481
```

FIG. 6A

```
GCA GTC GCC GCT CCA GTC TAT CCG GCA CTA GGA ACA GCC CCG GGN GGC GAG ACG
Ala Val Ala Ala Pro Val Tyr Pro Ala Leu Gly Thr Ala Pro Gly Gly Glu Thr
 28                              55                                  109

GTC CCC GCC ATG TCT GCG GCG ATG AGG GAG TTC GAC CGG TTC CTG CAC GAG
Val Pro Ala MET Ser Ala Ala MET Arg Glu Phe Asp Arg Phe Leu His Glu
 82                             136                                 163

AAG AAC TGC ATG ACT GAC CTT CTG GCC AAG CTC GAG GCC AAA ACC GGC GTG AAC
Lys Asn Cys MET Thr Asp Leu Leu Ala Lys Leu Glu Ala Lys Thr Gly Val Asn
190                             217                                 271

AGG AGC TTC ATC GCT CTT GGT GTC GTG GCT CTG TAC CTG GTG TTC
Arg Ser Phe Ile Ala Leu Gly Val Val Ala Leu Tyr Leu Val Phe
244                             298                         325

GGT TAT GGA GCC TCT CTC CTC TGC CTG ATA GGA TTT GGA TAC CCA GCC TAC
Gly Tyr Gly Ala Ser Leu Leu Cys Leu Ile Gly Phe Gly Tyr Pro Ala Tyr
271                             325

ATC TCA ATT AAA GCT ATA GAG AGT AAC AAA GAT GAA ATT GCT GAG AGC AAA ACC CAG TGG CTG
Ile Ser Ile Lys Ala Ile Glu Ser Asn Lys Asp Glu Asp Ile Ala Glu Phe Thr Gln Trp Leu
352                             406                                 433

ACC TAC TGG GTA GTG TAT GGT GTG TTC TCC ATC GCT GAA TTC TTC TCT GAT ATC
Thr Tyr Trp Val Val Tyr Gly Val Phe Ser Ile Ala Glu Phe Phe Ser Asp Ile
379                             433

TTC CTG TCA TGG TTT CCC TTC TAC TAC ATG CTG AAG TGT GGC TTC CTG CTG TGG
Phe Leu Ser Trp Phe Pro Phe Tyr Tyr MET Leu Lys Cys Gly Phe Leu Leu Trp
406                             460                                 487

TGC ATG GCC CCG AGC CCT TCT AAT GGG GCT GAA CTG CTC TAC AAG CGC ATC ATC
Cys MET Ala Pro Ser Pro Ser Asn Gly Ala Glu Leu Leu Tyr Lys Arg Ile Ile
460                             514                                 541

CGT CCT TTC TTC CTG AAG CAC GAG TCC CAG ATG GAC AGT GTG GTC AAG GAC CTT
Arg Pro Phe Phe Leu Lys His Glu Ser Gln MET Asp Ser Val Val Lys Asp Leu
487                             541
```

FIG. 6B

```
                                    568
AAA GAC AAG TCC AAA GAG ACT GCA GAT GCC ATC ACT AAA GAA GCG AAG AAA GCT
Lys Asp Lys Ser Lys Glu Thr Ala Asp Ala Ile Thr Lys Glu Ala Lys Lys Ala
                                                                     595
                                            622
ACC GTG AAT TTA CTG GGT GAA GAA AAG AGC ACC TAA ACC AGA
Thr Val Asn Leu Leu Gly Glu Glu Lys Ser Thr
CTAAACCAGA CTGGATGGAA ACTTCCTGCC CTCTCTGTAC CTTCCTACTG GAGCTTGATG TTATATTAGG
    640        650        660        670        680        690        700
TGTCCACGTT TTTGGAAAAT GTATTTTGCC TCTGGGTAGG AAAAGATGTA TGTTGCTATC CTGCAGGAAA
    710        720        730        740        750        760        770
GACTGTGGTA TAATTATTTT AATAAATGTT CCTTGGAAAC ATTTTTGAGA TATTAAAGAT TGGAATGTGT
    780        790        800        810        820        830        840
TGTAAGTTTC TTTGCTTACT TTTACTGTCT ATATATATAG GGAGCACTTT AAACTTAAATG CAGTGGGCAG
    850        860        870        880        890        900        910
TGTCCACGTT TTTGGAAAAT GTATTTTGCC TCTGGGTAGG AAAAGATGTA TGTTGCTATC CTGCAGGAAA
    920        930        940        950        960        970        980
TATAAACTTA AAATAAAATT ATATACCCCA CAGGCTGTGT ACTTTACTGG GCTCTCCCTG CACGSATTTT
    990       1000       1010       1020       1030       1040       1050
CTCTGTAGTT ACATTTAGGR TAATCTTTAT GGTTCTACTT CCTRTAATGT ACAATTTTAT ATAATTCNGR
   1060       1070       1080       1090       1100       1110       1120
AATGTTTTTA ATGTATTTGT GCACATGTAC ATATGGAAAT GTTACTGTCT GACTACANCA TGCATCATGC
   1130       1140       1150       1160       1170       1180       1190
TCATGGGGAG GGAGCAGGGG AAGGTTGTAT GTGTCATTTA TAACTTCTGT ACAGTAAGAC CACCTGCCAA
   1200       1210       1220       1230       1240       1250       1260
AAGCTGGAGG AACCATTGTG CTGGGTGTGGT CTACTAAATA ATACTTTAGG AAATACGTGA TTAATATGCA
   1270       1280       1290       1300       1310       1320       1330
AGTGAACAAA GTGAGAAATG AAATCGAATG GAGATTGGCC TGGTTGTTTC CGTAGTATAT GGCATATGAA
   1340       1350       1360       1370       1380       1390       1400
```

FIG. 6C

```
TACCAGGATA GCTTTATAAA GCAGTTAGTT AGTTAGTTAC TCACTCTAGT GATAAATCGG GAAATTTACA
   1410       1420       1430       1440       1450       1460       1470
CACACACACA CACACACACA CACACACACA CACACACACA CACACACACA GAGTACCCTG TAACTCTCAA
   1480       1490       1500       1510       1520       1530       1540
TTCCCTGAAA AACTAGTAAT ACTGTCTTAT CTGCTATAAA CTTTACATAT TTGTCTATTG TCAAGATGCT
   1550       1560       1570       1580       1590       1600       1610
ACANTGGAMN CCATTTCTGG TTTTATCTTC ANAGSGGAGA NACATGTTGA TTTAGTCTTC TTTCCCAATC
   1620       1630       1640       1650       1660       1670       1680
TTCTTTTTA AMCCAGTTTN AGGMNCTTCT GRAGATTTGY CCACCTCTGA TTACATGTAT GTTCTYGTTT
   1690       1700       1710       1720       1730       1740       1750
GTATCATKAG CAACAACATG CTAATGRCGA CACCTAGCTC TRAGMGCAAT TCTGGGAGAN TGARAGGNWG
   1760       1770       1780       1790       1800       1810       1820
TATARAGTMN CCCATAATCT GCTTGGCAAT AGTTAAGTCA ATCTATCTTC AGTTTTTCTC TGGCCTTTAA
   1830       1840       1850       1860       1870       1880       1890
GGTCAAACAC AAGAGGCTTC CCTAGTTTAC AAGTCAGAGT CACTTGTAGT CCATTTAAAT GCCCTCATCC
   1900       1910       1920       1930       1940       1950       1960
GTATTCTTTG TGTTGATAAG CTGCACAKGA CTACATAGTA AGTACAGANC AGTAAAGTTA ANNCGGATGT
   1970       1980       1990       2000       2010       2020       2030
CTCCATTGAT CTGCQAANTC GNTATAGAGA TGGACTAGAA AATCTGAGTT TTACCATA
   2040       2050       2060       2070       2080       2090       2100
CTGTTAAGAG TCCTTTTGAA TTAAACTAGA CTAAAACAAG TGTATAACTA AACTAACAAG ATTAAATATC
   2110       2120       2130       2140       2150       2160       2170
CAGCCAGTAC AGTATTTTTT AAGGCAAATA AAGATGATTA GCTCACCTTG AGNTAACAAT CAGGTAAGAT
   2180       2190       2200       2210       2220       2230       2240
CATNACAATG TCTCATGATG TNAANAATAT TAAAGATATC AATACTAAGT GACAGTATCA CNNCTAATAT
```

FIG. 6D

```
           2250       2260       2270       2280       2290       2300       2310
     AATATGGATC AGAGCATTTA TTTGGGGGAG GAAAACAGTG GTGATTACCG GCATTTTATT AAACTTAAAA
           2320       2330       2340       2350       2360       2370       2380
     CTTGTAGAA AGCAAACAAA ATTGTTCTTG GGAGAAAATC AACTTTTAGA TTAAAAAAAT TTTAAGTAWC
           2390       2400       2410       2420       2430       2440       2450
     TAGGAGTATT TAAATCCTTT TCCCATAAAT AAAAGTACAG TTTTCTTGGT GGCAGAATGA AAATCAGCAA
           2460       2470       2480       2490       2500       2510       2520
     CNTCTAGCAT ATAGACTATA TAATCAGATT GACAGCATAT AGAATATATT ATCAGACAAG ATGAGGAGGT
           2530       2540       2550       2560       2570       2580       2590
     ACAAAAGTTA CTATTGCTCA TAATGACTTA CAGGCTAAAA NTAGNTNTAA AATACTATAT TAAATTCTGA
           2600       2610       2620       2630       2640       2650       2660
     ATGCAATTTT TTTTGTTCC CTTGAGACCA AAATTTAAGT TAACTGTTGC TGGCAGTCTA AGTGTAAATG
           2670       2680       2690       2700       2710       2720       2730
     TTAACAGCAG GAGAAGTTAA GAATTGAGCA GTTCTGTTGC ATGATTTCCC AAATGAAATA CTGCCTTGGC
           2740       2750       2760       2770       2780       2790       2800
     TAGAGTTTGA AAAACTAATT GAGCCTGTGC CTGGCTAGAA AACAAGCGTT TATTTGAATG TGAATAGTGT
           2810       2820       2830       2840       2850       2860       2870
     TTCAAAGGTA TGTAGTTACA GAATTCCTAC CAAACAGCTT AAATTCTTCA AGAAAGAATT CCTGCAGCAG
           2880       2890       2900       2910       2920       2930       2940
     TTATTCCCTT ACCTGAAGGC TTCAATCATT TGGATCAACA ACTGCTACTC TCGGGAAGAC TCCTCTACTC
           2950       2960       2970       2980       2990       3000       3010
     ACAGCTGAAG AAAATGAGCA CACCCTTCAC ACTGTTATCA CCTATCCTGA AGATGTGATA CACTGAATGG
           3020       3030       3040       3050       3060       3070       3080
     AAATAAATAG ATGTAAATAA AATTGAGWTC TCATTTAAAA AAAACCATGT GCCCAATGGG AAAATGACCT
           3090       3100       3110       3120       3130       3140       3150
     CATGTTGTGG TTTAAACAGC AACTGCACCC ACTAGCACAG CCCATTGAGC TANCCTATAT ATACATCTCT
           3160
     GTCAGTGCCC CTC
```

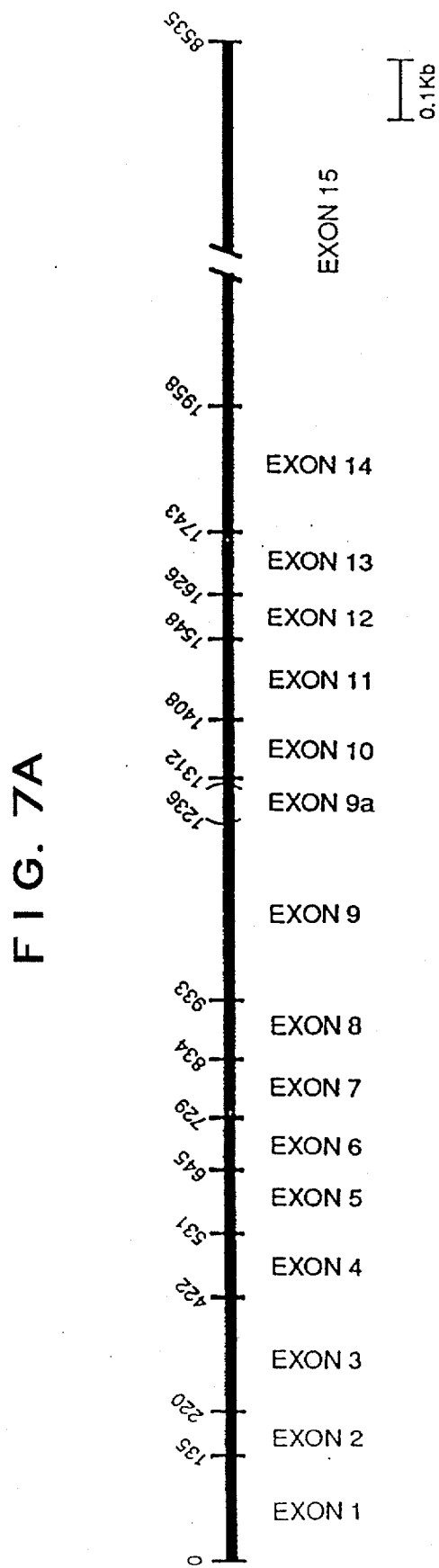

FIG. 7B-1

| 5' flanking (intron) | Exon | 3' flanking (intron) |
|---|---|---|
| TTTAGAATTCATGTTAATATATTGTGTTCTTTTAACAG | EXON 1 | GTATCAAGACTGTGACTTTTAATTGTAGTTTATCCATTTT |
| AAGCAATTGTGTATAAAACTTGTTTCTATTTTATTTAG | EXON 2  85 nt. | GTAGATTTTAAAAAGGTGTTTAAAATAATTTTTTAAGCT |
| NNNNNNNNNNGTCCCTTTTTTAAAAAAAAAAAATAG | EXON 3  202 nt. | GTAACTTTTCTTCATATAGTAAACATTGCCTTGTACTC |
| ATACAAGATATTGATACTTTTTATTATTGTGGTTTTAG | EXON 4  109 nt. | GTAAGTAACTTGGCAGTACAACTTATTGAAACTTTAATA |
| AATAAAAACATAACTAATTAGGTTCTTGTTTATTTTAG | EXON 5  114 nt. | GTAAGTTACTTGTTCTAAGTGATAAACAGYGAAGAGCT |
| ACCATTTTTGCATGTACTGATGTTAACTCCATCTTAACAG | EXON 6  84 nt. | GTTAGTAAATTSCCTTTTTTGTTGTGGGTATAAAATAG |
|  | EXON 7  105 nt. | GTAAATAAATTATTTTATCATATTTTTAAAATTATTTAA |

5'     3'

SEQUENCE LISTING ( 1 ) GENERAL INFORMATION:

( i i i ) NUMBER OF SEQUENCES: 102

( 2 ) INFORMATION FOR SEQ ID NO:1:

( i ) SEQUENCE CHARACTERISTICS:
        ( A ) LENGTH: 9606 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: DP2.5(APC)

( i x ) FEATURE:
        ( A ) NAME/KEY: CDS (B) LOCATION: 34..8562

(xi) SEQUENCE DESCRIPTION: SEQ ID NO:1:

| | | | | | | | | | | | | |
|---|---|---|---|---|---|---|---|---|---|---|---|---|
| GGACTCGGAA ATGAGGTCCA AGGGTAGCCA AGG | ATG Met 1 | GCT Ala | GCA Ala | GCT Ala | TCA Ser 5 | TAT Tyr | GAT Asp | | | | | 54 |
| CAG Gln | TTG Leu | TTA Leu 10 | AAG Lys | CAA Gln | GTT Val | GAG Glu | GCA Ala 15 | CTG Leu | AAG Lys | ATG Met | GAG Glu | AAC Asn 20 | TCA Ser | AAT Asn | CTT Leu | 102 |
| CGA Arg | CAA Gln 25 | GAG Glu | CTA Leu | GAA Glu | GAT Asp | AAT Asn 30 | TCC Ser | AAT Asn | CAT His | CTT Leu | ACA Thr 35 | AAA Lys | CTG Leu | GAA Glu | ACT Thr | 150 |
| GAG Glu 40 | GCA Ala | TCT Ser | AAT Asn | ATG Met | AAG Lys 45 | GAA Glu | GTA Val | CTT Leu | AAA Lys | CAA Gln 50 | CTA Leu | CAA Gln | GGA Gly | AGT Ser | ATT Ile 55 | 198 |
| GAA Glu | GAT Asp | GAA Glu | GCT Ala | ATG Met 60 | GCT Ala | TCT Ser | TCT Ser | GGA Gly | CAG Gln 65 | ATT Ile | GAT Asp | TTA Leu | TTA Leu | GAG Glu 70 | CGT Arg | 246 |
| CTT Leu | AAA Lys | GAG Glu | CTT Leu 75 | AAC Asn | TTA Leu | GAT Asp | AGC Ser | AGT Ser 80 | AAT Asn | TTC Phe | CCT Pro | GGA Gly | GTA Val 85 | AAA Lys | CTG Leu | 294 |
| CGG Arg | TCA Ser | AAA Lys 90 | ATG Met | TCC Ser | CTC Leu | CGT Arg | TCT Ser 95 | TAT Tyr | GGA Gly | AGC Ser | CGG Arg | GAA Glu 100 | GGA Gly | TCT Ser | GTA Val | 342 |
| TCA Ser | AGC Ser 105 | CGT Arg | TCT Ser | GGA Gly | GAG Glu | TGC Cys 110 | AGT Ser | CCT Pro | GTT Val | CCT Pro | ATG Met 115 | GGT Gly | TCA Ser | TTT Phe | CCA Pro | 390 |
| AGA Arg 120 | AGA Arg | GGG Gly | TTT Phe | GTA Val | AAT Asn 125 | GGA Gly | AGC Ser | AGA Arg | GAA Glu | AGT Ser 130 | ACT Thr | GGA Gly | TAT Tyr | TTA Leu | GAA Glu 135 | 438 |
| GAA Glu | CTT Leu | GAG Glu | AAA Lys | GAG Glu 140 | AGG Arg | TCA Ser | TTG Leu | CTT Leu | CTT Leu 145 | GCT Ala | GAT Asp | CTT Leu | GAC Asp | AAA Lys 150 | GAA Glu | 486 |
| GAA Glu | AAG Lys | GAA Glu | AAA Lys 155 | GAC Asp | TGG Trp | TAT Tyr | TAC Tyr | GCT Ala 160 | CAA Gln | CTT Leu | CAG Gln | AAT Asn | CTC Leu 165 | ACT Thr | AAA Lys | 534 |
| AGA Arg | ATA Ile | GAT Asp 170 | AGT Ser | CTT Leu | CCT Pro | TTA Leu | ACT Thr 175 | GAA Glu | AAT Asn | TTT Phe | TCC Ser | TTA Leu 180 | CAA Gln | ACA Thr | GAT Asp | 582 |
| TTG Leu | ACC Thr 185 | AGA Arg | AGG Arg | CAA Gln | TTG Leu | GAA Glu 190 | TAT Tyr | GAA Glu | GCA Ala | AGG Arg | CAA Gln 195 | ATC Ile | AGA Arg | GTT Val | GCG Ala | 630 |
| ATG Met 200 | GAA Glu | GAA Glu | CAA Gln | CTA Leu | GGT Gly 205 | ACC Thr | TGC Cys | CAG Gln | GAT Asp | ATG Met 210 | GAA Glu | AAA Lys | CGA Arg | GCA Ala | CAG Gln 215 | 678 |
| CGA Arg | AGA Arg | ATA Ile | GCC Ala | AGA Arg 220 | ATT Ile | CAG Gln | CAA Gln | ATC Ile | GAA Glu 225 | AAG Lys | GAC Asp | ATA Ile | CTT Leu | CGT Arg 230 | ATA Ile | 726 |
| CGA Arg | CAG Gln | CTT Leu | TTA Leu 235 | CAG Gln | TCC Ser | CAA Gln | GCA Ala | ACA Thr 240 | GAA Glu | GCA Ala | GAG Glu | AGG Arg | TCA Ser 245 | TCT Ser | CAG Gln | 774 |
| AAC Asn | AAG Lys 250 | CAT His | GAA Glu | ACC Thr | GGC Gly | TCA Ser 255 | CAT His | GAT Asp | GCT Ala | GAG Glu | CGG Arg 260 | CAG Gln | AAT Asn | GAA Glu | GGT Gly | 822 |
| CAA Gln | GGA Gly | GTG Val 265 | GGA Gly | GAA Glu | ATC Ile | AAC Asn | ATG Met 270 | GCA Ala | ACT Thr | TCT Ser | GGT Gly | AAT Asn 275 | GGT Gly | CAG Gln | GGT Gly | 870 |
| TCA Ser | ACT Thr 280 | ACA Thr | CGA Arg | ATG Met | GAC Asp | CAT His 285 | GAA Glu | ACA Thr | GCC Ala | AGT Ser | GTT Val 290 | TTG Leu | AGT Ser | TCT Ser | AGT Ser 295 | 918 |

| | | | | | | | | | | | | | | | | |
|---|---|---|---|---|---|---|---|---|---|---|---|---|---|---|---|---|
| AGC | ACA | CAC | TCT | GCA | CCT | CGA | AGG | CTG | ACA | AGT | CAT | CTG | GGA | ACC | AAG | 966 |
| Ser | Thr | His | Ser | Ala 300 | Pro | Arg | Arg | Leu | Thr 305 | Ser | His | Leu | Gly | Thr 310 | Lys | |
| GTG | GAA | ATG | GTG | TAT | TCA | TTG | TTG | TCA | ATG | CTT | GGT | ACT | CAT | GAT | AAG | 1014 |
| Val | Glu | Met | Val 315 | Tyr | Ser | Leu | Leu | Ser 320 | Met | Leu | Gly | Thr | His 325 | Asp | Lys | |
| GAT | GAT | ATG | TCG | CGA | ACT | TTG | CTA | GCT | ATG | TCT | AGC | TCC | CAA | GAC | AGC | 1062 |
| Asp | Asp | Met 330 | Ser | Arg | Thr | Leu | Leu 335 | Ala | Met | Ser | Ser | Ser 340 | Gln | Asp | Ser | |
| TGT | ATA | TCC | ATG | CGA | CAG | TCT | GGA | TGT | CTT | CCT | CTC | CTC | ATC | CAG | CTT | 1110 |
| Cys | Ile 345 | Ser | Met | Arg | Gln | Ser 350 | Gly | Cys | Leu | Pro | Leu 355 | Leu | Ile | Gln | Leu | |
| TTA | CAT | GGC | AAT | GAC | AAA | GAC | TCT | GTA | TTG | TTG | GGA | AAT | TCC | CGG | GGC | 1158 |
| Leu 360 | His | Gly | Asn | Asp | Lys 365 | Asp | Ser | Val | Leu | Leu 370 | Gly | Asn | Ser | Arg | Gly 375 | |
| AGT | AAA | GAG | GCT | CGG | GCC | AGG | GCC | AGT | GCA | GCA | CTC | CAC | AAC | ATC | ATT | 1206 |
| Ser | Lys | Glu | Ala | Arg 380 | Ala | Arg | Ala | Ser | Ala 385 | Ala | Leu | His | Asn | Ile 390 | Ile | |
| CAC | TCA | CAG | CCT | GAT | GAC | AAG | AGA | GGC | AGG | CGT | GAA | ATC | CGA | GTC | CTT | 1254 |
| His | Ser | Gln | Pro 395 | Asp | Asp | Lys | Arg | Gly 400 | Arg | Arg | Glu | Ile | Arg 405 | Val | Leu | |
| CAT | CTT | TTG | GAA | CAG | ATA | CGC | GCT | TAC | TGT | GAA | ACC | TGT | TGG | GAG | TGG | 1302 |
| His | Leu | Leu 410 | Glu | Gln | Ile | Arg | Ala 415 | Tyr | Cys | Glu | Thr | Cys 420 | Trp | Glu | Trp | |
| CAG | GAA | GCT | CAT | GAA | CCA | GGC | ATG | GAC | CAG | GAC | AAA | AAT | CCA | ATG | CCA | 1350 |
| Gln | Glu | Ala | His | Glu 425 | Pro | Gly | Met | Asp | Gln 430 | Asp | Lys | Asn | Pro | Met 435 | Pro | |
| GCT | CCT | GTT | GAA | CAT | CAG | ATC | TGT | CCT | GCT | GTG | TGT | GTT | CTA | ATG | AAA | 1398 |
| Ala 440 | Pro | Val | Glu | His | Gln 445 | Ile | Cys | Pro | Ala | Val 450 | Cys | Val | Leu | Met | Lys 455 | |
| CTT | TCA | TTT | GAT | GAA | GAG | CAT | AGA | CAT | GCA | ATG | AAT | GAA | CTA | GGG | GGA | 1446 |
| Leu | Ser | Phe | Asp | Glu 460 | Glu | His | Arg | His | Ala 465 | Met | Asn | Glu | Leu | Gly 470 | Gly | |
| CTA | CAG | GCC | ATT | GCA | GAA | TTA | TTG | CAA | GTG | GAC | TGT | GAA | ATG | TAT | GGG | 1494 |
| Leu | Gln | Ala | Ile 475 | Ala | Glu | Leu | Leu | Gln 480 | Val | Asp | Cys | Glu | Met 485 | Tyr | Gly | |
| CTT | ACT | AAT | GAC | CAC | TAC | AGT | ATT | ACA | CTA | AGA | CGA | TAT | GCT | GGA | ATG | 1542 |
| Leu | Thr | Asn 490 | Asp | His | Tyr | Ser | Ile 495 | Thr | Leu | Arg | Arg | Tyr 500 | Ala | Gly | Met | |
| GCT | TTG | ACA | AAC | TTG | ACT | TTT | GGA | GAT | GTA | GCC | AAC | AAG | GCT | ACG | CTA | 1590 |
| Ala | Leu | Thr 505 | Asn | Leu | Thr | Phe | Gly 510 | Asp | Val | Ala | Asn | Lys 515 | Ala | Thr | Leu | |
| TGC | TCT | ATG | AAA | GGC | TGC | ATG | AGA | GCA | CTT | GTG | GCC | CAA | CTA | AAA | TCT | 1638 |
| Cys 520 | Ser | Met | Lys | Gly | Cys 525 | Met | Arg | Ala | Leu | Val 530 | Ala | Gln | Leu | Lys | Ser 535 | |
| GAA | AGT | GAA | GAC | TTA | CAG | CAG | GTT | ATT | GCA | AGT | GTT | TTG | AGG | AAT | TTG | 1686 |
| Glu | Ser | Glu | Asp | Leu 540 | Gln | Gln | Val | Ile | Ala 545 | Ser | Val | Leu | Arg | Asn 550 | Leu | |
| TCT | TGG | CGA | GCA | GAT | GTA | AAT | AGT | AAA | AAG | ACG | TTG | CGA | GAA | GTT | GGA | 1734 |
| Ser | Trp | Arg | Ala 555 | Asp | Val | Asn | Ser | Lys 560 | Lys | Thr | Leu | Arg | Glu 565 | Val | Gly | |
| AGT | GTG | AAA | GCA | TTG | ATG | GAA | TGT | GCT | TTA | GAA | GTT | AAA | AAG | GAA | TCA | 1782 |
| Ser | Val | Lys 570 | Ala | Leu | Met | Glu | Cys 575 | Ala | Leu | Glu | Val | Lys 580 | Lys | Glu | Ser | |
| ACC | CTC | AAA | AGC | GTA | TTG | AGT | GCC | TTA | TGG | AAT | TTG | TCA | GCA | CAT | TGC | 1830 |
| Thr | Leu 585 | Lys | Ser | Val | Leu | Ser 590 | Ala | Leu | Trp | Asn | Leu 595 | Ser | Ala | His | Cys | |
| ACT | GAG | AAT | AAA | GCT | GAT | ATA | TGT | GCT | GTA | GAT | GGT | GCA | CTT | GCA | TTT | 1878 |
| Thr 600 | Glu | Asn | Lys | Ala | Asp 605 | Ile | Cys | Ala | Val | Asp 610 | Gly | Ala | Leu | Ala | Phe 615 | |

| | | | | | | | | | | | | | | | | |
|---|---|---|---|---|---|---|---|---|---|---|---|---|---|---|---|---|
| TTG | GTT | GGC | ACT | CTT | ACT | TAC | CGG | AGC | CAG | ACA | AAC | ACT | TTA | GCC | ATT | 1926 |
| Leu | Val | Gly | Thr | Leu<br>620 | Thr | Tyr | Arg | Ser | Gln<br>625 | Thr | Asn | Thr | Leu | Ala<br>630 | Ile | |
| ATT | GAA | AGT | GGA | GGT | GGG | ATA | TTA | CGG | AAT | GTG | TCC | AGC | TTG | ATA | GCT | 1974 |
| Ile | Glu | Ser | Gly<br>635 | Gly | Gly | Ile | Leu | Arg<br>640 | Asn | Val | Ser | Ser | Leu<br>645 | Ile | Ala | |
| ACA | AAT | GAG | GAC | CAC | AGG | CAA | ATC | CTA | AGA | GAG | AAC | AAC | TGT | CTA | CAA | 2022 |
| Thr | Asn | Glu | Asp<br>650 | His | Arg | Gln | Ile | Leu<br>655 | Arg | Glu | Asn | Asn<br>660 | Cys | Leu | Gln | |
| ACT | TTA | TTA | CAA | CAC | TTA | AAA | TCT | CAT | AGT | TTG | ACA | ATA | GTC | AGT | AAT | 2070 |
| Thr | Leu | Leu<br>665 | Gln | His | Leu | Lys | Ser<br>670 | His | Ser | Leu | Thr | Ile<br>675 | Val | Ser | Asn | |
| GCA | TGT | GGA | ACT | TTG | TGG | AAT | CTC | TCA | GCA | AGA | AAT | CCT | AAA | GAC | CAG | 2118 |
| Ala<br>680 | Cys | Gly | Thr | Leu | Trp<br>685 | Asn | Leu | Ser | Ala | Arg<br>690 | Asn | Pro | Lys | Asp | Gln<br>695 | |
| GAA | GCA | TTA | TGG | GAC | ATG | GGG | GCA | GTT | AGC | ATG | CTC | AAG | AAC | CTC | ATT | 2166 |
| Glu | Ala | Leu | Trp | Asp<br>700 | Met | Gly | Ala | Val | Ser<br>705 | Met | Leu | Lys | Asn | Leu<br>710 | Ile | |
| CAT | TCA | AAG | CAC | AAA | ATG | ATT | GCT | ATG | GGA | AGT | GCT | GCA | GCT | TTA | AGG | 2214 |
| His | Ser | Lys | His<br>715 | Lys | Met | Ile | Ala | Met<br>720 | Gly | Ser | Ala | Ala | Ala<br>725 | Leu | Arg | |
| AAT | CTC | ATG | GCA | AAT | AGG | CCT | GCG | AAG | TAC | AAG | GAT | GCC | AAT | ATT | ATG | 2262 |
| Asn | Leu | Met<br>730 | Ala | Asn | Arg | Pro | Ala<br>735 | Lys | Tyr | Lys | Asp | Ala<br>740 | Asn | Ile | Met | |
| TCT | CCT | GGC | TCA | AGC | TTG | CCA | TCT | CTT | CAT | GTT | AGG | AAA | CAA | AAA | GCC | 2310 |
| Ser | Pro | Gly | Ser<br>745 | Ser | Leu | Pro | Ser | Leu<br>750 | His | Val | Arg | Lys | Gln<br>755 | Lys | Ala | |
| CTA | GAA | GCA | GAA | TTA | GAT | GCT | CAG | CAC | TTA | TCA | GAA | ACT | TTT | GAC | AAT | 2358 |
| Leu<br>760 | Glu | Ala | Glu | Leu | Asp<br>765 | Ala | Gln | His | Leu | Ser<br>770 | Glu | Thr | Phe | Asp | Asn<br>775 | |
| ATA | GAC | AAT | TTA | AGT | CCC | AAG | GCA | TCT | CAT | CGT | AGT | AAG | CAG | AGA | CAC | 2406 |
| Ile | Asp | Asn | Leu | Ser<br>780 | Pro | Lys | Ala | Ser | His<br>785 | Arg | Ser | Lys | Gln | Arg<br>790 | His | |
| AAG | CAA | AGT | CTC | TAT | GGT | GAT | TAT | GTT | TTT | GAC | ACC | AAT | CGA | CAT | GAT | 2454 |
| Lys | Gln | Ser | Leu<br>795 | Tyr | Gly | Asp | Tyr | Val<br>800 | Phe | Asp | Thr | Asn | Arg<br>805 | His | Asp | |
| GAT | AAT | AGG | TCA | GAC | AAT | TTT | AAT | ACT | GGC | AAC | ATG | ACT | GTC | CTT | TCA | 2502 |
| Asp | Asn | Arg<br>810 | Ser | Asp | Asn | Phe | Asn<br>815 | Thr | Gly | Asn | Met | Thr<br>820 | Val | Leu | Ser | |
| CCA | TAT | TTG | AAT | ACT | ACA | GTG | TTA | CCC | AGC | TCC | TCT | TCA | TCA | AGA | GGA | 2550 |
| Pro | Tyr | Leu | Asn | Thr<br>825 | Thr | Val | Leu | Pro<br>830 | Ser | Ser | Ser | Ser<br>835 | Ser | Arg | Gly | |
| AGC | TTA | GAT | AGT | TCT | CGT | TCT | GAA | AAA | GAT | AGA | AGT | TTG | GAG | AGA | GAA | 2598 |
| Ser<br>840 | Leu | Asp | Ser | Ser | Arg<br>845 | Ser | Glu | Lys | Asp | Arg<br>850 | Ser | Leu | Glu | Arg | Glu<br>855 | |
| CGC | GGA | ATT | GGT | CTA | GGC | AAC | TAC | CAT | CCA | GCA | ACA | GAA | AAT | CCA | GGA | 2646 |
| Arg | Gly | Ile | Gly | Leu<br>860 | Gly | Asn | Tyr | His | Pro<br>865 | Ala | Thr | Glu | Asn | Pro<br>870 | Gly | |
| ACT | TCT | TCA | AAG | CGA | GGT | TTG | CAG | ATC | TCC | ACC | ACT | GCA | GCC | CAG | ATT | 2694 |
| Thr | Ser | Ser | Lys<br>875 | Arg | Gly | Leu | Gln | Ile<br>880 | Ser | Thr | Thr | Ala | Ala<br>885 | Gln | Ile | |
| GCC | AAA | GTC | ATG | GAA | GAA | GTG | TCA | GCC | ATT | CAT | ACC | TCT | CAG | GAA | GAC | 2742 |
| Ala | Lys | Val<br>890 | Met | Glu | Glu | Val | Ser<br>895 | Ala | Ile | His | Thr | Ser<br>900 | Gln | Glu | Asp | |
| AGA | AGT | TCT | GGG | TCT | ACC | ACT | GAA | TTA | CAT | TGT | GTG | ACA | GAT | GAG | AGA | 2790 |
| Arg | Ser | Ser<br>905 | Gly | Ser | Thr | Thr | Glu<br>910 | Leu | His | Cys | Val | Thr<br>915 | Asp | Glu | Arg | |
| AAT | GCA | CTT | AGA | AGA | AGC | TCT | GCT | GCC | CAT | ACA | CAT | TCA | AAC | ACT | TAC | 2838 |
| Asn | Ala | Leu | Arg<br>920 | Arg | Ser | Ser | Ala<br>925 | Ala | His | Thr | His<br>930 | Ser | Asn | Thr | Tyr<br>935 | |

-continued

| | |
|---|---|
| AAT TTC ACT AAG TCG GAA AAT TCA AAT AGG ACA TGT TCT ATG CCT TAT<br>Asn Phe Thr Lys Ser Glu Asn Ser Asn Arg Thr Cys Ser Met Pro Tyr<br>940                       945                        950 | 2886 |
| GCC AAA TTA GAA TAC AAG AGA TCT TCA AAT GAT AGT TTA AAT AGT GTC<br>Ala Lys Leu Glu Tyr Lys Arg Ser Ser Asn Asp Ser Leu Asn Ser Val<br>955                       960                        965 | 2934 |
| AGT AGT AAT GAT GGT TAT GGT AAA AGA GGT CAA ATG AAA CCC TCG ATT<br>Ser Ser Asn Asp Gly Tyr Gly Lys Arg Gly Gln Met Lys Pro Ser Ile<br>970                       975                        980 | 2982 |
| GAA TCC TAT TCT GAA GAT GAT GAA AGT AAG TTT TGC AGT TAT GGT CAA<br>Glu Ser Tyr Ser Glu Asp Asp Glu Ser Lys Phe Cys Ser Tyr Gly Gln<br>985                       990                        995 | 3030 |
| TAC CCA GCC GAC CTA GCC CAT AAA ATA CAT AGT GCA AAT CAT ATG GAT<br>Tyr Pro Ala Asp Leu Ala His Lys Ile His Ser Ala Asn His Met Asp<br>1000                    1005                  1010                  1015 | 3078 |
| GAT AAT GAT GGA GAA CTA GAT ACA CCA ATA AAT TAT AGT CTT AAA TAT<br>Asp Asn Asp Gly Glu Leu Asp Thr Pro Ile Asn Tyr Ser Leu Lys Tyr<br>1020                    1025                  1030 | 3126 |
| TCA GAT GAG CAG TTG AAC TCT GGA AGG CAA AGT CCT TCA CAG AAT GAA<br>Ser Asp Glu Gln Leu Asn Ser Gly Arg Gln Ser Pro Ser Gln Asn Glu<br>1035                    1040                  1045 | 3174 |
| AGA TGG GCA AGA CCC AAA CAC ATA ATA GAA GAT GAA ATA AAA CAA AGT<br>Arg Trp Ala Arg Pro Lys His Ile Ile Glu Asp Glu Ile Lys Gln Ser<br>1050                    1055                  1060 | 3222 |
| GAG CAA AGA CAA TCA AGG AAT CAA AGT ACA ACT TAT CCT GTT TAT ACT<br>Glu Gln Arg Gln Ser Arg Asn Gln Ser Thr Thr Tyr Pro Val Tyr Thr<br>1065                    1070                  1075 | 3270 |
| GAG AGC ACT GAT GAT AAA CAC CTC AAG TTC CAA CCA CAT TTT GGA CAG<br>Glu Ser Thr Asp Asp Lys His Leu Lys Phe Gln Pro His Phe Gly Gln<br>1080                    1085                  1090                  1095 | 3318 |
| CAG GAA TGT GTT TCT CCA TAC AGG TCA CGG GGA GCC AAT GGT TCA GAA<br>Gln Glu Cys Val Ser Pro Tyr Arg Ser Arg Gly Ala Asn Gly Ser Glu<br>1100                    1105                  1110 | 3366 |
| ACA AAT CGA GTG GGT TCT AAT CAT GGA ATT AAT CAA AAT GTA AGC CAG<br>Thr Asn Arg Val Gly Ser Asn His Gly Ile Asn Gln Asn Val Ser Gln<br>1115                    1120                  1125 | 3414 |
| TCT TTG TGT CAA GAA GAT GAC TAT GAA GAT GAT AAG CCT ACC AAT TAT<br>Ser Leu Cys Gln Glu Asp Asp Tyr Glu Asp Asp Lys Pro Thr Asn Tyr<br>1130                    1135                  1140 | 3462 |
| AGT GAA CGT TAC TCT GAA GAA GAA CAG CAT GAA GAA GAA GAG AGA CCA<br>Ser Glu Arg Tyr Ser Glu Glu Glu Gln His Glu Glu Glu Glu Arg Pro<br>1145                    1150                  1155 | 3510 |
| ACA AAT TAT AGC ATA AAA TAT AAT GAA GAG AAA CGT CAT GTG GAT CAG<br>Thr Asn Tyr Ser Ile Lys Tyr Asn Glu Glu Lys Arg His Val Asp Gln<br>1160                    1165                  1170                  1175 | 3558 |
| CCT ATT GAT TAT AGT TTA AAA TAT GCC ACA GAT ATT CCT TCA TCA CAG<br>Pro Ile Asp Tyr Ser Leu Lys Tyr Ala Thr Asp Ile Pro Ser Ser Gln<br>1180                    1185                  1190 | 3606 |
| AAA CAG TCA TTT TCA TTC TCA AAG AGT TCA TCT GGA CAA AGC AGT AAA<br>Lys Gln Ser Phe Ser Phe Ser Lys Ser Ser Ser Gly Gln Ser Ser Lys<br>1195                    1200                  1205 | 3654 |
| ACC GAA CAT ATG TCT TCA AGC AGT GAG AAT ACG TCC ACA CCT TCA TCT<br>Thr Glu His Met Ser Ser Ser Ser Glu Asn Thr Ser Thr Pro Ser Ser<br>1210                    1215                  1220 | 3702 |
| AAT GCC AAG AGG CAG AAT CAG CTC CAT CCA AGT TCT GCA CAG AGT AGA<br>Asn Ala Lys Arg Gln Asn Gln Leu His Pro Ser Ser Ala Gln Ser Arg<br>1225                    1230                  1235 | 3750 |
| AGT GGT CAG CCT CAA AAG GCT GCC ACT TGC AAA GTT TCT TCT ATT AAC<br>Ser Gly Gln Pro Gln Lys Ala Ala Thr Cys Lys Val Ser Ser Ile Asn<br>1240                    1245                  1250                  1255 | 3798 |

```
CAA GAA ACA ATA CAG ACT TAT TGT GTA GAA GAT ACT CCA ATA TGT TTT    3846
Gln Glu Thr Ile Gln Thr Tyr Cys Val Glu Asp Thr Pro Ile Cys Phe
        1260                1265                1270

TCA AGA TGT AGT TCA TTA TCA TCT TTG TCA TCA GCT GAA GAT GAA ATA    3894
Ser Arg Cys Ser Ser Leu Ser Ser Leu Ser Ser Ala Glu Asp Glu Ile
    1275                1280                1285

GGA TGT AAT CAG ACG ACA CAG GAA GCA GAT TCT GCT AAT ACC CTG CAA    3942
Gly Cys Asn Gln Thr Thr Gln Glu Ala Asp Ser Ala Asn Thr Leu Gln
        1290                1295                1300

ATA GCA GAA ATA AAA GGA AAG ATT GGA ACT AGG TCA GCT GAA GAT CCT    3990
Ile Ala Glu Ile Lys Gly Lys Ile Gly Thr Arg Ser Ala Glu Asp Pro
    1305                1310                1315

GTG AGC GAA GTT CCA GCA GTG TCA CAG CAC CCT AGA ACC AAA TCC AGC    4038
Val Ser Glu Val Pro Ala Val Ser Gln His Pro Arg Thr Lys Ser Ser
1320                1325                1330                1335

AGA CTG CAG GGT TCT AGT TTA TCT TCA GAA TCA GCC AGG CAC AAA GCT    4086
Arg Leu Gln Gly Ser Ser Leu Ser Ser Glu Ser Ala Arg His Lys Ala
        1340                1345                1350

GTT GAA TTT CCT TCA GGA GCG AAA TCT CCC TCC AAA AGT GGT GCT CAG    4134
Val Glu Phe Pro Ser Gly Ala Lys Ser Pro Ser Lys Ser Gly Ala Gln
        1355                1360                1365

ACA CCC AAA AGT CCA CCT GAA CAC TAT GTT CAG GAG ACC CCA CTC ATG    4182
Thr Pro Lys Ser Pro Pro Glu His Tyr Val Gln Glu Thr Pro Leu Met
        1370                1375                1380

TTT AGC AGA TGT ACT TCT GTC AGT TCA CTT GAT AGT TTT GAG AGT CGT    4230
Phe Ser Arg Cys Thr Ser Val Ser Ser Leu Asp Ser Phe Glu Ser Arg
    1385                1390                1395

TCG ATT GCC AGC TCC GTT CAG AGT GAA CCA TGC AGT GGA ATG GTA AGT    4278
Ser Ile Ala Ser Ser Val Gln Ser Glu Pro Cys Ser Gly Met Val Ser
1400                1405                1410                1415

GGC ATT ATA AGC CCC AGT GAT CTT CCA GAT AGC CCT GGA CAA ACC ATG    4326
Gly Ile Ile Ser Pro Ser Asp Leu Pro Asp Ser Pro Gly Gln Thr Met
        1420                1425                1430

CCA CCA AGC AGA AGT AAA ACA CCT CCA CCA CCT CCT CAA ACA GCT CAA    4374
Pro Pro Ser Arg Ser Lys Thr Pro Pro Pro Pro Pro Gln Thr Ala Gln
        1435                1440                1445

ACC AAG CGA GAA GTA CCT AAA AAT AAA GCA CCT ACT GCT GAA AAG AGA    4422
Thr Lys Arg Glu Val Pro Lys Asn Lys Ala Pro Thr Ala Glu Lys Arg
        1450                1455                1460

GAG AGT GGA CCT AAG CAA GCT GCA GTA AAT GCT GCA GTT CAG AGG GTC    4470
Glu Ser Gly Pro Lys Gln Ala Ala Val Asn Ala Ala Val Gln Arg Val
    1465                1470                1475

CAG GTT CTT CCA GAT GCT GAT ACT TTA TTA CAT TTT GCC ACA GAA AGT    4518
Gln Val Leu Pro Asp Ala Asp Thr Leu Leu His Phe Ala Thr Glu Ser
1480                1485                1490                1495

ACT CCA GAT GGA TTT TCT TGT TCA TCC AGC CTG AGT GCT CTG AGC CTC    4566
Thr Pro Asp Gly Phe Ser Cys Ser Ser Ser Leu Ser Ala Leu Ser Leu
        1500                1505                1510

GAT GAG CCA TTT ATA CAG AAA GAT GTG GAA TTA AGA ATA ATG CCT CCA    4614
Asp Glu Pro Phe Ile Gln Lys Asp Val Glu Leu Arg Ile Met Pro Pro
        1515                1520                1525

GTT CAG GAA AAT GAC AAT GGG AAT GAA ACA GAA TCA GAG CAG CCT AAA    4662
Val Gln Glu Asn Asp Asn Gly Asn Glu Thr Glu Ser Glu Gln Pro Lys
        1530                1535                1540

GAA TCA AAT GAA AAC CAA GAG AAA GAG GCA GAA AAA ACT ATT GAT TCT    4710
Glu Ser Asn Glu Asn Gln Glu Lys Glu Ala Glu Lys Thr Ile Asp Ser
    1545                1550                1555

GAA AAG GAC CTA TTA GAT GAT TCA GAT GAT GAT GAT ATT GAA ATA CTA    4758
Glu Lys Asp Leu Leu Asp Asp Ser Asp Asp Asp Asp Ile Glu Ile Leu
    1560                1565                1570                1575
```

-continued

| | |
|---|---|
| GAA GAA TGT ATT ATT TCT GCC ATG CCA ACA AAG TCA TCA CGT AAA GGC<br>Glu Glu Cys Ile Ile Ser Ala Met Pro Thr Lys Ser Ser Arg Lys Gly<br>　　　　1580　　　　　　　　　1585　　　　　　　　　1590 | 4806 |
| AAA AAG CCA GCC CAG ACT GCT TCA AAA TTA CCT CCA CCT GTG GCA AGG<br>Lys Lys Pro Ala Gln Thr Ala Ser Lys Leu Pro Pro Pro Val Ala Arg<br>　　　1595　　　　　　　　　1600　　　　　　　　　1605 | 4854 |
| AAA CCA AGT CAG CTG CCT GTG TAC AAA CTT CTA CCA TCA CAA AAC AGG<br>Lys Pro Ser Gln Leu Pro Val Tyr Lys Leu Leu Pro Ser Gln Asn Arg<br>　　　1610　　　　　　　　　1615　　　　　　　　　1620 | 4902 |
| TTG CAA CCC CAA AAG CAT GTT AGT TTT ACA CCG GGG GAT GAT ATG CCA<br>Leu Gln Pro Gln Lys His Val Ser Phe Thr Pro Gly Asp Asp Met Pro<br>　　　1625　　　　　　　　　1630　　　　　　　　　1635 | 4950 |
| CGG GTG TAT TGT GTT GAA GGG ACA CCT ATA AAC TTT TCC ACA GCT ACA<br>Arg Val Tyr Cys Val Glu Gly Thr Pro Ile Asn Phe Ser Thr Ala Thr<br>1640　　　　　　　　　1645　　　　　　　　　1650　　　　　　　　　1655 | 4998 |
| TCT CTA AGT GAT CTA ACA ATC GAA TCC CCT CCA AAT GAG TTA GCT GCT<br>Ser Leu Ser Asp Leu Thr Ile Glu Ser Pro Pro Asn Glu Leu Ala Ala<br>　　　1660　　　　　　　　　1665　　　　　　　　　1670 | 5046 |
| GGA GAA GGA GTT AGA GGA GGA GCA CAG TCA GGT GAA TTT GAA AAA CGA<br>Gly Glu Gly Val Arg Gly Gly Ala Gln Ser Gly Glu Phe Glu Lys Arg<br>　　　1675　　　　　　　　　1680　　　　　　　　　1685 | 5094 |
| GAT ACC ATT CCT ACA GAA GGC AGA AGT ACA GAT GAG GCT CAA GGA GGA<br>Asp Thr Ile Pro Thr Glu Gly Arg Ser Thr Asp Glu Ala Gln Gly Gly<br>　　　1690　　　　　　　　　1695　　　　　　　　　1700 | 5142 |
| AAA ACC TCA TCT GTA ACC ATA CCT GAA TTG GAT GAC AAT AAA GCA GAG<br>Lys Thr Ser Ser Val Thr Ile Pro Glu Leu Asp Asp Asn Lys Ala Glu<br>　　　1705　　　　　　　　　1710　　　　　　　　　1715 | 5190 |
| GAA GGT GAT ATT CTT GCA GAA TGC ATT AAT TCT GCT ATG CCC AAA GGG<br>Glu Gly Asp Ile Leu Ala Glu Cys Ile Asn Ser Ala Met Pro Lys Gly<br>1720　　　　　　　　　1725　　　　　　　　　1730　　　　　　　　　1735 | 5238 |
| AAA AGT CAC AAG CCT TTC CGT GTG AAA AAG ATA ATG GAC CAG GTC CAG<br>Lys Ser His Lys Pro Phe Arg Val Lys Lys Ile Met Asp Gln Val Gln<br>　　　1740　　　　　　　　　1745　　　　　　　　　1750 | 5286 |
| CAA GCA TCT GCG TCG TCT TCT GCA CCC AAC AAA AAT CAG TTA GAT GGT<br>Gln Ala Ser Ala Ser Ser Ser Ala Pro Asn Lys Asn Gln Leu Asp Gly<br>　　　1755　　　　　　　　　1760　　　　　　　　　1765 | 5334 |
| AAG AAA AAG AAA CCA ACT TCA CCA GTA AAA CCT ATA CCA CAA AAT ACT<br>Lys Lys Lys Lys Pro Thr Ser Pro Val Lys Pro Ile Pro Gln Asn Thr<br>　　　1770　　　　　　　　　1775　　　　　　　　　1780 | 5382 |
| GAA TAT AGG ACA CGT GTA AGA AAA AAT GCA GAC TCA AAA AAT AAT TTA<br>Glu Tyr Arg Thr Arg Val Arg Lys Asn Ala Asp Ser Lys Asn Asn Leu<br>　　　1785　　　　　　　　　1790　　　　　　　　　1795 | 5430 |
| AAT GCT GAG AGA GTT TTC TCA GAC AAC AAA GAT TCA AAG AAA CAG AAT<br>Asn Ala Glu Arg Val Phe Ser Asp Asn Lys Asp Ser Lys Lys Gln Asn<br>1800　　　　　　　　　1805　　　　　　　　　1810　　　　　　　　　1815 | 5478 |
| TTG AAA AAT AAT TCC AAG GAC TTC AAT GAT AAG CTC CCA AAT AAT GAA<br>Leu Lys Asn Asn Ser Lys Asp Phe Asn Asp Lys Leu Pro Asn Asn Glu<br>　　　1820　　　　　　　　　1825　　　　　　　　　1830 | 5526 |
| GAT AGA GTC AGA GGA AGT TTT GCT TTT GAT TCA CCT CAT CAT TAC ACG<br>Asp Arg Val Arg Gly Ser Phe Ala Phe Asp Ser Pro His His Tyr Thr<br>　　　1835　　　　　　　　　1840　　　　　　　　　1845 | 5574 |
| CCT ATT GAA GGA ACT CCT TAC TGT TTT TCA CGA AAT GAT TCT TTG AGT<br>Pro Ile Glu Gly Thr Pro Tyr Cys Phe Ser Arg Asn Asp Ser Leu Ser<br>　　　1850　　　　　　　　　1855　　　　　　　　　1860 | 5622 |
| TCT CTA GAT TTT GAT GAT GAT GAT GTT GAC CTT TCC AGG GAA AAG GCT<br>Ser Leu Asp Phe Asp Asp Asp Asp Val Asp Leu Ser Arg Glu Lys Ala<br>　　　1865　　　　　　　　　1870　　　　　　　　　1875 | 5670 |
| GAA TTA AGA AAG GCA AAA GAA AAT AAG GAA TCA GAG GCT AAA GTT ACC<br>Glu Leu Arg Lys Ala Lys Glu Asn Lys Glu Ser Glu Ala Lys Val Thr<br>1880　　　　　　　　　1885　　　　　　　　　1890　　　　　　　　　1895 | 5718 |

| | | | | | | | | | | | | | | | | |
|---|---|---|---|---|---|---|---|---|---|---|---|---|---|---|---|---|
| AGC | CAC | ACA | GAA | CTA | ACC | TCC | AAC | CAA | CAA | TCA | GCT | AAT | AAG | ACA | CAA | 5766 |
| Ser | His | Thr | Glu | Leu | Thr | Ser | Asn | Gln | Gln | Ser | Ala | Asn | Lys | Thr | Gln | |
| | | | 1900 | | | | | 1905 | | | | | | 1910 | | |

| | | | | | | | | | | | | | | | | |
|---|---|---|---|---|---|---|---|---|---|---|---|---|---|---|---|---|
| GCT | ATT | GCA | AAG | CAG | CCA | ATA | AAT | CGA | GGT | CAG | CCT | AAA | CCC | ATA | CTT | 5814 |
| Ala | Ile | Ala | Lys | Gln | Pro | Ile | Asn | Arg | Gly | Gln | Pro | Lys | Pro | Ile | Leu | |
| | | | 1915 | | | | | 1920 | | | | | 1925 | | | |

| | | | | | | | | | | | | | | | | |
|---|---|---|---|---|---|---|---|---|---|---|---|---|---|---|---|---|
| CAG | AAA | CAA | TCC | ACT | TTT | CCC | CAG | TCA | TCC | AAA | GAC | ATA | CCA | GAC | AGA | 5862 |
| Gln | Lys | Gln | Ser | Thr | Phe | Pro | Gln | Ser | Ser | Lys | Asp | Ile | Pro | Asp | Arg | |
| | | | 1930 | | | | | 1935 | | | | | 1940 | | | |

| | | | | | | | | | | | | | | | | |
|---|---|---|---|---|---|---|---|---|---|---|---|---|---|---|---|---|
| GGG | GCA | GCA | ACT | GAT | GAA | AAG | TTA | CAG | AAT | TTT | GCT | ATT | GAA | AAT | ACT | 5910 |
| Gly | Ala | Ala | Thr | Asp | Glu | Lys | Leu | Gln | Asn | Phe | Ala | Ile | Glu | Asn | Thr | |
| | | | 1945 | | | | | 1950 | | | | | 1955 | | | |

| | | | | | | | | | | | | | | | | |
|---|---|---|---|---|---|---|---|---|---|---|---|---|---|---|---|---|
| CCA | GTT | TGC | TTT | TCT | CAT | AAT | TCC | TCT | CTG | AGT | TCT | CTC | AGT | GAC | ATT | 5958 |
| Pro | Val | Cys | Phe | Ser | His | Asn | Ser | Ser | Leu | Ser | Ser | Leu | Ser | Asp | Ile | |
| 1960 | | | | | 1965 | | | | | 1970 | | | | | 1975 | |

| | | | | | | | | | | | | | | | | |
|---|---|---|---|---|---|---|---|---|---|---|---|---|---|---|---|---|
| GAC | CAA | GAA | AAC | AAC | AAT | AAA | GAA | AAT | GAA | CCT | ATC | AAA | GAG | ACT | GAG | 6006 |
| Asp | Gln | Glu | Asn | Asn | Asn | Lys | Glu | Asn | Glu | Pro | Ile | Lys | Glu | Thr | Glu | |
| | | | | | 1980 | | | | | 1985 | | | | | 1990 | |

| | | | | | | | | | | | | | | | | |
|---|---|---|---|---|---|---|---|---|---|---|---|---|---|---|---|---|
| CCC | CCT | GAC | TCA | CAG | GGA | GAA | CCA | AGT | AAA | CCT | CAA | GCA | TCA | GGC | TAT | 6054 |
| Pro | Pro | Asp | Ser | Gln | Gly | Glu | Pro | Ser | Lys | Pro | Gln | Ala | Ser | Gly | Tyr | |
| | | | 1995 | | | | | 2000 | | | | | 2005 | | | |

| | | | | | | | | | | | | | | | | |
|---|---|---|---|---|---|---|---|---|---|---|---|---|---|---|---|---|
| GCT | CCT | AAA | TCA | TTT | CAT | GTT | GAA | GAT | ACC | CCA | GTT | TGT | TTC | TCA | AGA | 6102 |
| Ala | Pro | Lys | Ser | Phe | His | Val | Glu | Asp | Thr | Pro | Val | Cys | Phe | Ser | Arg | |
| | | | 2010 | | | | | 2015 | | | | | 2020 | | | |

| | | | | | | | | | | | | | | | | |
|---|---|---|---|---|---|---|---|---|---|---|---|---|---|---|---|---|
| AAC | AGT | TCT | CTC | AGT | TCT | CTT | AGT | ATT | GAC | TCT | GAA | GAT | GAC | CTG | TTG | 6150 |
| Asn | Ser | Ser | Leu | Ser | Ser | Leu | Ser | Ile | Asp | Ser | Glu | Asp | Asp | Leu | Leu | |
| | | | 2025 | | | | | 2030 | | | | | 2035 | | | |

| | | | | | | | | | | | | | | | | |
|---|---|---|---|---|---|---|---|---|---|---|---|---|---|---|---|---|
| CAG | GAA | TGT | ATA | AGC | TCC | GCA | ATG | CCA | AAA | AAG | AAA | AAG | CCT | TCA | AGA | 6198 |
| Gln | Glu | Cys | Ile | Ser | Ser | Ala | Met | Pro | Lys | Lys | Lys | Lys | Pro | Ser | Arg | |
| 2040 | | | | | 2045 | | | | | 2050 | | | | | 2055 | |

| | | | | | | | | | | | | | | | | |
|---|---|---|---|---|---|---|---|---|---|---|---|---|---|---|---|---|
| CTC | AAG | GGT | GAT | AAT | GAA | AAA | CAT | AGT | CCC | AGA | AAT | ATG | GGT | GGC | ATA | 6246 |
| Leu | Lys | Gly | Asp | Asn | Glu | Lys | His | Ser | Pro | Arg | Asn | Met | Gly | Gly | Ile | |
| | | | | 2060 | | | | | 2065 | | | | | 2070 | | |

| | | | | | | | | | | | | | | | | |
|---|---|---|---|---|---|---|---|---|---|---|---|---|---|---|---|---|
| TTA | GGT | GAA | GAT | CTG | ACA | CTT | GAT | TTG | AAA | GAT | ATA | CAG | AGA | CCA | GAT | 6294 |
| Leu | Gly | Glu | Asp | Leu | Thr | Leu | Asp | Leu | Lys | Asp | Ile | Gln | Arg | Pro | Asp | |
| | | | 2075 | | | | | 2080 | | | | | 2085 | | | |

| | | | | | | | | | | | | | | | | |
|---|---|---|---|---|---|---|---|---|---|---|---|---|---|---|---|---|
| TCA | GAA | CAT | GGT | CTA | TCC | CCT | GAT | TCA | GAA | AAT | TTT | GAT | TGG | AAA | GCT | 6342 |
| Ser | Glu | His | Gly | Leu | Ser | Pro | Asp | Ser | Glu | Asn | Phe | Asp | Trp | Lys | Ala | |
| | | | 2090 | | | | | 2095 | | | | | 2100 | | | |

| | | | | | | | | | | | | | | | | |
|---|---|---|---|---|---|---|---|---|---|---|---|---|---|---|---|---|
| ATT | CAG | GAA | GGT | GCA | AAT | TCC | ATA | GTA | AGT | AGT | TTA | CAT | CAA | GCT | GCT | 6390 |
| Ile | Gln | Glu | Gly | Ala | Asn | Ser | Ile | Val | Ser | Ser | Leu | His | Gln | Ala | Ala | |
| | | | 2105 | | | | | 2110 | | | | | 2115 | | | |

| | | | | | | | | | | | | | | | | |
|---|---|---|---|---|---|---|---|---|---|---|---|---|---|---|---|---|
| GCT | GCT | GCA | TGT | TTA | TCT | AGA | CAA | GCT | TCG | TCT | GAT | TCA | GAT | TCC | ATC | 6438 |
| Ala | Ala | Ala | Cys | Leu | Ser | Arg | Gln | Ala | Ser | Ser | Asp | Ser | Asp | Ser | Ile | |
| 2120 | | | | | 2125 | | | | | 2130 | | | | | 2135 | |

| | | | | | | | | | | | | | | | | |
|---|---|---|---|---|---|---|---|---|---|---|---|---|---|---|---|---|
| CTT | TCC | CTG | AAA | TCA | GGA | ATC | TCT | CTG | GGA | TCA | CCA | TTT | CAT | CTT | ACA | 6486 |
| Leu | Ser | Leu | Lys | Ser | Gly | Ile | Ser | Leu | Gly | Ser | Pro | Phe | His | Leu | Thr | |
| | | | | 2140 | | | | | 2145 | | | | | 2150 | | |

| | | | | | | | | | | | | | | | | |
|---|---|---|---|---|---|---|---|---|---|---|---|---|---|---|---|---|
| CCT | GAT | CAA | GAA | GAA | AAA | CCC | TTT | ACA | AGT | AAT | AAA | GGC | CCA | CGA | ATT | 6534 |
| Pro | Asp | Gln | Glu | Glu | Lys | Pro | Phe | Thr | Ser | Asn | Lys | Gly | Pro | Arg | Ile | |
| | | | | 2155 | | | | | 2160 | | | | | 2165 | | |

| | | | | | | | | | | | | | | | | |
|---|---|---|---|---|---|---|---|---|---|---|---|---|---|---|---|---|
| CTA | AAA | CCA | GGG | GAG | AAA | AGT | ACA | TTG | GAA | ACT | AAA | AAG | ATA | GAA | TCT | 6582 |
| Leu | Lys | Pro | Gly | Glu | Lys | Ser | Thr | Leu | Glu | Thr | Lys | Lys | Ile | Glu | Ser | |
| | | | 2170 | | | | | 2175 | | | | | 2180 | | | |

| | | | | | | | | | | | | | | | | |
|---|---|---|---|---|---|---|---|---|---|---|---|---|---|---|---|---|
| GAA | AGT | AAA | GGA | ATC | AAA | GGA | GGA | AAA | AAA | GTT | TAT | AAA | AGT | TTG | ATT | 6630 |
| Glu | Ser | Lys | Gly | Ile | Lys | Gly | Gly | Lys | Lys | Val | Tyr | Lys | Ser | Leu | Ile | |
| | | | 2185 | | | | | 2190 | | | | | 2195 | | | |

| | | | | | | | | | | | | | | | | |
|---|---|---|---|---|---|---|---|---|---|---|---|---|---|---|---|---|
| ACT | GGA | AAA | GTT | CGA | TCT | AAT | TCA | GAA | ATT | TCA | GGC | CAA | ATG | AAA | CAG | 6678 |
| Thr | Gly | Lys | Val | Arg | Ser | Asn | Ser | Glu | Ile | Ser | Gly | Gln | Met | Lys | Gln | |
| 2200 | | | | | 2205 | | | | | 2210 | | | | | 2215 | |

| | |
|---|---|
| CCC CTT CAA GCA AAC ATG CCT TCA ATC TCT CGA GGC AGG ACA ATG ATT<br>Pro Leu Gln Ala Asn Met Pro Ser Ile Ser Arg Gly Arg Thr Met Ile<br>2220                        2225                    2230 | 6726 |
| CAT ATT CCA GGA GTT CGA AAT AGC TCC TCA AGT ACA AGT CCT GTT TCT<br>His Ile Pro Gly Val Arg Asn Ser Ser Ser Ser Thr Ser Pro Val Ser<br>2235                      2240                      2245 | 6774 |
| AAA AAA GGC CCA CCC CTT AAG ACT CCA GCC TCC AAA AGC CCT AGT GAA<br>Lys Lys Gly Pro Pro Leu Lys Thr Pro Ala Ser Lys Ser Pro Ser Glu<br>2250                      2255                    2260 | 6822 |
| GGT CAA ACA GCC ACC ACT TCT CCT AGA GGA GCC AAG CCA TCT GTG AAA<br>Gly Gln Thr Ala Thr Thr Ser Pro Arg Gly Ala Lys Pro Ser Val Lys<br>2265                      2270                    2275 | 6870 |
| TCA GAA TTA AGC CCT GTT GCC AGG CAG ACA TCC CAA ATA GGT GGG TCA<br>Ser Glu Leu Ser Pro Val Ala Arg Gln Thr Ser Gln Ile Gly Gly Ser<br>2280               2285                   2290                  2295 | 6918 |
| AGT AAA GCA CCT TCT AGA TCA GGA TCT AGA GAT TCG ACC CCT TCA AGA<br>Ser Lys Ala Pro Ser Arg Ser Gly Ser Arg Asp Ser Thr Pro Ser Arg<br>2300                      2305                    2310 | 6966 |
| CCT GCC CAG CAA CCA TTA AGT AGA CCT ATA CAG TCT CCT GGC CGA AAC<br>Pro Ala Gln Gln Pro Leu Ser Arg Pro Ile Gln Ser Pro Gly Arg Asn<br>2315                      2320                    2325 | 7014 |
| TCA ATT TCC CCT GGT AGA AAT GGA ATA AGT CCT CCT AAC AAA TTA TCT<br>Ser Ile Ser Pro Gly Arg Asn Gly Ile Ser Pro Pro Asn Lys Leu Ser<br>2330                      2335                    2340 | 7062 |
| CAA CTT CCA AGG ACA TCA TCC CCT AGT ACT GCT TCA ACT AAG TCC TCA<br>Gln Leu Pro Arg Thr Ser Ser Pro Ser Thr Ala Ser Thr Lys Ser Ser<br>2345                      2350                    2355 | 7110 |
| GGT TCT GGA AAA ATG TCA TAT ACA TCT CCA GGT AGA CAG ATG AGC CAA<br>Gly Ser Gly Lys Met Ser Tyr Thr Ser Pro Gly Arg Gln Met Ser Gln<br>2360                      2365                    2370                  2375 | 7158 |
| CAG AAC CTT ACC AAA CAA ACA GGT TTA TCC AAG AAT GCC AGT AGT ATT<br>Gln Asn Leu Thr Lys Gln Thr Gly Leu Ser Lys Asn Ala Ser Ser Ile<br>2380                      2385                    2390 | 7206 |
| CCA AGA AGT GAG TCT GCC TCC AAA GGA CTA AAT CAG ATG AAT AAT GGT<br>Pro Arg Ser Glu Ser Ala Ser Lys Gly Leu Asn Gln Met Asn Asn Gly<br>2395                      2400                    2405 | 7254 |
| AAT GGA GCC AAT AAA AAG GTA GAA CTT TCT AGA ATG TCT TCA ACT AAA<br>Asn Gly Ala Asn Lys Lys Val Glu Leu Ser Arg Met Ser Ser Thr Lys<br>2410                      2415                    2420 | 7302 |
| TCA AGT GGA AGT GAA TCT GAT AGA TCA GAA AGA CCT GTA TTA GTA CGC<br>Ser Ser Gly Ser Glu Ser Asp Arg Ser Glu Arg Pro Val Leu Val Arg<br>2425                      2430                    2435 | 7350 |
| CAG TCA ACT TTC ATC AAA GAA GCT CCA AGC CCA ACC TTA AGA AGA AAA<br>Gln Ser Thr Phe Ile Lys Glu Ala Pro Ser Pro Thr Leu Arg Arg Lys<br>2440                      2445                    2450                  2455 | 7398 |
| TTG GAG GAA TCT GCT TCA TTT GAA TCT CTT TCT CCA TCA TCT AGA CCA<br>Leu Glu Glu Ser Ala Ser Phe Glu Ser Leu Ser Pro Ser Ser Arg Pro<br>2460                      2465                    2470 | 7446 |
| GCT TCT CCC ACT AGG TCC CAG GCA CAA ACT CCA GTT TTA AGT CCT TCC<br>Ala Ser Pro Thr Arg Ser Gln Ala Gln Thr Pro Val Leu Ser Pro Ser<br>2475                      2480                    2485 | 7494 |
| CTT CCT GAT ATG TCT CTA TCC ACA CAT TCG TCT GTT CAG GCT GGT GGA<br>Leu Pro Asp Met Ser Leu Ser Thr His Ser Ser Val Gln Ala Gly Gly<br>2490                      2495                    2500 | 7542 |
| TGG CGA AAA CTC CCA CCT AAT CTC AGT CCC ACT ATA GAG TAT AAT GAT<br>Trp Arg Lys Leu Pro Pro Asn Leu Ser Pro Thr Ile Glu Tyr Asn Asp<br>2505                      2510                    2515 | 7590 |
| GGA AGA CCA GCA AAG CGC CAT GAT ATT GCA CGG TCT CAT TCT GAA AGT<br>Gly Arg Pro Ala Lys Arg His Asp Ile Ala Arg Ser His Ser Glu Ser<br>2520                      2525                    2530                  2535 | 7638 |

```
CCT TCT AGA CTT CCA ATC AAT AGG TCA GGA ACC TGG AAA CGT GAG CAC        7686
Pro Ser Arg Leu Pro Ile Asn Arg Ser Gly Thr Trp Lys Arg Glu His
             2540                2545                2550

AGC AAA CAT TCA TCA TCC CTT CCT CGA GTA AGC ACT TGG AGA AGA ACT        7734
Ser Lys His Ser Ser Ser Leu Pro Arg Val Ser Thr Trp Arg Arg Thr
             2555                2560                2565

GGA AGT TCA TCT TCA ATT CTT TCT GCT TCA TCA GAA TCC AGT GAA AAA        7782
Gly Ser Ser Ser Ser Ile Leu Ser Ala Ser Ser Glu Ser Ser Glu Lys
         2570                2575                2580

GCA AAA AGT GAG GAT GAA AAA CAT GTG AAC TCT ATT TCA GGA ACC AAA        7830
Ala Lys Ser Glu Asp Glu Lys His Val Asn Ser Ile Ser Gly Thr Lys
         2585                2590                2595

CAA AGT AAA GAA AAC CAA GTA TCC GCA AAA GGA ACA TGG AGA AAA ATA        7878
Gln Ser Lys Glu Asn Gln Val Ser Ala Lys Gly Thr Trp Arg Lys Ile
2600            2605                2610                2615

AAA GAA AAT GAA TTT TCT CCC ACA AAT AGT ACT TCT CAG ACC GTT TCC        7926
Lys Glu Asn Glu Phe Ser Pro Thr Asn Ser Thr Ser Gln Thr Val Ser
             2620                2625                2630

TCA GGT GCT ACA AAT GGT GCT GAA TCA AAG ACT CTA ATT TAT CAA ATG        7974
Ser Gly Ala Thr Asn Gly Ala Glu Ser Lys Thr Leu Ile Tyr Gln Met
             2635                2640                2645

GCA CCT GCT GTT TCT AAA ACA GAG GAT GTT TGG GTG AGA ATT GAG GAC        8022
Ala Pro Ala Val Ser Lys Thr Glu Asp Val Trp Val Arg Ile Glu Asp
             2650                2655                2660

TGT CCC ATT AAC AAT CCT AGA TCT GGA AGA TCT CCC ACA GGT AAT ACT        8070
Cys Pro Ile Asn Asn Pro Arg Ser Gly Arg Ser Pro Thr Gly Asn Thr
         2665                2670                2675

CCC CCG GTG ATT GAC AGT GTT TCA GAA AAG GCA AAT CCA AAC ATT AAA        8118
Pro Pro Val Ile Asp Ser Val Ser Glu Lys Ala Asn Pro Asn Ile Lys
2680            2685                2690                2695

GAT TCA AAA GAT AAT CAG GCA AAA CAA AAT GTG GGT AAT GGC AGT GTT        8166
Asp Ser Lys Asp Asn Gln Ala Lys Gln Asn Val Gly Asn Gly Ser Val
             2700                2705                2710

CCC ATG CGT ACC GTG GGT TTG GAA AAT CGC CTG ACC TCC TTT ATT CAG        8214
Pro Met Arg Thr Val Gly Leu Glu Asn Arg Leu Thr Ser Phe Ile Gln
             2715                2720                2725

GTG GAT GCC CCT GAC CAA AAA GGA ACT GAG ATA AAA CCA GGA CAA AAT        8262
Val Asp Ala Pro Asp Gln Lys Gly Thr Glu Ile Lys Pro Gly Gln Asn
             2730                2735                2740

AAT CCT GTC CCT GTA TCA GAG ACT AAT GAA AGT CCT ATA GTG GAA CGT        8310
Asn Pro Val Pro Val Ser Glu Thr Asn Glu Ser Pro Ile Val Glu Arg
2745            2750                2755

ACC CCA TTC AGT TCT AGC AGC TCA AGC AAA CAC AGT TCA CCT AGT GGG        8358
Thr Pro Phe Ser Ser Ser Ser Ser Lys His Ser Ser Pro Ser Gly
2760            2765                2770                2775

ACT GTT GCT GCC AGA GTG ACT CCT TTT AAT TAC AAC CCA AGC CCT AGG        8406
Thr Val Ala Ala Arg Val Thr Pro Phe Asn Tyr Asn Pro Ser Pro Arg
             2780                2785                2790

AAA AGC AGC GCA GAT AGC ACT TCA GCT CGG CCA TCT CAG ATC CCA ACT        8454
Lys Ser Ser Ala Asp Ser Thr Ser Ala Arg Pro Ser Gln Ile Pro Thr
             2795                2800                2805

CCA GTG AAT AAC AAC ACA AAG AAG CGA GAT TCC AAA ACT GAC AGC ACA        8502
Pro Val Asn Asn Asn Thr Lys Lys Arg Asp Ser Lys Thr Asp Ser Thr
         2810                2815                2820

GAA TCC AGT GGA ACC CAA AGT CCT AAG CGC CAT TCT GGG TCT TAC CTT        8550
Glu Ser Ser Gly Thr Gln Ser Pro Lys Arg His Ser Gly Ser Tyr Leu
         2825                2830                2835

GTG ACA TCT GTT TAAAAGAGAG GAAGAATGAA ACTAAGAAAA TTCTATGTTA            8602
Val Thr Ser Val
2840
```

|  |  |  |  |  |  |
|---|---|---|---|---|---|
| ATTACAACTG | CTATATAGAC | ATTTTGTTTC | AAATGAAACT | TTAAAAGACT | GAAAAATTTT | 8662 |
| GTAAATAGGT | TTGATTCTTG | TTAGAGGGTT | TTTGTTCTGG | AAGCCATATT | TGATAGTATA | 8722 |
| CTTTGTCTTC | ACTGGTCTTA | TTTTGGGAGG | CACTCTTGAT | GGTTAGGAAA | AAATAGAAAG | 8782 |
| CCAAGTATGT | TTGTACAGTA | TGTTTACAT | GTATTTAAAG | TAGCATCCCA | TCCCAACTTC | 8842 |
| CTTAATTATT | GCTTGTCTAA | AATAATGAAC | ACTACAGATA | GGAAATATGA | TATATTGCTG | 8902 |
| TTATCAATCA | TTTCTAGATT | ATAAACTGAC | TAAACTTACA | TCAGGGGAAA | ATTGGTATTT | 8962 |
| ATGCAAAAAA | AAAATGTTTT | TGTCCTTGTG | AGTCCATCTA | ACATCATAAT | TAATCATGTG | 9022 |
| GCTGTGAAAT | TCACAGTAAT | ATGGTTCCCG | ATGAACAAGT | TTACCCAGCC | TGCTTTGCTT | 9082 |
| ACTGCATGAA | TGAAACTGAT | GGTTCAATTT | CAGAAGTAAT | GATTAACAGT | TATGTGGTCA | 9142 |
| CATGATGTGC | ATAGAGATAG | CTACAGTGTA | ATAATTTACA | CTATTTTGTG | CTCCAAACAA | 9202 |
| AACAAAAATC | TGTGTAACTG | TAAAACATTG | AATGAAACTA | TTTTACCTGA | ACTAGATTTT | 9262 |
| ATCTGAAAGT | AGGTAGAATT | TTTGCTATGC | TGTAATTTGT | TGTATATTCT | GGTATTTGAG | 9322 |
| GTGAGATGGC | TGCTCTTTAT | TAATGAGACA | TGAATTGTGT | CTCAACAGAA | ACTAAATGAA | 9382 |
| CATTTCAGAA | TAAATTATTG | CTGTATGTAA | ACTGTTACTG | AAATTGGTAT | TTGTTTGAAG | 9442 |
| GGTTTGTTTC | ACATTTGTAT | TAATTAATTG | TTTAAAATGC | CTCTTTTAAA | AGCTTATATA | 9502 |
| AATTTTTTCT | TCAGCTTCTA | TGCATTAAGA | GTAAAATTCC | TCTTACTGTA | ATAAAAACAT | 9562 |
| TGAAGAAGAC | TGTTGCCACT | TAACCATTCC | ATGCGTTGGC | ACTT |  | 9606 |

( 2 ) INFORMATION FOR SEQ ID NO:2:

( i ) SEQUENCE CHARACTERISTICS:
        ( A ) LENGTH: 2843 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Ala Ala Ser Tyr Asp Gln Leu Leu Lys Gln Val Glu Ala Leu
 1               5                  10                  15

Lys Met Glu Asn Ser Asn Leu Arg Gln Glu Leu Glu Asp Asn Ser Asn
            20                  25                  30

His Leu Thr Lys Leu Glu Thr Glu Ala Ser Asn Met Lys Glu Val Leu
        35                  40                  45

Lys Gln Leu Gln Gly Ser Ile Glu Asp Glu Ala Met Ala Ser Ser Gly
    50                  55                  60

Gln Ile Asp Leu Leu Glu Arg Leu Lys Glu Leu Asn Leu Asp Ser Ser
65                  70                  75                  80

Asn Phe Pro Gly Val Lys Leu Arg Ser Lys Met Ser Leu Arg Ser Tyr
                85                  90                  95

Gly Ser Arg Glu Gly Ser Val Ser Ser Arg Ser Gly Glu Cys Ser Pro
            100                 105                 110

Val Pro Met Gly Ser Phe Pro Arg Arg Gly Phe Val Asn Gly Ser Arg
        115                 120                 125

Glu Ser Thr Gly Tyr Leu Glu Glu Leu Glu Lys Glu Arg Ser Leu Leu
    130                 135                 140

Leu Ala Asp Leu Asp Lys Glu Glu Lys Glu Lys Asp Trp Tyr Tyr Ala
145                 150                 155                 160

Gln Leu Gln Asn Leu Thr Lys Arg Ile Asp Ser Leu Pro Leu Thr Glu
                165                 170                 175

Asn Phe Ser Leu Gln Thr Asp Leu Thr Arg Arg Gln Leu Glu Tyr Glu
```

-continued

|     |     |     | 180 |     |     |     |     | 185 |     |     |     | 190 |     |
|-----|-----|-----|-----|-----|-----|-----|-----|-----|-----|-----|-----|-----|-----|
| Ala | Arg | Gln | Ile | Arg | Val | Ala | Met | Glu | Glu | Gln | Leu | Gly | Thr | Cys | Gln |
|     |     | 195 |     |     |     |     | 200 |     |     |     |     | 205 |     |
| Asp | Met | Glu | Lys | Arg | Ala | Gln | Arg | Arg | Ile | Ala | Arg | Ile | Gln | Gln | Ile |
|     | 210 |     |     |     |     | 215 |     |     |     |     |     | 220 |     |
| Glu | Lys | Asp | Ile | Leu | Arg | Ile | Arg | Gln | Leu | Leu | Gln | Ser | Gln | Ala | Thr |
| 225 |     |     |     |     | 230 |     |     |     |     | 235 |     |     |     |     | 240 |
| Glu | Ala | Glu | Arg | Ser | Ser | Gln | Asn | Lys | His | Glu | Thr | Gly | Ser | His | Asp |
|     |     |     |     | 245 |     |     |     |     | 250 |     |     |     |     | 255 |     |
| Ala | Glu | Arg | Gln | Asn | Glu | Gly | Gln | Gly | Val | Gly | Glu | Ile | Asn | Met | Ala |
|     |     |     |     | 260 |     |     |     | 265 |     |     |     |     | 270 |     |
| Thr | Ser | Gly | Asn | Gly | Gln | Gly | Ser | Thr | Thr | Arg | Met | Asp | His | Glu | Thr |
|     |     | 275 |     |     |     |     | 280 |     |     |     |     | 285 |     |
| Ala | Ser | Val | Leu | Ser | Ser | Ser | Thr | His | Ser | Ala | Pro | Arg | Arg | Leu |
|     |     | 290 |     |     |     | 295 |     |     |     |     | 300 |     |     |
| Thr | Ser | His | Leu | Gly | Thr | Lys | Val | Glu | Met | Val | Tyr | Ser | Leu | Leu | Ser |
| 305 |     |     |     |     | 310 |     |     |     |     | 315 |     |     |     |     | 320 |
| Met | Leu | Gly | Thr | His | Asp | Lys | Asp | Asp | Met | Ser | Arg | Thr | Leu | Leu | Ala |
|     |     |     |     | 325 |     |     |     |     | 330 |     |     |     |     | 335 |
| Met | Ser | Ser | Ser | Gln | Asp | Ser | Cys | Ile | Ser | Met | Arg | Gln | Ser | Gly | Cys |
|     |     |     | 340 |     |     |     |     | 345 |     |     |     |     | 350 |
| Leu | Pro | Leu | Leu | Ile | Gln | Leu | Leu | His | Gly | Asn | Asp | Lys | Asp | Ser | Val |
|     |     |     | 355 |     |     |     |     | 360 |     |     |     | 365 |     |
| Leu | Leu | Gly | Asn | Ser | Arg | Gly | Ser | Lys | Glu | Ala | Arg | Ala | Arg | Ala | Ser |
|     | 370 |     |     |     |     | 375 |     |     |     |     | 380 |     |     |
| Ala | Ala | Leu | His | Asn | Ile | Ile | His | Ser | Gln | Pro | Asp | Asp | Lys | Arg | Gly |
| 385 |     |     |     |     | 390 |     |     |     |     | 395 |     |     |     |     | 400 |
| Arg | Arg | Glu | Ile | Arg | Val | Leu | His | Leu | Leu | Glu | Gln | Ile | Arg | Ala | Tyr |
|     |     |     |     | 405 |     |     |     |     | 410 |     |     |     |     | 415 |
| Cys | Glu | Thr | Cys | Trp | Glu | Trp | Gln | Glu | Ala | His | Glu | Pro | Gly | Met | Asp |
|     |     |     | 420 |     |     |     |     | 425 |     |     |     |     | 430 |
| Gln | Asp | Lys | Asn | Pro | Met | Pro | Ala | Pro | Val | Glu | His | Gln | Ile | Cys | Pro |
|     |     | 435 |     |     |     |     | 440 |     |     |     |     | 445 |
| Ala | Val | Cys | Val | Leu | Met | Lys | Leu | Ser | Phe | Asp | Glu | Glu | His | Arg | His |
| 450 |     |     |     |     | 455 |     |     |     |     | 460 |
| Ala | Met | Asn | Glu | Leu | Gly | Gly | Leu | Gln | Ala | Ile | Ala | Glu | Leu | Leu | Gln |
| 465 |     |     |     |     | 470 |     |     |     | 475 |     |     |     |     | 480 |
| Val | Asp | Cys | Glu | Met | Tyr | Gly | Leu | Thr | Asn | Asp | His | Tyr | Ser | Ile | Thr |
|     |     |     |     | 485 |     |     |     |     | 490 |     |     |     |     | 495 |
| Leu | Arg | Arg | Tyr | Ala | Gly | Met | Ala | Leu | Thr | Asn | Leu | Thr | Phe | Gly | Asp |
|     |     |     |     | 500 |     |     |     | 505 |     |     |     |     | 510 |
| Val | Ala | Asn | Lys | Ala | Thr | Leu | Cys | Ser | Met | Lys | Gly | Cys | Met | Arg | Ala |
|     |     | 515 |     |     |     |     | 520 |     |     |     |     | 525 |     |
| Leu | Val | Ala | Gln | Leu | Lys | Ser | Glu | Ser | Glu | Asp | Leu | Gln | Gln | Val | Ile |
|     | 530 |     |     |     |     | 535 |     |     |     |     | 540 |     |     |
| Ala | Ser | Val | Leu | Arg | Asn | Leu | Ser | Trp | Arg | Ala | Asp | Val | Asn | Ser | Lys |
| 545 |     |     |     |     | 550 |     |     |     |     | 555 |     |     |     |     | 560 |
| Lys | Thr | Leu | Arg | Glu | Val | Gly | Ser | Val | Lys | Ala | Leu | Met | Glu | Cys | Ala |
|     |     |     |     | 565 |     |     |     |     | 570 |     |     |     |     | 575 |
| Leu | Glu | Val | Lys | Lys | Glu | Ser | Thr | Leu | Lys | Ser | Val | Leu | Ser | Ala | Leu |
|     |     |     |     | 580 |     |     |     |     | 585 |     |     |     |     | 590 |
| Trp | Asn | Leu | Ser | Ala | His | Cys | Thr | Glu | Asn | Lys | Ala | Asp | Ile | Cys | Ala |
|     |     |     |     | 595 |     |     |     |     | 600 |     |     |     |     | 605 |

-continued

| | | | | | | | | | | | | | | |
|---|---|---|---|---|---|---|---|---|---|---|---|---|---|---|
| Val | Asp | Gly | Ala | Leu | Ala | Phe | Leu | Val | Gly | Thr | Leu | Thr | Tyr | Arg | Ser |
| 610 | | | | | 615 | | | | | 620 | | | | | |
| Gln | Thr | Asn | Thr | Leu | Ala | Ile | Ile | Glu | Ser | Gly | Gly | Gly | Ile | Leu | Arg |
| 625 | | | | | 630 | | | | | 635 | | | | | 640 |
| Asn | Val | Ser | Ser | Leu | Ile | Ala | Thr | Asn | Glu | Asp | His | Arg | Gln | Ile | Leu |
| | | | | 645 | | | | | 650 | | | | | 655 | |
| Arg | Glu | Asn | Asn | Cys | Leu | Gln | Thr | Leu | Leu | Gln | His | Leu | Lys | Ser | His |
| | | | 660 | | | | | 665 | | | | | 670 | | |
| Ser | Leu | Thr | Ile | Val | Ser | Asn | Ala | Cys | Gly | Thr | Leu | Trp | Asn | Leu | Ser |
| | | 675 | | | | | 680 | | | | | 685 | | | |
| Ala | Arg | Asn | Pro | Lys | Asp | Gln | Glu | Ala | Leu | Trp | Asp | Met | Gly | Ala | Val |
| | 690 | | | | | 695 | | | | | 700 | | | | |
| Ser | Met | Leu | Lys | Asn | Leu | Ile | His | Ser | Lys | His | Lys | Met | Ile | Ala | Met |
| 705 | | | | | 710 | | | | | 715 | | | | | 720 |
| Gly | Ser | Ala | Ala | Ala | Leu | Arg | Asn | Leu | Met | Ala | Asn | Arg | Pro | Ala | Lys |
| | | | | 725 | | | | | 730 | | | | | 735 | |
| Tyr | Lys | Asp | Ala | Asn | Ile | Met | Ser | Pro | Gly | Ser | Ser | Leu | Pro | Ser | Leu |
| | | | 740 | | | | | 745 | | | | | 750 | | |
| His | Val | Arg | Lys | Gln | Lys | Ala | Leu | Glu | Ala | Glu | Leu | Asp | Ala | Gln | His |
| | | 755 | | | | | 760 | | | | | 765 | | | |
| Leu | Ser | Glu | Thr | Phe | Asp | Asn | Ile | Asp | Asn | Leu | Ser | Pro | Lys | Ala | Ser |
| | 770 | | | | | 775 | | | | | 780 | | | | |
| His | Arg | Ser | Lys | Gln | Arg | His | Lys | Gln | Ser | Leu | Tyr | Gly | Asp | Tyr | Val |
| 785 | | | | | 790 | | | | | 795 | | | | | 800 |
| Phe | Asp | Thr | Asn | Arg | His | Asp | Asp | Asn | Arg | Ser | Asp | Asn | Phe | Asn | Thr |
| | | | | 805 | | | | | 810 | | | | | 815 | |
| Gly | Asn | Met | Thr | Val | Leu | Ser | Pro | Tyr | Leu | Asn | Thr | Thr | Val | Leu | Pro |
| | | | 820 | | | | | 825 | | | | | 830 | | |
| Ser | Ser | Ser | Ser | Ser | Arg | Gly | Ser | Leu | Asp | Ser | Ser | Arg | Ser | Glu | Lys |
| | | | 835 | | | | | 840 | | | | | 845 | | |
| Asp | Arg | Ser | Leu | Glu | Arg | Glu | Arg | Gly | Ile | Gly | Leu | Gly | Asn | Tyr | His |
| 850 | | | | | 855 | | | | | 860 | | | | | |
| Pro | Ala | Thr | Glu | Asn | Pro | Gly | Thr | Ser | Ser | Lys | Arg | Gly | Leu | Gln | Ile |
| 865 | | | | | 870 | | | | | 875 | | | | | 880 |
| Ser | Thr | Thr | Ala | Ala | Gln | Ile | Ala | Lys | Val | Met | Glu | Glu | Val | Ser | Ala |
| | | | | 885 | | | | | 890 | | | | | 895 | |
| Ile | His | Thr | Ser | Gln | Glu | Asp | Arg | Ser | Ser | Gly | Ser | Thr | Thr | Glu | Leu |
| | | | 900 | | | | | 905 | | | | | 910 | | |
| His | Cys | Val | Thr | Asp | Glu | Arg | Asn | Ala | Leu | Arg | Arg | Ser | Ser | Ala | Ala |
| | | 915 | | | | | 920 | | | | | 925 | | | |
| His | Thr | His | Ser | Asn | Thr | Tyr | Asn | Phe | Thr | Lys | Ser | Glu | Asn | Ser | Asn |
| | 930 | | | | | 935 | | | | | 940 | | | | |
| Arg | Thr | Cys | Ser | Met | Pro | Tyr | Ala | Lys | Leu | Glu | Tyr | Lys | Arg | Ser | Ser |
| 945 | | | | | 950 | | | | | 955 | | | | | 960 |
| Asn | Asp | Ser | Leu | Asn | Ser | Val | Ser | Ser | Asn | Asp | Gly | Tyr | Gly | Lys | Arg |
| | | | | 965 | | | | | 970 | | | | | 975 | |
| Gly | Gln | Met | Lys | Pro | Ser | Ile | Glu | Ser | Tyr | Ser | Glu | Asp | Glu | Ser |
| | | | 980 | | | | | 985 | | | | | 990 | | |
| Lys | Phe | Cys | Ser | Tyr | Gly | Gln | Tyr | Pro | Ala | Asp | Leu | Ala | His | Lys | Ile |
| | | 995 | | | | | 1000 | | | | | 1005 | | | |
| His | Ser | Ala | Asn | His | Met | Asp | Asp | Asn | Asp | Gly | Glu | Leu | Asp | Thr | Pro |
| | 1010 | | | | | 1015 | | | | | 1020 | | | | |
| Ile | Asn | Tyr | Ser | Leu | Lys | Tyr | Ser | Asp | Glu | Gln | Leu | Asn | Ser | Gly | Arg |
| 1025 | | | | | 1030 | | | | | 1035 | | | | | 1040 |

```
Gln  Ser  Pro  Ser  Gln  Asn  Glu  Arg  Trp  Ala  Arg  Pro  Lys  His  Ile  Ile
               1045                    1050                    1055

Glu  Asp  Glu  Ile  Lys  Gln  Ser  Glu  Gln  Arg  Gln  Ser  Arg  Asn  Gln  Ser
          1060                    1065                    1070

Thr  Thr  Tyr  Pro  Val  Tyr  Thr  Glu  Ser  Thr  Asp  Asp  Lys  His  Leu  Lys
          1075                    1080                    1085

Phe  Gln  Pro  His  Phe  Gly  Gln  Gln  Glu  Cys  Val  Ser  Pro  Tyr  Arg  Ser
          1090                    1095                    1100

Arg  Gly  Ala  Asn  Gly  Ser  Glu  Thr  Asn  Arg  Val  Gly  Ser  Asn  His  Gly
1105                    1110                    1115                    1120

Ile  Asn  Gln  Asn  Val  Ser  Gln  Ser  Leu  Cys  Gln  Glu  Asp  Asp  Tyr  Glu
               1125                    1130                    1135

Asp  Asp  Lys  Pro  Thr  Asn  Tyr  Ser  Glu  Arg  Tyr  Ser  Glu  Glu  Glu  Gln
          1140                    1145                    1150

His  Glu  Glu  Glu  Glu  Arg  Pro  Thr  Asn  Tyr  Ser  Ile  Lys  Tyr  Asn  Glu
          1155                    1160                    1165

Glu  Lys  Arg  His  Val  Asp  Gln  Pro  Ile  Asp  Tyr  Ser  Leu  Lys  Tyr  Ala
          1170                    1175                    1180

Thr  Asp  Ile  Pro  Ser  Ser  Gln  Lys  Gln  Ser  Phe  Ser  Phe  Ser  Lys  Ser
1185                    1190                    1195                    1200

Ser  Ser  Gly  Gln  Ser  Ser  Lys  Thr  Glu  His  Met  Ser  Ser  Ser  Ser  Glu
               1205                    1210                    1215

Asn  Thr  Ser  Thr  Pro  Ser  Ser  Asn  Ala  Lys  Arg  Gln  Asn  Gln  Leu  His
               1220                    1225                    1230

Pro  Ser  Ser  Ala  Gln  Ser  Arg  Ser  Gly  Gln  Pro  Gln  Lys  Ala  Ala  Thr
               1235                    1240                    1245

Cys  Lys  Val  Ser  Ser  Ile  Asn  Gln  Glu  Thr  Ile  Gln  Thr  Tyr  Cys  Val
          1250                    1255                    1260

Glu  Asp  Thr  Pro  Ile  Cys  Phe  Ser  Arg  Cys  Ser  Ser  Leu  Ser  Ser  Leu
1265                    1270                    1275                    1280

Ser  Ser  Ala  Glu  Asp  Glu  Ile  Gly  Cys  Asn  Gln  Thr  Thr  Gln  Glu  Ala
               1285                    1290                    1295

Asp  Ser  Ala  Asn  Thr  Leu  Gln  Ile  Ala  Glu  Ile  Lys  Gly  Lys  Ile  Gly
          1300                    1305                    1310

Thr  Arg  Ser  Ala  Glu  Asp  Pro  Val  Ser  Glu  Val  Pro  Ala  Val  Ser  Gln
          1315                    1320                    1325

His  Pro  Arg  Thr  Lys  Ser  Ser  Arg  Leu  Gln  Gly  Ser  Ser  Leu  Ser  Ser
          1330                    1335                    1340

Glu  Ser  Ala  Arg  His  Lys  Ala  Val  Glu  Phe  Pro  Ser  Gly  Ala  Lys  Ser
1345                    1350                    1355                    1360

Pro  Ser  Lys  Ser  Gly  Ala  Gln  Thr  Pro  Lys  Ser  Pro  Pro  Glu  His  Tyr
                    1365                    1370                    1375

Val  Gln  Glu  Thr  Pro  Leu  Met  Phe  Ser  Arg  Cys  Thr  Ser  Val  Ser  Ser
               1380                    1385                    1390

Leu  Asp  Ser  Phe  Glu  Ser  Arg  Ser  Ile  Ala  Ser  Ser  Val  Gln  Ser  Glu
          1395                    1400                    1405

Pro  Cys  Ser  Gly  Met  Val  Ser  Gly  Ile  Ile  Ser  Pro  Ser  Asp  Leu  Pro
          1410                    1415                    1420

Asp  Ser  Pro  Gly  Gln  Thr  Met  Pro  Pro  Ser  Arg  Ser  Lys  Thr  Pro  Pro
1425                    1430                    1435                    1440

Pro  Pro  Pro  Gln  Thr  Ala  Gln  Thr  Lys  Arg  Glu  Val  Pro  Lys  Asn  Lys
               1445                    1450                    1455

Ala  Pro  Thr  Ala  Glu  Lys  Arg  Glu  Ser  Gly  Pro  Lys  Gln  Ala  Ala  Val
```

|        |        |        |        | 1460   |        |        |        | 1465   |        |        |        | 1470   |        |        |
|--------|--------|--------|--------|--------|--------|--------|--------|--------|--------|--------|--------|--------|--------|--------|

Asn Ala Ala Val Gln Arg Val Gln Val Leu Pro Asp Ala Asp Thr Leu
　　　　 1475　　　　　　　　　　　1480　　　　　　　　　　1485

Leu His Phe Ala Thr Glu Ser Thr Pro Asp Gly Phe Ser Cys Ser Ser
1490　　　　　　　　　　　1495　　　　　　　　　　　1500

Ser Leu Ser Ala Leu Ser Leu Asp Glu Pro Phe Ile Gln Lys Asp Val
1505　　　　　　　　　　　1510　　　　　　　　　　　1515　　　　　　　　　　　1520

Glu Leu Arg Ile Met Pro Pro Val Gln Glu Asn Asp Asn Gly Asn Glu
　　　　　　　　　　　1525　　　　　　　　　　　1530　　　　　　　　　　　1535

Thr Glu Ser Glu Gln Pro Lys Glu Ser Asn Glu Asn Gln Glu Lys Glu
　　　　　　　　　1540　　　　　　　　　　　1545　　　　　　　　　　　1550

Ala Glu Lys Thr Ile Asp Ser Glu Lys Asp Leu Leu Asp Asp Ser Asp
　　　　　　　　1555　　　　　　　　　　　1560　　　　　　　　　　　1565

Asp Asp Asp Ile Glu Ile Leu Glu Glu Cys Ile Ile Ser Ala Met Pro
1570　　　　　　　　　　　1575　　　　　　　　　　　1580

Thr Lys Ser Ser Arg Lys Gly Lys Lys Pro Ala Gln Thr Ala Ser Lys
1585　　　　　　　　　　　1590　　　　　　　　　　　1595　　　　　　　　　　　1600

Leu Pro Pro Pro Val Ala Arg Lys Pro Ser Gln Leu Pro Val Tyr Lys
　　　　　　　　　　　1605　　　　　　　　　　　1610　　　　　　　　　　　1615

Leu Leu Pro Ser Gln Asn Arg Leu Gln Pro Gln Lys His Val Ser Phe
　　　　　　　　1620　　　　　　　　　　　1625　　　　　　　　　　　1630

Thr Pro Gly Asp Asp Met Pro Arg Val Tyr Cys Val Glu Gly Thr Pro
　　　　　　　　1635　　　　　　　　　　　1640　　　　　　　　　　　1645

Ile Asn Phe Ser Thr Ala Thr Ser Leu Ser Asp Leu Thr Ile Glu Ser
1650　　　　　　　　　　　1655　　　　　　　　　　　1660

Pro Pro Asn Glu Leu Ala Ala Gly Glu Gly Val Arg Gly Gly Ala Gln
1665　　　　　　　　　　　1670　　　　　　　　　　　1675　　　　　　　　　　　1680

Ser Gly Glu Phe Glu Lys Arg Asp Thr Ile Pro Thr Glu Gly Arg Ser
　　　　　　　　　1685　　　　　　　　　　　1690　　　　　　　　　　　1695

Thr Asp Glu Ala Gln Gly Gly Lys Thr Ser Ser Val Thr Ile Pro Glu
　　　　　　　　　　　1700　　　　　　　　　　　1705　　　　　　　　　　　1710

Leu Asp Asp Asn Lys Ala Glu Glu Gly Asp Ile Leu Ala Glu Cys Ile
　　　　　　　　　　　1715　　　　　　　　　　　1720　　　　　　　　　　　1725

Asn Ser Ala Met Pro Lys Gly Lys Ser His Lys Pro Phe Arg Val Lys
　　　　　　　　　1730　　　　　　　　　　　1735　　　　　　　　　　　1740

Lys Ile Met Asp Gln Val Gln Gln Ala Ser Ala Ser Ser Ser Ala Pro
1745　　　　　　　　　　　1750　　　　　　　　　　　1755　　　　　　　　　　　1760

Asn Lys Asn Gln Leu Asp Gly Lys Lys Lys Lys Pro Thr Ser Pro Val
　　　　　　　　　　　1765　　　　　　　　　　　1770　　　　　　　　　　　1775

Lys Pro Ile Pro Gln Asn Thr Glu Tyr Arg Thr Arg Val Arg Lys Asn
　　　　　　　　　1780　　　　　　　　　　　1785　　　　　　　　　　　1790

Ala Asp Ser Lys Asn Asn Leu Asn Ala Glu Arg Val Phe Ser Asp Asn
　　　　　　　　　1795　　　　　　　　　　　1800　　　　　　　　　　　1805

Lys Asp Ser Lys Lys Gln Asn Leu Lys Asn Asn Ser Lys Asp Phe Asn
　　　　　　　　1810　　　　　　　　　　　1815　　　　　　　　　　　1820

Asp Lys Leu Pro Asn Asn Glu Asp Arg Val Arg Gly Ser Phe Ala Phe
1825　　　　　　　　　　　1830　　　　　　　　　　　1835　　　　　　　　　　　1840

Asp Ser Pro His His Tyr Thr Pro Ile Glu Gly Thr Pro Tyr Cys Phe
　　　　　　　　　　　1845　　　　　　　　　　　1850　　　　　　　　　　　1855

Ser Arg Asn Asp Ser Leu Ser Ser Leu Asp Phe Asp Asp Asp Asp Val
　　　　　　　　　1860　　　　　　　　　　　1865　　　　　　　　　　　1870

Asp Leu Ser Arg Glu Lys Ala Glu Leu Arg Lys Ala Lys Glu Asn Lys
　　　　　　　　1875　　　　　　　　　　　1880　　　　　　　　　　　1885

```
Glu  Ser  Glu  Ala  Lys  Val  Thr  Ser  His  Thr  Glu  Leu  Thr  Ser  Asn  Gln
     1890                1895                1900

Gln  Ser  Ala  Asn  Lys  Thr  Gln  Ala  Ile  Ala  Lys  Gln  Pro  Ile  Asn  Arg
1905                1910                1915                          1920

Gly  Gln  Pro  Lys  Pro  Ile  Leu  Gln  Lys  Gln  Ser  Thr  Phe  Pro  Gln  Ser
               1925                1930                     1935

Ser  Lys  Asp  Ile  Pro  Asp  Arg  Gly  Ala  Ala  Thr  Asp  Glu  Lys  Leu  Gln
               1940                1945                1950

Asn  Phe  Ala  Ile  Glu  Asn  Thr  Pro  Val  Cys  Phe  Ser  His  Asn  Ser  Ser
          1955                1960                     1965

Leu  Ser  Ser  Leu  Ser  Asp  Ile  Asp  Gln  Glu  Asn  Asn  Asn  Lys  Glu  Asn
          1970                1975                1980

Glu  Pro  Ile  Lys  Glu  Thr  Glu  Pro  Pro  Asp  Ser  Gln  Gly  Glu  Pro  Ser
1985                1990                1995                          2000

Lys  Pro  Gln  Ala  Ser  Gly  Tyr  Ala  Pro  Lys  Ser  Phe  His  Val  Glu  Asp
               2005                2010                     2015

Thr  Pro  Val  Cys  Phe  Ser  Arg  Asn  Ser  Ser  Leu  Ser  Ser  Leu  Ser  Ile
               2020                2025                     2030

Asp  Ser  Glu  Asp  Asp  Leu  Leu  Gln  Glu  Cys  Ile  Ser  Ser  Ala  Met  Pro
          2035                2040                     2045

Lys  Lys  Lys  Lys  Pro  Ser  Arg  Leu  Lys  Gly  Asp  Asn  Glu  Lys  His  Ser
2050                     2055                2060

Pro  Arg  Asn  Met  Gly  Gly  Ile  Leu  Gly  Glu  Asp  Leu  Thr  Leu  Asp  Leu
2065                2070                2075                          2080

Lys  Asp  Ile  Gln  Arg  Pro  Asp  Ser  Glu  His  Gly  Leu  Ser  Pro  Asp  Ser
               2085                2090                     2095

Glu  Asn  Phe  Asp  Trp  Lys  Ala  Ile  Gln  Glu  Gly  Ala  Asn  Ser  Ile  Val
               2100                2105                     2110

Ser  Ser  Leu  His  Gln  Ala  Ala  Ala  Ala  Cys  Leu  Ser  Arg  Gln  Ala
          2115                2120                     2125

Ser  Ser  Asp  Ser  Asp  Ser  Ile  Leu  Ser  Leu  Lys  Ser  Gly  Ile  Ser  Leu
          2130                2135                2140

Gly  Ser  Pro  Phe  His  Leu  Thr  Pro  Asp  Gln  Glu  Glu  Lys  Pro  Phe  Thr
2145                     2150                2155                          2160

Ser  Asn  Lys  Gly  Pro  Arg  Ile  Leu  Lys  Pro  Gly  Glu  Lys  Ser  Thr  Leu
                    2165                2170                     2175

Glu  Thr  Lys  Lys  Ile  Glu  Ser  Glu  Ser  Lys  Gly  Ile  Lys  Gly  Gly  Lys
               2180                2185                     2190

Lys  Val  Tyr  Lys  Ser  Leu  Ile  Thr  Gly  Lys  Val  Arg  Ser  Asn  Ser  Glu
          2195                2200                     2205

Ile  Ser  Gly  Gln  Met  Lys  Gln  Pro  Leu  Gln  Ala  Asn  Met  Pro  Ser  Ile
     2210                2215                     2220

Ser  Arg  Gly  Arg  Thr  Met  Ile  His  Ile  Pro  Gly  Val  Arg  Asn  Ser  Ser
2225                     2230                2235                          2240

Ser  Ser  Thr  Ser  Pro  Val  Ser  Lys  Lys  Gly  Pro  Pro  Leu  Lys  Thr  Pro
                    2245                2250                          2255

Ala  Ser  Lys  Ser  Pro  Ser  Glu  Gly  Gln  Thr  Ala  Thr  Thr  Ser  Pro  Arg
               2260                2265                     2270

Gly  Ala  Lys  Pro  Ser  Val  Lys  Ser  Glu  Leu  Ser  Pro  Val  Ala  Arg  Gln
          2275                2280                     2285

Thr  Ser  Gln  Ile  Gly  Gly  Ser  Ser  Lys  Ala  Pro  Ser  Arg  Ser  Gly  Ser
     2290                2295                     2300

Arg  Asp  Ser  Thr  Pro  Ser  Arg  Pro  Ala  Gln  Gln  Pro  Leu  Ser  Arg  Pro
2305                     2310                2315                          2320
```

```
Ile Gln Ser Pro Gly Arg Asn Ser Ile Ser Pro Gly Arg Asn Gly Ile
              2325                2330                2335
Ser Pro Pro Asn Lys Leu Ser Gln Leu Pro Arg Thr Ser Ser Pro Ser
              2340                2345                2350
Thr Ala Ser Thr Lys Ser Ser Gly Ser Gly Lys Met Ser Tyr Thr Ser
              2355                2360                2365
Pro Gly Arg Gln Met Ser Gln Gln Asn Leu Thr Lys Gln Thr Gly Leu
              2370                2375                2380
Ser Lys Asn Ala Ser Ser Ile Pro Arg Ser Glu Ser Ala Ser Lys Gly
2385                2390                2395                2400
Leu Asn Gln Met Asn Asn Gly Asn Gly Ala Asn Lys Lys Val Glu Leu
              2405                2410                2415
Ser Arg Met Ser Ser Thr Lys Ser Ser Gly Ser Glu Ser Asp Arg Ser
              2420                2425                2430
Glu Arg Pro Val Leu Val Arg Gln Ser Thr Phe Ile Lys Glu Ala Pro
              2435                2440                2445
Ser Pro Thr Leu Arg Arg Lys Leu Glu Glu Ser Ala Ser Phe Glu Ser
              2450                2455                2460
Leu Ser Pro Ser Ser Arg Pro Ala Ser Pro Thr Arg Ser Gln Ala Gln
2465                2470                2475                2480
Thr Pro Val Leu Ser Pro Ser Leu Pro Asp Met Ser Leu Ser Thr His
              2485                2490                2495
Ser Ser Val Gln Ala Gly Gly Trp Arg Lys Leu Pro Pro Asn Leu Ser
              2500                2505                2510
Pro Thr Ile Glu Tyr Asn Asp Gly Arg Pro Ala Lys Arg His Asp Ile
              2515                2520                2525
Ala Arg Ser His Ser Glu Ser Pro Ser Arg Leu Pro Ile Asn Arg Ser
              2530                2535                2540
Gly Thr Trp Lys Arg Glu His Ser Lys His Ser Ser Ser Leu Pro Arg
2545                2550                2555                2560
Val Ser Thr Trp Arg Arg Thr Gly Ser Ser Ser Ser Ile Leu Ser Ala
              2565                2570                2575
Ser Ser Glu Ser Ser Glu Lys Ala Lys Ser Glu Asp Glu Lys His Val
              2580                2585                2590
Asn Ser Ile Ser Gly Thr Lys Gln Ser Lys Glu Asn Gln Val Ser Ala
              2595                2600                2605
Lys Gly Thr Trp Arg Lys Ile Lys Glu Asn Glu Phe Ser Pro Thr Asn
              2610                2615                2620
Ser Thr Ser Gln Thr Val Ser Ser Gly Ala Thr Asn Gly Ala Glu Ser
2625                2630                2635                2640
Lys Thr Leu Ile Tyr Gln Met Ala Pro Ala Val Ser Lys Thr Glu Asp
              2645                2650                2655
Val Trp Val Arg Ile Glu Asp Cys Pro Ile Asn Asn Pro Arg Ser Gly
              2660                2665                2670
Arg Ser Pro Thr Gly Asn Thr Pro Pro Val Ile Asp Ser Val Ser Glu
              2675                2680                2685
Lys Ala Asn Pro Asn Ile Lys Asp Ser Lys Asp Asn Gln Ala Lys Gln
              2690                2695                2700
Asn Val Gly Asn Gly Ser Val Pro Met Arg Thr Val Gly Leu Glu Asn
2705                2710                2715                2720
Arg Leu Thr Ser Phe Ile Gln Val Asp Ala Pro Asp Gln Lys Gly Thr
              2725                2730                2735
Glu Ile Lys Pro Gly Gln Asn Asn Pro Val Pro Val Ser Glu Thr Asn
```

|  | 2740 | 2745 | 2750 |
|---|---|---|---|

Glu Ser Pro Ile Val Glu Arg Thr Pro Phe Ser Ser Ser Ser Ser
           2755                2760            2765

Lys His Ser Ser Pro Ser Gly Thr Val Ala Ala Arg Val Thr Pro Phe
2770                2775                2780

Asn Tyr Asn Pro Ser Pro Arg Lys Ser Ser Ala Asp Ser Thr Ser Ala
2785                2790                2795                2800

Arg Pro Ser Gln Ile Pro Thr Pro Val Asn Asn Asn Thr Lys Lys Arg
                2805                2810                2815

Asp Ser Lys Thr Asp Ser Thr Glu Ser Ser Gly Thr Gln Ser Pro Lys
                2820                2825                2830

Arg His Ser Gly Ser Tyr Leu Val Thr Ser Val
             2835                2840

( 2 ) INFORMATION FOR SEQ ID NO:3:

( i ) SEQUENCE CHARACTERISTICS:
        ( A ) LENGTH: 3172 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: DP1(TB2)

( i x ) FEATURE:
        ( A ) NAME/KEY: CDS
        ( B ) LOCATION: 1..630

( x i ) SEQUENCE DESCRIPTION: SEQ ID NO:3:

```
GCA  GTC  GCC  GCT  CCA  GTC  TAT  CCG  GCA  CTA  GGA  ACA  GCC  CCG  GGN  GGC         48
Ala  Val  Ala  Ala  Pro  Val  Tyr  Pro  Ala  Leu  Gly  Thr  Ala  Pro  Gly  Gly
 1              5                        10                       15

GAG  ACG  GTC  CCC  GCC  ATG  TCT  GCG  GCC  ATG  AGG  GAG  AGG  TTC  GAC  CGG         96
Glu  Thr  Val  Pro  Ala  Met  Ser  Ala  Ala  Met  Arg  Glu  Arg  Phe  Asp  Arg
                20                       25                       30

TTC  CTG  CAC  GAG  AAG  AAC  TGC  ATG  ACT  GAC  CTT  CTG  GCC  AAG  CTC  GAG        144
Phe  Leu  His  Glu  Lys  Asn  Cys  Met  Thr  Asp  Leu  Leu  Ala  Lys  Leu  Glu
            35                       40                       45

GCC  AAA  ACC  GGC  GTG  AAC  AGG  AGC  TTC  ATC  GCT  CTT  GGT  GTC  ATC  GGA        192
Ala  Lys  Thr  Gly  Val  Asn  Arg  Ser  Phe  Ile  Ala  Leu  Gly  Val  Ile  Gly
        50                       55                       60

CTG  GTG  GCC  TTG  TAC  CTG  GTG  TTC  GGT  TAT  GGA  GCC  TCT  CTC  CTC  TGC        240
Leu  Val  Ala  Leu  Tyr  Leu  Val  Phe  Gly  Tyr  Gly  Ala  Ser  Leu  Leu  Cys
 65                      70                       75                       80

AAC  CTG  ATA  GGA  TTT  GGC  TAC  CCA  GCC  TAC  ATC  TCA  ATT  AAA  GCT  ATA        288
Asn  Leu  Ile  Gly  Phe  Gly  Tyr  Pro  Ala  Tyr  Ile  Ser  Ile  Lys  Ala  Ile
                         85                       90                       95

GAG  AGT  CCC  AAC  AAA  GAA  GAT  GAT  ACC  CAG  TGG  CTG  ACC  TAC  TGG  GTA        336
Glu  Ser  Pro  Asn  Lys  Glu  Asp  Asp  Thr  Gln  Trp  Leu  Thr  Tyr  Trp  Val
                100                      105                      110

GTG  TAT  GGT  GTG  TTC  AGC  ATT  GCT  GAA  TTC  TTC  TCT  GAT  ATC  TTC  CTG        384
Val  Tyr  Gly  Val  Phe  Ser  Ile  Ala  Glu  Phe  Phe  Ser  Asp  Ile  Phe  Leu
            115                      120                      125

TCA  TGG  TTC  CCC  TTC  TAC  TAC  ATG  CTG  AAG  TGT  GGC  TTC  CTG  TTG  TGG        432
Ser  Trp  Phe  Pro  Phe  Tyr  Tyr  Met  Leu  Lys  Cys  Gly  Phe  Leu  Leu  Trp
        130                      135                      140

TGC  ATG  GCC  CCG  AGC  CCT  TCT  AAT  GGG  GCT  GAA  CTG  CTC  TAC  AAG  CGC        480
```

-continued

| | | | | | | | | | | | | | | | |
|---|---|---|---|---|---|---|---|---|---|---|---|---|---|---|---|
| Cys | Met | Ala | Pro | Ser | Pro | Ser | Asn | Gly | Ala | Glu | Leu | Leu | Tyr | Lys | Arg |
| 145 | | | | | 150 | | | | | 155 | | | | | 160 |

| ATC | ATC | CGT | CCT | TTC | TTC | CTG | AAG | CAC | GAG | TCC | CAG | ATG | GAC | AGT | GTG | 528 |
|---|---|---|---|---|---|---|---|---|---|---|---|---|---|---|---|---|
| Ile | Ile | Arg | Pro | Phe | Phe | Leu | Lys | His | Glu | Ser | Gln | Met | Asp | Ser | Val | |
| | | | | 165 | | | | | 170 | | | | | 175 | | |

| GTC | AAG | GAC | CTT | AAA | GAC | AAG | TCC | AAA | GAG | ACT | GCA | GAT | GCC | ATC | ACT | 576 |
|---|---|---|---|---|---|---|---|---|---|---|---|---|---|---|---|---|
| Val | Lys | Asp | Leu | Lys | Asp | Lys | Ser | Lys | Glu | Thr | Ala | Asp | Ala | Ile | Thr | |
| | | | 180 | | | | | 185 | | | | | 190 | | | |

| AAA | GAA | GCG | AAG | AAA | GCT | ACC | GTG | AAT | TTA | CTG | GGT | GAA | GAA | AAG | AAG | 624 |
|---|---|---|---|---|---|---|---|---|---|---|---|---|---|---|---|---|
| Lys | Glu | Ala | Lys | Lys | Ala | Thr | Val | Asn | Leu | Leu | Gly | Glu | Glu | Lys | Lys | |
| | | 195 | | | | 200 | | | | | 205 | | | | | |

| AGC | ACC | TAAACCAGAC | TAAACCAGAC | TGGATGGAAA | CTTCCTGCCC | TCTCTGTACC | 680 |
|---|---|---|---|---|---|---|---|
| Ser | Thr | | | | | | |
| | 210 | | | | | | |

| TTCCTACTGG | AGCTTGATGT | TATATTAGGG | ACTGTGGTAT | AATTATTTTA | ATAATGTTGC | 740 |
|---|---|---|---|---|---|---|
| CTTGGAAACA | TTTTGAGAT | ATTAAAGATT | GGAATGTGTT | GTAAGTTTCT | TTGCTTACTT | 800 |
| TTACTGTCTA | TATATATAGG | GAGCACTTTA | AACTTAATGC | AGTGGGCAGT | GTCCACGTTT | 860 |
| TTGGAAAATG | TATTTTGCCT | CTGGGTAGGA | AAAGATGTAT | GTTGCTATCC | TGCAGGAAAT | 920 |
| ATAAACTTAA | AATAAAATTA | TATACCCCAC | AGGCTGTGTA | CTTTACTGGG | CTCTCCCTGC | 980 |
| ACGSATTTTC | TCTGTAGTTA | CATTTAGGRT | AATCTTTATG | GTTCTACTTC | CTRTAATGTA | 1040 |
| CAATTTTATA | TAATTCNGRA | ATGTTTTAA | TGTATTTGTG | CACATGTACA | TATGGAAATG | 1100 |
| TTACTGTCTG | ACTACANCAT | GCATCATGCT | CATGGGGAGG | GAGCAGGGGA | AGGTTGTATG | 1160 |
| TGTCATTTAT | AACTTCTGTA | CAGTAAGACC | ACCTGCCAAA | AGCTGGAGGA | ACCATTGTGC | 1220 |
| TGGTGTGGTC | TACTAAATAA | TACTTTAGGA | AATACGTGAT | AATATGCAA | GTGAACAAAG | 1280 |
| TGAGAAATGA | AATCGAATGG | AGATTGGCCT | GGTTGTTTCC | GTAGTATATG | GCATATGAAT | 1340 |
| ACCAGGATAG | CTTTATAAAG | CAGTTAGTTA | GTTAGTTACT | CACTCTAGTG | ATAAATCGGG | 1400 |
| AAATTTACAC | ACACACACAC | ACACACACAC | ACACACACAC | ACACACACAC | ACACACACAG | 1460 |
| AGTACCCTGT | AACTCTCAAT | TCCCTGAAAA | ACTAGTAATA | CTGTCTTATC | TGCTATAAAC | 1520 |
| TTTACATATT | TGTCTATTGT | CAAGATGCTA | CANTGGAMNC | CATTTCTGGT | TTTATCTTCA | 1580 |
| NAGSGGAGAN | ACATGTTGAT | TTAGTCTTCT | TTCCCAATCT | TCTTTTTAA | MCCAGTTTNA | 1640 |
| GGMNCTTCTG | RAGATTTG Y C | CACCTCTGAT | TACATGTATG | TTCT Y GTTTG | TATCATKAGC | 1700 |
| AACAACATGC | TAATGRCGAC | ACCTAGCTCT | RAGMGCAATT | CTGGGAGANT | GARAGGNWGT | 1760 |
| ATARAGTMNC | CCATAATCTG | CTTGGCAATA | GTTAAGTCAA | TCTATCTTCA | GTTTTTCTCT | 1820 |
| GGCCTTTAAG | GTCAAACACA | AGAGGCTTCC | CTAGTTTACA | AGTCAGAGTC | ACTTGTAGTC | 1880 |
| CATTTAAATG | CCCTCATCCG | TATTCTTTGT | GTTGATAAGC | TGCACAKGAC | TACATAGTAA | 1940 |
| GTACAGANCA | GTAAAGTTAA | NNCGGATGTC | TCCATTGATC | TGCCAANTCG | NTATAGAGAG | 2000 |
| CAATTTGTCT | GGACTAGAAA | ATCTGAGTTT | TACACCATAC | TGTTAAGAGT | CCTTTTGAAT | 2060 |
| TAAACTAGAC | TAAAACAAGT | GTATAACTAA | ACTAACAAGA | TTAAATATCC | AGCCAGTACA | 2120 |
| GTATTTTTA | AGGCAAATAA | AGATGATTAG | CTCACCTTGA | GNTAACAATC | AGGTAAGATC | 2180 |
| ATNACAATGT | CTCATGATGT | NAANAATATT | AAAGATATCA | ATACTAAGTG | ACAGTATCAC | 2240 |
| NNCTAATATA | ATATGGATCA | GAGCATTTAT | TTTGGGGAGG | AAAACAGTGG | TGATTACCGG | 2300 |
| CATTTATTA | AACTTAAAAC | TTTGTAGAAA | GCAAACAAAA | TTGTTCTTGG | GAGAAAATCA | 2360 |
| ACTTTTAGAT | TAAAAAAATT | TTAAGTAWCT | AGGAGTATTT | AAATCCTTTT | CCCATAAATA | 2420 |
| AAAGTACAGT | TTTCTTGGTG | GCAGAATGAA | AATCAGCAAC | NTCTAGCATA | TAGACTATAT | 2480 |
| AATCAGATTG | ACAGCATATA | GAATATATTA | TCAGACAAGA | TGAGGAGGTA | CAAAAGTTAC | 2540 |

```
TATTGCTCAT AATGACTTAC AGGCTAAAAN TAGNTNTAAA ATACTATATT AAATTCTGAA    2600

TGCAATTTTT TTTTGTTCCC TTGAGACCAA AATTTAAGTT AACTGTTGCT GGCAGTCTAA    2660

GTGTAAATGT TAACAGCAGG AGAAGTTAAG AATTGAGCAG TTCTGTTGCA TGATTTCCCA    2720

AATGAAATAC TGCCTTGGCT AGAGTTTGAA AAACTAATTG AGCCTGTGCC TGGCTAGAAA    2780

ACAAGCGTTT ATTTGAATGT GAATAGTGTT TCAAAGGTAT GTAGTTACAG AATTCCTACC    2840

AAACAGCTTA AATTCTTCAA GAAAGAATTC CTGCAGCAGT TATTCCCTTA CCTGAAGGCT    2900

TCAATCATTT GGATCAACAA CTGCTACTCT CGGGAAGACT CCTCTACTCA CAGCTGAAGA    2960

AAATGAGCAC ACCCTTCACA CTGTTATCAC CTATCCTGAA GATGTGATAC ACTGAATGGA    3020

AATAAATAGA TGTAAATAAA ATTGAGWTCT CATTTAAAAA AAACCATGTG CCCAATGGGA    3080

AAATGACCTC ATGTTGTGGT TTAAACAGCA ACTGCACCCA CTAGCACAGC CCATTGAGCT    3140

ANCCTATATA TACATCTCTG TCAGTGCCCC TC                                  3172
```

( 2 ) INFORMATION FOR SEQ ID NO:4:

( i ) SEQUENCE CHARACTERISTICS:
        ( A ) LENGTH: 210 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Ala Val Ala Ala Pro Val Tyr Pro Ala Leu Gly Thr Ala Pro Gly Gly
 1               5                  10                  15

Glu Thr Val Pro Ala Met Ser Ala Ala Met Arg Glu Arg Phe Asp Arg
                20                  25                  30

Phe Leu His Glu Lys Asn Cys Met Thr Asp Leu Leu Ala Lys Leu Glu
            35                  40                  45

Ala Lys Thr Gly Val Asn Arg Ser Phe Ile Ala Leu Gly Val Ile Gly
        50                  55                  60

Leu Val Ala Leu Tyr Leu Val Phe Gly Tyr Gly Ala Ser Leu Leu Cys
65                  70                  75                  80

Asn Leu Ile Gly Phe Gly Tyr Pro Ala Tyr Ile Ser Ile Lys Ala Ile
                85                  90                  95

Glu Ser Pro Asn Lys Glu Asp Asp Thr Gln Trp Leu Thr Tyr Trp Val
                100                 105                 110

Val Tyr Gly Val Phe Ser Ile Ala Glu Phe Phe Ser Asp Ile Phe Leu
            115                 120                 125

Ser Trp Phe Pro Phe Tyr Tyr Met Leu Lys Cys Gly Phe Leu Leu Trp
        130                 135                 140

Cys Met Ala Pro Ser Pro Ser Asn Gly Ala Glu Leu Leu Tyr Lys Arg
145                 150                 155                 160

Ile Ile Arg Pro Phe Phe Leu Lys His Glu Ser Gln Met Asp Ser Val
                165                 170                 175

Val Lys Asp Leu Lys Asp Lys Ser Lys Glu Thr Ala Asp Ala Ile Thr
            180                 185                 190

Lys Glu Ala Lys Lys Ala Thr Val Asn Leu Leu Gly Glu Glu Lys Lys
        195                 200                 205

Ser Thr
    210
```

( 2 ) INFORMATION FOR SEQ ID NO:5:

5,691,454

71 72

-continued

```
( i ) SEQUENCE CHARACTERISTICS:
        ( A ) LENGTH: 434 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Homo sapiens ( v i i ) IMMEDIATE SOURCE:
        ( B ) CLONE: TB1

( x i ) SEQUENCE DESCRIPTION: SEQ ID NO:5:
```

| | | | | | | | | | | | | | | | |
|---|---|---|---|---|---|---|---|---|---|---|---|---|---|---|---|
| Val | Ala | Pro | Val | Val | Val | Gly | Ser | Gly | Arg | Ala | Pro | Arg | His | Pro | Ala |
| 1 | | | | 5 | | | | | 10 | | | | | 15 | |
| Pro | Ala | Ala | Met | His | Pro | Arg | Arg | Pro | Asp | Gly | Phe | Asp | Gly | Leu | Gly |
| | | | 20 | | | | 25 | | | | | 30 | | | |
| Tyr | Arg | Gly | Gly | Ala | Arg | Asp | Glu | Gln | Gly | Phe | Gly | Gly | Ala | Phe | Pro |
| | | 35 | | | | | 40 | | | | | 45 | | | |
| Ala | Arg | Ser | Phe | Ser | Thr | Gly | Ser | Asp | Leu | Gly | His | Trp | Val | Thr | Thr |
| | 50 | | | | | 55 | | | | | 60 | | | | |
| Pro | Pro | Asp | Ile | Pro | Gly | Ser | Arg | Asn | Leu | His | Trp | Gly | Glu | Lys | Ser |
| 65 | | | | | 70 | | | | | 75 | | | | | 80 |
| Pro | Pro | Tyr | Gly | Val | Pro | Thr | Thr | Ser | Thr | Pro | Tyr | Glu | Gly | Pro | Thr |
| | | | | 85 | | | | | 90 | | | | | 95 | |
| Glu | Glu | Pro | Phe | Ser | Ser | Gly | Gly | Gly | Ser | Val | Gln | Gly | Gln | Ser | |
| | | | 100 | | | | | 105 | | | | | 110 | | |
| Ser | Glu | Gln | Leu | Asn | Arg | Phe | Ala | Gly | Phe | Gly | Ile | Gly | Leu | Ala | Ser |
| | | 115 | | | | | 120 | | | | | 125 | | | |
| Leu | Phe | Thr | Glu | Asn | Val | Leu | Ala | His | Pro | Cys | Ile | Val | Leu | Arg | Arg |
| | 130 | | | | | 135 | | | | | 140 | | | | |
| Gln | Cys | Gln | Val | Asn | Tyr | His | Ala | Gln | His | Tyr | His | Leu | Thr | Pro | Phe |
| 145 | | | | | 150 | | | | | 155 | | | | | 160 |
| Thr | Val | Ile | Asn | Ile | Met | Tyr | Ser | Phe | Asn | Lys | Thr | Gln | Gly | Pro | Arg |
| | | | | 165 | | | | | 170 | | | | | 175 | |
| Ala | Leu | Trp | Lys | Gly | Met | Gly | Ser | Thr | Phe | Ile | Val | Gln | Gly | Val | Thr |
| | | | 180 | | | | | 185 | | | | | 190 | | |
| Leu | Gly | Ala | Glu | Gly | Ile | Ile | Ser | Glu | Phe | Thr | Pro | Leu | Pro | Arg | Glu |
| | | 195 | | | | | 200 | | | | | 205 | | | |
| Val | Leu | His | Lys | Trp | Ser | Pro | Lys | Gln | Ile | Gly | Glu | His | Leu | Leu | Leu |
| | 210 | | | | | 215 | | | | | 220 | | | | |
| Lys | Ser | Leu | Thr | Tyr | Val | Val | Ala | Met | Pro | Phe | Tyr | Ser | Ala | Ser | Leu |
| 225 | | | | | 230 | | | | | 235 | | | | | 240 |
| Ile | Glu | Thr | Val | Gln | Ser | Glu | Ile | Ile | Arg | Asp | Asn | Thr | Gly | Ile | Leu |
| | | | | 245 | | | | | 250 | | | | | 255 | |
| Glu | Cys | Val | Lys | Glu | Gly | Ile | Gly | Arg | Val | Ile | Gly | Met | Gly | Val | Pro |
| | | | 260 | | | | | 265 | | | | | 270 | | |
| His | Ser | Lys | Arg | Leu | Leu | Pro | Leu | Leu | Ser | Leu | Ile | Phe | Pro | Thr | Val |
| | | 275 | | | | | 280 | | | | | 285 | | | |
| Leu | His | Gly | Val | Leu | His | Tyr | Ile | Ile | Ser | Ser | Val | Ile | Gln | Lys | Phe |
| | 290 | | | | | 295 | | | | | 300 | | | | |
| Val | Leu | Leu | Ile | Leu | Lys | Arg | Lys | Thr | Tyr | Asn | Ser | His | Leu | Ala | Glu |
| 305 | | | | | 310 | | | | | 315 | | | | | 320 |
| Ser | Thr | Ser | Pro | Val | Gln | Ser | Met | Leu | Asp | Ala | Tyr | Phe | Pro | Glu | Leu |
| | | | | 325 | | | | | 330 | | | | | 335 | |
| Ile | Ala | Asn | Phe | Ala | Ala | Ser | Leu | Cys | Ser | Asp | Val | Ile | Leu | Tyr | Pro |

|         |     |     |     |     |     |     | 340 |     |     |     | 345 |     |     |     | 350 |     |     |
|---------|-----|-----|-----|-----|-----|-----|-----|-----|-----|-----|-----|-----|-----|-----|-----|-----|-----|

```
            340                           345                           350
Leu  Glu  Thr  Val  Leu  His  Arg  Leu  His  Ile  Gln  Gly  Thr  Arg  Thr  Ile
          355                           360                           365
Ile  Asp  Asn  Thr  Asp  Leu  Gly  Tyr  Glu  Val  Leu  Pro  Ile  Asn  Thr  Gln
          370                           375                           380
Tyr  Glu  Gly  Met  Arg  Asp  Cys  Ile  Asn  Thr  Ile  Arg  Gln  Glu  Glu  Gly
385                           390                           395                           400
Val  Phe  Gly  Phe  Tyr  Lys  Gly  Phe  Gly  Ala  Val  Ile  Ile  Gln  Tyr  Thr
                    405                           410                           415
Leu  His  Ala  Ala  Val  Leu  Gln  Ile  Thr  Lys  Ile  Ile  Tyr  Ser  Thr  Leu
                    420                           425                           430
Leu  Gln
```

( 2 ) INFORMATION FOR SEQ ID NO:6:

( i ) SEQUENCE CHARACTERISTICS:
( A ) LENGTH: 185 amino acids
( B ) TYPE: amino acid
( C ) STRANDEDNESS: single
( D ) TOPOLOGY: linear ( i i ) MOLECULE TYPE: protein ( v i ) ORIGINAL SOURCE:
( A ) ORGANISM: Homo sapiens ( v i i ) IMMEDIATE SOURCE:
( B ) CLONE: YS-39(TB2)

( x i ) SEQUENCE DESCRIPTION: SEQ ID NO:6:

```
Glu  Leu  Arg  Arg  Phe  Asp  Arg  Phe  Leu  His  Glu  Lys  Asn  Cys  Met  Thr
1                   5                           10                          15
Asp  Leu  Leu  Ala  Lys  Leu  Glu  Ala  Lys  Thr  Gly  Val  Asn  Arg  Ser  Phe
               20                           25                          30
Ile  Ala  Leu  Gly  Val  Ile  Gly  Leu  Val  Ala  Leu  Tyr  Leu  Val  Phe  Gly
               35                           40                          45
Tyr  Gly  Ala  Ser  Leu  Leu  Cys  Asn  Leu  Ile  Gly  Phe  Gly  Tyr  Pro  Ala
     50                           55                          60
Tyr  Ile  Ser  Ile  Lys  Ala  Ile  Glu  Ser  Pro  Asn  Lys  Glu  Asp  Asp  Thr
65                           70                          75                      80
Gln  Trp  Leu  Thr  Tyr  Trp  Val  Val  Tyr  Gly  Val  Phe  Ser  Ile  Ala  Glu
                    85                           90                          95
Phe  Phe  Ser  Asp  Ile  Phe  Leu  Ser  Trp  Phe  Pro  Phe  Tyr  Tyr  Ile  Leu
                    100                          105                         110
Lys  Cys  Gly  Phe  Leu  Leu  Trp  Cys  Met  Ala  Pro  Ser  Pro  Ser  Asn  Gly
               115                          120                         125
Ala  Glu  Leu  Leu  Tyr  Lys  Arg  Ile  Ile  Arg  Pro  Phe  Phe  Leu  Lys  His
     130                          135                         140
Glu  Ser  Gln  Met  Asp  Ser  Val  Val  Lys  Asp  Leu  Lys  Asp  Lys  Ala  Lys
145                          150                         155                      160
Glu  Thr  Ala  Asp  Ala  Ile  Thr  Lys  Glu  Ala  Lys  Lys  Ala  Thr  Val  Asn
                    165                          170                         175
Leu  Leu  Gly  Glu  Glu  Lys  Lys  Ser  Thr
                    180                          185
```

( 2 ) INFORMATION FOR SEQ ID NO:7:

( i ) SEQUENCE CHARACTERISTICS:
( A ) LENGTH: 2842 amino acids
( B ) TYPE: amino acid ( C ) STRANDEDNESS: single
( D ) TOPOLOGY: linear ( i i ) MOLECULE TYPE: protein ( v i ) ORIGINAL SOURCE:
    ( A ) ORGANISM: Homo sapiens ( v i i ) IMMEDIATE SOURCE:
    ( B ) CLONE: APC ( x i ) SEQUENCE DESCRIPTION: SEQ ID NO:7:

```
Met Ala Ala Ala Ser Tyr Asp Gln Leu Leu Lys Gln Val Glu Ala Leu
 1               5                  10                  15

Lys Met Glu Asn Ser Asn Leu Arg Gln Glu Leu Glu Asp Asn Ser Asn
            20                  25                  30

His Leu Thr Lys Leu Glu Thr Glu Ala Ser Asn Met Lys Glu Val Leu
        35                  40                  45

Lys Gln Leu Gln Gly Ser Ile Glu Asp Glu Ala Met Ala Ser Ser Gly
    50                  55                  60

Gln Ile Asp Leu Leu Glu Arg Leu Lys Glu Leu Asn Leu Asp Ser Ser
65                  70                  75                  80

Asn Phe Pro Gly Val Lys Leu Arg Ser Lys Met Ser Leu Arg Ser Tyr
                85                  90                  95

Gly Ser Arg Glu Gly Ser Val Ser Ser Arg Ser Gly Glu Cys Ser Pro
            100                 105                 110

Val Pro Met Gly Ser Phe Pro Arg Arg Gly Phe Val Asn Gly Ser Arg
        115                 120                 125

Glu Ser Thr Gly Tyr Leu Glu Glu Leu Glu Lys Glu Arg Ser Leu Leu
    130                 135                 140

Leu Ala Asp Leu Asp Lys Glu Glu Lys Glu Lys Asp Trp Tyr Tyr Ala
145                 150                 155                 160

Gln Leu Gln Asn Leu Thr Lys Arg Ile Asp Ser Leu Leu Thr Glu Asn
                165                 170                 175

Phe Ser Leu Gln Thr Asp Met Thr Arg Arg Gln Leu Glu Tyr Glu Ala
            180                 185                 190

Arg Gln Ile Arg Val Ala Met Glu Glu Gln Leu Gly Thr Cys Gln Asp
        195                 200                 205

Met Glu Lys Arg Ala Gln Arg Arg Ile Ala Arg Ile Gln Gln Ile Glu
    210                 215                 220

Lys Asp Ile Leu Arg Ile Arg Gln Leu Leu Gln Ser Gln Ala Thr Glu
225                 230                 235                 240

Ala Glu Arg Ser Ser Gln Asn Lys His Glu Thr Gly Ser His Asp Ala
                245                 250                 255

Glu Arg Gln Asn Glu Gly Gln Gly Val Gly Glu Ile Asn Met Ala Thr
            260                 265                 270

Ser Gly Asn Gly Gln Gly Ser Thr Thr Arg Met Asp His Glu Thr Ala
        275                 280                 285

Ser Val Leu Ser Ser Ser Ser Thr His Ser Ala Pro Arg Arg Leu Thr
    290                 295                 300

Ser His Leu Gly Thr Lys Val Glu Met Val Tyr Ser Leu Leu Ser Met
305                 310                 315                 320

Leu Gly Thr His Asp Lys Asp Asp Met Ser Arg Thr Leu Leu Ala Met
                325                 330                 335

Ser Ser Ser Gln Asp Ser Cys Ile Ser Met Arg Gln Ser Gly Cys Leu
            340                 345                 350

Pro Leu Leu Ile Gln Leu Leu His Gly Asn Asp Lys Asp Ser Val Leu
```

|     |     |     | 355 |     |     |     | 360 |     |     |     | 365 |     |     |     |
|-----|-----|-----|-----|-----|-----|-----|-----|-----|-----|-----|-----|-----|-----|-----|
| Leu | Gly | Asn | Ser | Arg | Gly | Ser | Lys | Glu | Ala | Arg | Ala | Arg | Ala | Ser | Ala |
|     |     |     | 370 |     |     |     | 375 |     |     |     | 380 |     |     |     |
| Ala | Leu | His | Asn | Ile | Ile | His | Ser | Gln | Pro | Asp | Asp | Lys | Arg | Gly | Arg |
| 385 |     |     |     |     | 390 |     |     |     |     | 395 |     |     |     |     | 400 |
| Arg | Glu | Ile | Arg | Val | Leu | His | Leu | Leu | Glu | Gln | Ile | Arg | Ala | Tyr | Cys |
|     |     |     |     | 405 |     |     |     |     | 410 |     |     |     |     | 415 |     |
| Glu | Thr | Cys | Trp | Glu | Trp | Gln | Glu | Ala | His | Glu | Pro | Gly | Met | Asp | Gln |
|     |     |     | 420 |     |     |     |     | 425 |     |     |     |     | 430 |     |     |
| Asp | Lys | Asn | Pro | Met | Pro | Ala | Pro | Val | Glu | His | Gln | Ile | Cys | Pro | Ala |
|     |     | 435 |     |     |     |     | 440 |     |     |     |     | 445 |     |     |     |
| Val | Cys | Val | Leu | Met | Lys | Leu | Ser | Phe | Asp | Glu | Glu | His | Arg | His | Ala |
|     | 450 |     |     |     |     | 455 |     |     |     |     | 460 |     |     |     |     |
| Met | Asn | Glu | Leu | Gly | Gly | Leu | Gln | Ala | Ile | Ala | Glu | Leu | Leu | Gln | Val |
| 465 |     |     |     |     | 470 |     |     |     |     | 475 |     |     |     |     | 480 |
| Asp | Cys | Glu | Met | Tyr | Gly | Leu | Thr | Asn | Asp | His | Tyr | Ser | Ile | Thr | Leu |
|     |     |     |     | 485 |     |     |     |     | 490 |     |     |     |     | 495 |     |
| Arg | Arg | Tyr | Ala | Gly | Met | Ala | Leu | Thr | Asn | Leu | Thr | Phe | Gly | Asp | Val |
|     |     |     | 500 |     |     |     |     | 505 |     |     |     |     | 510 |     |     |
| Ala | Asn | Lys | Ala | Thr | Leu | Cys | Ser | Met | Lys | Gly | Cys | Met | Arg | Ala | Leu |
|     |     | 515 |     |     |     |     | 520 |     |     |     |     | 525 |     |     |     |
| Val | Ala | Gln | Leu | Lys | Ser | Glu | Ser | Glu | Asp | Leu | Gln | Gln | Val | Ile | Ala |
|     | 530 |     |     |     |     | 535 |     |     |     |     | 540 |     |     |     |     |
| Ser | Val | Leu | Arg | Asn | Leu | Ser | Trp | Arg | Ala | Asp | Val | Asn | Ser | Lys | Lys |
| 545 |     |     |     |     | 550 |     |     |     |     | 555 |     |     |     |     | 560 |
| Thr | Leu | Arg | Glu | Val | Gly | Ser | Val | Lys | Ala | Leu | Met | Glu | Cys | Ala | Leu |
|     |     |     |     | 565 |     |     |     |     | 570 |     |     |     |     | 575 |     |
| Glu | Val | Lys | Lys | Glu | Ser | Thr | Leu | Lys | Ser | Val | Leu | Ser | Ala | Leu | Trp |
|     |     |     | 580 |     |     |     |     | 585 |     |     |     |     | 590 |     |     |
| Asn | Leu | Ser | Ala | His | Cys | Thr | Glu | Asn | Lys | Ala | Asp | Ile | Cys | Ala | Val |
|     |     | 595 |     |     |     |     | 600 |     |     |     |     | 605 |     |     |     |
| Asp | Gly | Ala | Leu | Ala | Phe | Leu | Val | Gly | Thr | Leu | Thr | Tyr | Arg | Ser | Gln |
|     | 610 |     |     |     |     | 615 |     |     |     |     | 620 |     |     |     |     |
| Thr | Asn | Thr | Leu | Ala | Ile | Ile | Glu | Ser | Gly | Gly | Gly | Ile | Leu | Arg | Asn |
| 625 |     |     |     |     | 630 |     |     |     |     | 635 |     |     |     |     | 640 |
| Val | Ser | Ser | Leu | Ile | Ala | Thr | Asn | Glu | Asp | His | Arg | Gln | Ile | Leu | Arg |
|     |     |     |     | 645 |     |     |     |     | 650 |     |     |     |     | 655 |     |
| Glu | Asn | Asn | Cys | Leu | Gln | Thr | Leu | Leu | Gln | His | Leu | Lys | Ser | His | Ser |
|     |     |     | 660 |     |     |     |     | 665 |     |     |     |     | 670 |     |     |
| Leu | Thr | Ile | Val | Ser | Asn | Ala | Cys | Gly | Thr | Leu | Trp | Asn | Leu | Ser | Ala |
|     |     | 675 |     |     |     |     | 680 |     |     |     |     | 685 |     |     |     |
| Arg | Asn | Pro | Lys | Asp | Gln | Glu | Ala | Leu | Trp | Asp | Met | Gly | Ala | Val | Ser |
|     | 690 |     |     |     |     | 695 |     |     |     |     | 700 |     |     |     |     |
| Met | Leu | Lys | Asn | Leu | Ile | His | Ser | Lys | His | Lys | Met | Ile | Ala | Met | Gly |
| 705 |     |     |     |     | 710 |     |     |     |     | 715 |     |     |     |     | 720 |
| Ser | Ala | Ala | Ala | Leu | Arg | Asn | Leu | Met | Ala | Asn | Arg | Pro | Ala | Lys | Tyr |
|     |     |     |     | 725 |     |     |     |     | 730 |     |     |     |     | 735 |     |
| Lys | Asp | Ala | Asn | Ile | Met | Ser | Pro | Gly | Ser | Ser | Leu | Pro | Ser | Leu | His |
|     |     |     | 740 |     |     |     |     | 745 |     |     |     |     | 750 |     |     |
| Val | Arg | Lys | Gln | Lys | Ala | Leu | Glu | Ala | Glu | Leu | Asp | Ala | Gln | His | Leu |
|     |     | 755 |     |     |     |     | 760 |     |     |     |     | 765 |     |     |     |
| Ser | Glu | Thr | Phe | Asp | Asn | Ile | Asp | Asn | Leu | Ser | Pro | Lys | Ala | Ser | His |
|     |     | 770 |     |     |     |     | 775 |     |     |     |     | 780 |     |     |     |

```
Arg  Ser  Lys  Gln  Arg  His  Lys  Gln  Ser  Leu  Tyr  Gly  Asp  Tyr  Val  Phe
785                 790                      795                           800

Asp  Thr  Asn  Arg  His  Asp  Asp  Asn  Arg  Ser  Asp  Asn  Phe  Asn  Thr  Gly
                    805                      810                 815

Asn  Met  Thr  Val  Leu  Ser  Pro  Tyr  Leu  Asn  Thr  Thr  Val  Leu  Pro  Ser
               820                      825                      830

Ser  Ser  Ser  Ser  Arg  Gly  Ser  Leu  Asp  Ser  Ser  Arg  Ser  Glu  Lys  Asp
               835                      840                 845

Arg  Ser  Leu  Glu  Arg  Glu  Arg  Gly  Ile  Gly  Leu  Gly  Asn  Tyr  His  Pro
850                      855                      860

Ala  Thr  Glu  Asn  Pro  Gly  Thr  Ser  Ser  Lys  Arg  Gly  Leu  Gln  Ile  Ser
865                 870                      875                           880

Thr  Thr  Ala  Ala  Gln  Ile  Ala  Lys  Val  Met  Glu  Glu  Val  Ser  Ala  Ile
               885                      890                           895

His  Thr  Ser  Gln  Glu  Asp  Arg  Ser  Ser  Gly  Ser  Thr  Thr  Glu  Leu  His
               900                      905                 910

Cys  Val  Thr  Asp  Glu  Arg  Asn  Ala  Leu  Arg  Arg  Ser  Ser  Ala  Ala  His
          915                      920                 925

Thr  His  Ser  Asn  Thr  Tyr  Asn  Phe  Thr  Lys  Ser  Glu  Asn  Ser  Asn  Arg
     930                      935                 940

Thr  Cys  Ser  Met  Pro  Tyr  Ala  Lys  Leu  Glu  Tyr  Lys  Arg  Ser  Ser  Asn
945                 950                      955                           960

Asp  Ser  Leu  Asn  Ser  Val  Ser  Ser  Asp  Gly  Tyr  Gly  Lys  Arg  Gly
                    965                      970                 975

Gln  Met  Lys  Pro  Ser  Ile  Glu  Ser  Tyr  Ser  Glu  Asp  Asp  Glu  Ser  Lys
               980                      985                 990

Phe  Cys  Ser  Tyr  Gly  Gln  Tyr  Pro  Ala  Asp  Leu  Ala  His  Lys  Ile  His
          995                      1000                1005

Ser  Ala  Asn  His  Met  Asp  Asp  Asn  Asp  Gly  Glu  Leu  Asp  Thr  Pro  Ile
     1010                     1015                     1020

Asn  Tyr  Ser  Leu  Lys  Tyr  Ser  Asp  Glu  Gln  Leu  Asn  Ser  Gly  Arg  Gln
1025                     1030                     1035                     1040

Ser  Pro  Ser  Gln  Asn  Glu  Arg  Trp  Ala  Arg  Pro  Lys  His  Ile  Ile  Glu
                    1045                     1050                     1055

Asp  Glu  Ile  Lys  Gln  Ser  Glu  Gln  Arg  Gln  Ser  Arg  Asn  Gln  Ser  Thr
               1060                     1065                     1070

Thr  Tyr  Pro  Val  Tyr  Thr  Glu  Ser  Thr  Asp  Asp  Lys  His  Leu  Lys  Phe
          1075                     1080                     1085

Gln  Pro  His  Phe  Gly  Gln  Gln  Glu  Cys  Val  Ser  Pro  Tyr  Arg  Ser  Arg
     1090                     1095                     1100

Gly  Ala  Asn  Gly  Ser  Glu  Thr  Asn  Arg  Val  Gly  Ser  Asn  His  Gly  Ile
1105                     1110                     1115                     1120

Asn  Gln  Asn  Val  Ser  Gln  Ser  Leu  Cys  Gln  Glu  Asp  Asp  Tyr  Glu  Asp
                    1125                     1130                     1135

Asp  Lys  Pro  Thr  Asn  Tyr  Ser  Glu  Arg  Tyr  Ser  Glu  Glu  Glu  Gln  His
               1140                     1145                     1150

Glu  Glu  Glu  Glu  Arg  Pro  Thr  Asn  Tyr  Ser  Ile  Lys  Tyr  Asn  Glu  Glu
          1155                     1160                     1165

Lys  Arg  His  Val  Asp  Gln  Pro  Ile  Asp  Tyr  Ser  Leu  Lys  Tyr  Ala  Thr
     1170                     1175                     1180

Asp  Ile  Pro  Ser  Ser  Gln  Lys  Gln  Ser  Phe  Ser  Phe  Ser  Lys  Ser  Ser
1185                     1190                     1195                     1200

Ser  Gly  Gln  Ser  Ser  Lys  Thr  Glu  His  Met  Ser  Ser  Ser  Ser  Glu  Asn
                    1205                     1210                     1215
```

```
Thr Ser Thr Pro Ser Ser Asn Ala Lys Arg Gln Asn Gln Leu His Pro
            1220                1225                1230
Ser Ser Ala Gln Ser Arg Ser Gly Gln Pro Gln Lys Ala Ala Thr Cys
        1235                1240                1245
Lys Val Ser Ser Ile Asn Gln Glu Thr Ile Gln Thr Tyr Cys Val Glu
    1250                1255                1260
Asp Thr Pro Ile Cys Phe Ser Arg Cys Ser Ser Leu Ser Ser Leu Ser
1265            1270                1275                1280
Ser Ala Glu Asp Glu Ile Gly Cys Asn Gln Thr Thr Gln Glu Ala Asp
                1285                1290                1295
Ser Ala Asn Thr Leu Gln Ile Ala Glu Ile Lys Glu Lys Ile Gly Thr
            1300                1305                1310
Arg Ser Ala Glu Asp Pro Val Ser Glu Val Pro Ala Val Ser Gln His
            1315                1320                1325
Pro Arg Thr Lys Ser Ser Arg Leu Gln Gly Ser Ser Leu Ser Ser Glu
        1330                1335                1340
Ser Ala Arg His Lys Ala Val Glu Phe Ser Ser Gly Ala Lys Ser Pro
1345            1350                1355                1360
Ser Lys Ser Gly Ala Gln Thr Pro Lys Ser Pro Pro Glu His Tyr Val
            1365                1370                1375
Gln Glu Thr Pro Leu Met Phe Ser Arg Cys Thr Ser Val Ser Ser Leu
            1380                1385                1390
Asp Ser Phe Glu Ser Arg Ser Ile Ala Ser Ser Val Gln Ser Glu Pro
            1395                1400                1405
Cys Ser Gly Met Val Ser Gly Ile Ile Ser Pro Ser Asp Leu Pro Asp
    1410                1415                1420
Ser Pro Gly Gln Thr Met Pro Pro Ser Arg Ser Lys Thr Pro Pro Pro
1425            1430                1435                1440
Pro Pro Gln Thr Ala Gln Thr Lys Arg Glu Val Pro Lys Asn Lys Ala
            1445                1450                1455
Pro Thr Ala Glu Lys Arg Glu Ser Gly Pro Lys Gln Ala Ala Val Asn
            1460                1465                1470
Ala Ala Val Gln Arg Val Gln Val Leu Pro Asp Ala Asp Thr Leu Leu
        1475                1480                1485
His Phe Ala Thr Glu Ser Thr Pro Asp Gly Phe Ser Cys Ser Ser Ser
        1490                1495                1500
Leu Ser Ala Leu Ser Leu Asp Glu Pro Phe Ile Gln Lys Asp Val Glu
1505            1510                1515                1520
Leu Arg Ile Met Pro Pro Val Gln Glu Asn Asp Asn Gly Asn Glu Thr
                1525                1530                1535
Glu Ser Glu Gln Pro Lys Glu Ser Asn Glu Asn Gln Glu Lys Glu Ala
            1540                1545                1550
Glu Lys Thr Ile Asp Ser Glu Lys Asp Leu Leu Asp Asp Ser Asp Asp
        1555                1560                1565
Asp Asp Ile Glu Ile Leu Glu Glu Cys Ile Ile Ser Ala Met Pro Thr
        1570                1575                1580
Lys Ser Ser Arg Lys Ala Lys Lys Pro Ala Gln Thr Ala Ser Lys Leu
1585            1590                1595                1600
Pro Pro Pro Val Ala Arg Lys Pro Ser Gln Leu Pro Val Tyr Lys Leu
            1605                1610                1615
Leu Pro Ser Gln Asn Arg Leu Gln Pro Gln Lys His Val Ser Phe Thr
        1620                1625                1630
Pro Gly Asp Asp Met Pro Arg Val Tyr Cys Val Glu Gly Thr Pro Ile
```

-continued

```
                   1635                    1640                    1645
Asn  Phe  Ser  Thr  Ala  Thr  Ser  Leu  Ser  Asp  Leu  Thr  Ile  Glu  Ser  Pro
          1650                    1655                    1660
Pro  Asn  Glu  Leu  Ala  Ala  Gly  Glu  Gly  Val  Arg  Gly  Gly  Ala  Gln  Ser
1665                    1670                    1675                    1680
Gly  Glu  Phe  Glu  Lys  Arg  Asp  Thr  Ile  Pro  Thr  Glu  Gly  Arg  Ser  Thr
               1685                    1690                    1695
Asp  Glu  Ala  Gln  Gly  Gly  Lys  Thr  Ser  Ser  Val  Thr  Ile  Pro  Glu  Leu
          1700                    1705                    1710
Asp  Asp  Asn  Lys  Ala  Glu  Glu  Gly  Asp  Ile  Leu  Ala  Glu  Cys  Ile  Asn
          1715                    1720                    1725
Ser  Ala  Met  Pro  Lys  Gly  Lys  Ser  His  Lys  Pro  Phe  Arg  Val  Lys  Lys
          1730                    1735                    1740
Ile  Met  Asp  Gln  Val  Gln  Gln  Ala  Ser  Ala  Ser  Ser  Ser  Ala  Pro  Asn
1745                    1750                    1755                    1760
Lys  Asn  Gln  Leu  Asp  Gly  Lys  Lys  Lys  Lys  Pro  Thr  Ser  Pro  Val  Lys
               1765                    1770                    1775
Pro  Ile  Pro  Gln  Asn  Thr  Glu  Tyr  Arg  Thr  Arg  Val  Arg  Lys  Asn  Ala
               1780                    1785                    1790
Asp  Ser  Lys  Asn  Asn  Leu  Asn  Ala  Glu  Arg  Val  Phe  Ser  Asp  Asn  Lys
          1795                    1800                    1805
Asp  Ser  Lys  Lys  Gln  Asn  Leu  Lys  Asn  Asn  Ser  Lys  Asp  Phe  Asn  Asp
          1810                    1815                    1820
Lys  Leu  Pro  Asn  Asn  Glu  Asp  Arg  Val  Arg  Gly  Ser  Phe  Ala  Phe  Asp
1825                    1830                    1835                    1840
Ser  Pro  His  His  Tyr  Thr  Pro  Ile  Glu  Gly  Thr  Pro  Tyr  Cys  Phe  Ser
               1845                    1850                    1855
Arg  Asn  Asp  Ser  Leu  Ser  Ser  Leu  Asp  Phe  Asp  Asp  Asp  Asp  Val  Asp
               1860                    1865                    1870
Leu  Ser  Arg  Glu  Lys  Ala  Glu  Leu  Arg  Lys  Ala  Lys  Glu  Asn  Lys  Glu
          1875                    1880                    1885
Ser  Glu  Ala  Lys  Val  Thr  Ser  His  Thr  Glu  Leu  Thr  Ser  Asn  Gln  Gln
          1890                    1895                    1900
Ser  Ala  Asn  Lys  Thr  Gln  Ala  Ile  Ala  Lys  Gln  Pro  Ile  Asn  Arg  Gly
1905                    1910                    1915                    1920
Gln  Pro  Lys  Pro  Ile  Leu  Gln  Lys  Gln  Ser  Thr  Phe  Pro  Gln  Ser  Ser
               1925                    1930                    1935
Lys  Asp  Ile  Pro  Asp  Arg  Gly  Ala  Ala  Thr  Asp  Glu  Lys  Leu  Gln  Asn
               1940                    1945                    1950
Phe  Ala  Ile  Glu  Asn  Thr  Pro  Val  Cys  Phe  Ser  His  Asn  Ser  Ser  Leu
          1955                    1960                    1965
Ser  Ser  Leu  Ser  Asp  Ile  Asp  Gln  Glu  Asn  Asn  Asn  Lys  Glu  Asn  Glu
          1970                    1975                    1980
Pro  Ile  Lys  Glu  Thr  Glu  Pro  Pro  Asp  Ser  Gln  Gly  Glu  Pro  Ser  Lys
1985                    1990                    1995                    2000
Pro  Gln  Ala  Ser  Gly  Tyr  Ala  Pro  Lys  Ser  Phe  His  Val  Glu  Asp  Thr
               2005                    2010                    2015
Pro  Val  Cys  Phe  Ser  Arg  Asn  Ser  Ser  Leu  Ser  Ser  Leu  Ser  Ile  Asp
               2020                    2025                    2030
Ser  Glu  Asp  Asp  Leu  Leu  Gln  Glu  Cys  Ile  Ser  Ser  Ala  Met  Pro  Lys
          2035                    2040                    2045
Lys  Lys  Lys  Pro  Ser  Arg  Leu  Lys  Gly  Asp  Asn  Glu  Lys  His  Ser  Pro
          2050                    2055                    2060
```

```
Arg  Asn  Met  Gly  Gly  Ile  Leu  Gly  Glu  Asp  Leu  Thr  Leu  Asp  Leu  Lys
2065                2070                2075                2080

Asp  Ile  Gln  Arg  Pro  Asp  Ser  Glu  His  Gly  Leu  Ser  Pro  Asp  Ser  Glu
          2085                2090                          2095

Asn  Phe  Asp  Trp  Lys  Ala  Ile  Gln  Glu  Gly  Ala  Asn  Ser  Ile  Val  Ser
               2100                2105                     2110

Ser  Leu  His  Gln  Ala  Ala  Ala  Ala  Ala  Cys  Leu  Ser  Arg  Gln  Ala  Ser
          2115                2120                          2125

Ser  Asp  Ser  Asp  Ser  Ile  Leu  Ser  Leu  Lys  Ser  Gly  Ile  Ser  Leu  Gly
          2130                2135                          2140

Ser  Pro  Phe  His  Leu  Thr  Pro  Asp  Gln  Glu  Glu  Lys  Pro  Phe  Thr  Ser
2145                2150                2155                2160

Asn  Lys  Gly  Pro  Arg  Ile  Leu  Lys  Pro  Gly  Glu  Lys  Ser  Thr  Leu  Glu
               2165                2170                     2175

Thr  Lys  Lys  Ile  Glu  Ser  Glu  Ser  Lys  Gly  Ile  Lys  Gly  Gly  Lys  Lys
               2180                2185                     2190

Val  Tyr  Lys  Ser  Leu  Ile  Thr  Gly  Lys  Val  Arg  Ser  Asn  Ser  Glu  Ile
               2195                2200                     2205

Ser  Gly  Gln  Met  Lys  Gln  Pro  Leu  Gln  Ala  Asn  Met  Pro  Ser  Ile  Ser
          2210                2215                          2220

Arg  Gly  Arg  Thr  Met  Ile  His  Ile  Pro  Gly  Val  Arg  Asn  Ser  Ser  Ser
2225                2230                2235                2240

Ser  Thr  Ser  Pro  Val  Ser  Lys  Lys  Gly  Pro  Pro  Leu  Lys  Thr  Pro  Ala
               2245                2250                     2255

Ser  Lys  Ser  Pro  Ser  Glu  Gly  Gln  Thr  Ala  Thr  Thr  Ser  Pro  Arg  Gly
               2260                2265                     2270

Ala  Lys  Pro  Ser  Val  Lys  Ser  Glu  Leu  Ser  Pro  Val  Ala  Arg  Gln  Thr
          2275                2280                          2285

Ser  Gln  Ile  Gly  Gly  Ser  Ser  Lys  Ala  Pro  Ser  Arg  Ser  Gly  Ser  Arg
          2290                2295                          2300

Asp  Ser  Thr  Pro  Ser  Arg  Pro  Ala  Gln  Gln  Pro  Leu  Ser  Arg  Pro  Ile
2305                2310                2315                2320

Gln  Ser  Pro  Gly  Arg  Asn  Ser  Ile  Ser  Pro  Gly  Arg  Asn  Gly  Ile  Ser
               2325                2330                     2335

Pro  Pro  Asn  Lys  Leu  Ser  Gln  Leu  Pro  Arg  Thr  Ser  Ser  Pro  Ser  Thr
               2340                2345                     2350

Ala  Ser  Thr  Lys  Ser  Ser  Gly  Ser  Gly  Lys  Met  Ser  Tyr  Thr  Ser  Pro
               2355                2360                     2365

Gly  Arg  Gln  Met  Ser  Gln  Gln  Asn  Leu  Thr  Lys  Gln  Thr  Gly  Leu  Ser
               2370                2375                     2380

Lys  Asn  Ala  Ser  Ser  Ile  Pro  Arg  Ser  Glu  Ser  Ala  Ser  Lys  Gly  Leu
2385                2390                2395                2400

Asn  Gln  Met  Asn  Asn  Gly  Asn  Gly  Ala  Asn  Lys  Lys  Val  Glu  Leu  Ser
                    2405                2410                2415

Arg  Met  Ser  Ser  Thr  Lys  Ser  Ser  Gly  Ser  Glu  Ser  Asp  Arg  Ser  Glu
               2420                2425                     2430

Arg  Pro  Val  Leu  Val  Arg  Gln  Ser  Thr  Phe  Ile  Lys  Glu  Ala  Pro  Ser
          2435                2440                          2445

Pro  Thr  Leu  Arg  Arg  Lys  Leu  Glu  Glu  Ser  Ala  Ser  Phe  Glu  Ser  Leu
          2450                2455                          2460

Ser  Pro  Ser  Ser  Arg  Pro  Ala  Ser  Pro  Thr  Arg  Ser  Gln  Ala  Gln  Thr
2465                2470                2475                2480

Pro  Val  Leu  Ser  Pro  Ser  Leu  Pro  Asp  Met  Ser  Leu  Ser  Thr  His  Ser
               2485                2490                     2495
```

-continued

```
Ser  Val  Gln  Ala  Gly  Gly  Trp  Arg  Lys  Leu  Pro  Pro  Asn  Leu  Ser  Pro
               2500                    2505                         2510

Thr  Ile  Glu  Tyr  Asn  Asp  Gly  Arg  Pro  Ala  Lys  Arg  His  Asp  Ile  Ala
               2515                    2520                         2525

Arg  Ser  His  Ser  Glu  Ser  Pro  Ser  Arg  Leu  Pro  Ile  Asn  Arg  Ser  Gly
          2530                    2535                    2540

Thr  Trp  Lys  Arg  Glu  His  Ser  Lys  His  Ser  Ser  Leu  Pro  Arg  Val
2545                     2550                    2555                    2560

Ser  Thr  Trp  Arg  Arg  Thr  Gly  Ser  Ser  Ser  Ser  Ile  Leu  Ser  Ala  Ser
                    2565                    2570                         2575

Ser  Glu  Ser  Ser  Glu  Lys  Ala  Lys  Ser  Glu  Asp  Glu  Lys  His  Val  Asn
               2580                    2585                         2590

Ser  Ile  Ser  Gly  Thr  Lys  Gln  Ser  Lys  Glu  Asn  Gln  Val  Ser  Ala  Lys
               2595                    2600                         2605

Gly  Thr  Trp  Arg  Lys  Ile  Lys  Glu  Asn  Glu  Phe  Ser  Pro  Thr  Asn  Ser
          2610                    2615                    2620

Thr  Ser  Gln  Thr  Val  Ser  Ser  Gly  Ala  Thr  Asn  Gly  Ala  Glu  Ser  Lys
2625                     2630                    2635                    2640

Thr  Leu  Ile  Tyr  Gln  Met  Ala  Pro  Ala  Val  Ser  Lys  Thr  Glu  Asp  Val
               2645                    2650                         2655

Trp  Val  Arg  Ile  Glu  Asp  Cys  Pro  Ile  Asn  Asn  Pro  Arg  Ser  Gly  Arg
               2660                    2665                         2670

Ser  Pro  Thr  Gly  Asn  Thr  Pro  Pro  Val  Ile  Asp  Ser  Val  Ser  Glu  Lys
          2675                    2680                    2685

Ala  Asn  Pro  Asn  Ile  Lys  Asp  Ser  Lys  Asp  Asn  Gln  Ala  Lys  Gln  Asn
          2690                    2695                    2700

Val  Gly  Asn  Gly  Ser  Val  Pro  Met  Arg  Thr  Val  Gly  Leu  Glu  Asn  Arg
2705                     2710                    2715                    2720

Leu  Asn  Ser  Phe  Ile  Gln  Val  Asp  Ala  Pro  Asp  Gln  Lys  Gly  Thr  Glu
                    2725                    2730                         2735

Ile  Lys  Pro  Gly  Gln  Asn  Asn  Pro  Val  Pro  Val  Ser  Glu  Thr  Asn  Glu
               2740                    2745                         2750

Ser  Ser  Ile  Val  Glu  Arg  Thr  Pro  Phe  Ser  Ser  Ser  Ser  Ser  Ser  Lys
          2755                    2760                    2765

His  Ser  Ser  Pro  Ser  Gly  Thr  Val  Ala  Ala  Arg  Val  Thr  Pro  Phe  Asn
     2770                    2775                    2780

Tyr  Asn  Pro  Ser  Pro  Arg  Lys  Ser  Ser  Ala  Asp  Ser  Thr  Ser  Ala  Arg
2785                     2790                    2795                    2800

Pro  Ser  Gln  Ile  Pro  Thr  Pro  Val  Asn  Asn  Asn  Thr  Lys  Lys  Arg  Asp
               2805                    2810                         2815

Ser  Lys  Thr  Asp  Ser  Thr  Glu  Ser  Ser  Gly  Thr  Gln  Ser  Pro  Lys  Arg
               2820                    2825                         2830

His  Ser  Gly  Ser  Tyr  Leu  Val  Thr  Ser  Val
     2835                    2840
```

( 2 ) INFORMATION FOR SEQ ID NO:8:

( i ) SEQUENCE CHARACTERISTICS:
      ( A ) LENGTH: 31 amino acids
      ( B ) TYPE: amino acid
      ( C ) STRANDEDNESS: single
      ( D ) TOPOLOGY: linear ( i i ) MOLECULE TYPE: peptide ( v i i ) IMMEDIATE SOURCE:
      ( B ) CLONE: ral2(yeast)

(x i) SEQUENCE DESCRIPTION: SEQ ID NO:8:

```
Leu  Thr  Gly  Ala  Lys  Gly  Leu  Gln  Leu  Arg  Ala  Leu  Arg  Arg  Ile  Ala
1                   5                        10                            15

Arg  Ile  Glu  Gln  Gly  Gly  Thr  Ala  Ile  Ser  Pro  Thr  Ser  Pro  Leu
              20                        25                       30
```

(2) INFORMATION FOR SEQ ID NO:9:

(i) SEQUENCE CHARACTERISTICS:
        (A) LENGTH: 29 amino acids
        (B) TYPE: amino acid
        (C) STRANDEDNESS: single
        (D) TOPOLOGY: linear (i i) MOLECULE TYPE: peptide (v i) ORIGINAL SOURCE:
        (A) ORGANISM: Homo sapiens (v i i) IMMEDIATE SOURCE:
        (B) CLONE: m3(mAChR)

(x i) SEQUENCE DESCRIPTION: SEQ ID NO:9:

```
Leu  Tyr  Trp  Arg  Ile  Tyr  Lys  Glu  Thr  Glu  Lys  Arg  Thr  Lys  Glu  Leu
1                   5                        10                            15

Ala  Gly  Leu  Gln  Ala  Ser  Gly  Thr  Glu  Ala  Glu  Thr  Glu
              20                        25
```

(2) INFORMATION FOR SEQ ID NO:10:

(i) SEQUENCE CHARACTERISTICS:
        (A) LENGTH: 29 amino acids
        (B) TYPE: amino acid
        (C) STRANDEDNESS: single
        (D) TOPOLOGY: linear (i i) MOLECULE TYPE: peptide (v i) ORIGINAL SOURCE:
        (A) ORGANISM: Homo sapiens (v i i) IMMEDIATE SOURCE:
        (B) CLONE: MCC (x i) SEQUENCE DESCRIPTION: SEQ ID NO:10:

```
Leu  Tyr  Pro  Asn  Leu  Ala  Glu  Glu  Arg  Ser  Arg  Trp  Glu  Lys  Glu  Leu
1                   5                        10                            15

Ala  Gly  Leu  Arg  Glu  Glu  Asn  Glu  Ser  Leu  Thr  Ala  Met
              20                        25
```

(2) INFORMATION FOR SEQ ID NO:11:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Homo sapiens (x i) SEQUENCE DESCRIPTION: SEQ ID NO:11:

GTATCAAGAC TGTGACTTTT AATTGTAGTT TATCCATTTT 40

(2) INFORMATION FOR SEQ ID NO:12:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( i i ) MOLECULE TYPE: cDNA ( v i ) ORIGINAL SOURCE:
  ( A ) ORGANISM: Homo sapiens ( x i ) SEQUENCE DESCRIPTION: SEQ ID NO:12:

TTTAGAATTT CATGTTAATA TATTGTGTTC TTTTTAACAG 40

( 2 ) INFORMATION FOR SEQ ID NO:13:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:13:

GTAGATTTTA AAAAGGTGTT TTAAAATAAT TTTTTAAGCT 40

( 2 ) INFORMATION FOR SEQ ID NO:14:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:14:

AAGCAATTGT TGTATAAAAA CTTGTTTCTA TTTTATTTAG 40

( 2 ) INFORMATION FOR SEQ ID NO:15:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:15:

GTAACTTTTC TTCATATAGT AAACATTGCC TTGTGTACTC 40

( 2 ) INFORMATION FOR SEQ ID NO:16:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
  ( A ) ORGANISM: Homo sapiens ( x i ) SEQUENCE DESCRIPTION: SEQ ID NO:16:

NNNNNNNNNN NNNGTCCCTT TTTTAAAAA AAAAAAATAG    40

( 2 ) INFORMATION FOR SEQ ID NO:17:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:17:

GTAAGTAACT TGGCAGTACA ACTTATTTGA AACTTTAATA    40

( 2 ) INFORMATION FOR SEQ ID NO:18:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:18:

ATACAAGATA TTGATACTTT TTTATTATTT GTGGTTTTAG    40

( 2 ) INFORMATION FOR SEQ ID NO:19:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:19:

GTAAGTTACT TGTTTCTAAG TGATAAAACA G Y GAAGAGCT    40

( 2 ) INFORMATION FOR SEQ ID NO:20:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:20:

AATAAAAACA TAACTAATTA GGTTTCTTGT TTTATTTTAG    40

( 2 ) INFORMATION FOR SEQ ID NO:21:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:21:

```
GTTAGTAAAT TSCCTTTTTT GTTTGTGGGT ATAAAAATAG                              40
```

( 2 ) INFORMATION FOR SEQ ID NO:22:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:22:

```
ACCATTTTTG CATGTACTGA TGTTAACTCC ATCTTAACAG                              40
```

( 2 ) INFORMATION FOR SEQ ID NO:23:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:23:

```
GTAAATAAAT TATTTTATCA TATTTTTTAA AATTATTTAA                              40
```

( 2 ) INFORMATION FOR SEQ ID NO:24:

( i ) SEQUENCE CHARACTERISTICS:
    ( A ) LENGTH: 64 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:24:

```
CATGATGTTA TCTGTATTTA CCTATAGTCT AAATTATACC ATCTATAATG TGCTTAATTT        60
TTAG                                                                    64
```

( 2 ) INFORMATION FOR SEQ ID NO:25:

( i ) SEQUENCE CHARACTERISTICS:
    ( A ) LENGTH: 52 base pairs
    ( B ) TYPE: nucleic acid
    ( C ) STRANDEDNESS: single ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:25:

GTAACAGAAG ATTACAAACC CTGGTCACTA ATGCCATGAC TACTTTGCTA AG  52

( 2 ) INFORMATION FOR SEQ ID NO:26:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:26:

GGATATTAAA GTCGTAATTT TGTTTCTAAA CTCATTGGC CCACAG  46

( 2 ) INFORMATION FOR SEQ ID NO:27:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:27:

GTATGTTCTC TATAGTGTAC ATCGTAGTGC ATGTTTCAAA  40

( 2 ) INFORMATION FOR SEQ ID NO:28:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:28:

CATCATTGCT CTTCAAATAA CAAAGCATTA TGGTTTATGT TGATTTATT TTTCAG  56

( 2 ) INFORMATION FOR SEQ ID NO:29:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:29:

```
GTAAGACAAA AATGTTTTTT AATGACATAG ACAATTACTG GTG                                43
```

( 2 ) INFORMATION FOR SEQ ID NO:30:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:30:

```
TTAGATGATT GTCTTTTCC TCTTGCCCTT TTTAAATTAG                                     40
```

( 2 ) INFORMATION FOR SEQ ID NO:31:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:31:

```
GTATGTTTTT ATAACATGTA TTTCTTAAGA TAGCTCAGGT ATGA                               44
```

( 2 ) INFORMATION FOR SEQ ID NO:32:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:32:

```
GCTTGGCTTC AAGTTGNCTT TTTAATGATC CTCTATTCTG TATTTAATTT ACAG                    54
```

( 2 ) INFORMATION FOR SEQ ID NO:33:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:33:

```
GTACTATTTA GAATTTCACC TGTTTTTCTT TTTTCTCTTT TTCTTGAGG CAGGGTCTCA               60
CTCTG                                                                          65
```

( 2 ) INFORMATION FOR SEQ ID NO:34:

(i) SEQUENCE CHARACTERISTICS:
    (A) LENGTH: 52 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:34:

GCAACTAGTA TGATTTTATG TATAAATTAA TCTAAAATTG ATTAATTTCC AG    52

(2) INFORMATION FOR SEQ ID NO:35:

(i) SEQUENCE CHARACTERISTICS:
    (A) LENGTH: 42 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:35:

GTACCTTTGA AAACATTTAG TACTATAATA TGAATTTCAT GT    42

(2) INFORMATION FOR SEQ ID NO:36:

(i) SEQUENCE CHARACTERISTICS:
    (A) LENGTH: 40 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:36:

CCAACTCNAA TTAGATGACC CATATTCAGA AACTTACTAG    40

(2) INFORMATION FOR SEQ ID NO:37:

(i) SEQUENCE CHARACTERISTICS:
    (A) LENGTH: 54 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:37:

GTATATATAG AGTTTTATAT TACTTTTAAA GTACAGAATT CATACTCTCA AAAA    54

(2) INFORMATION FOR SEQ ID NO:38:

(i) SEQUENCE CHARACTERISTICS:
    (A) LENGTH: 41 base pairs
    (B) TYPE: nucleic acid
    (C) STRANDEDNESS: single
    (D) TOPOLOGY: linear (ii) MOLECULE TYPE: cDNA ( v i ) ORIGINAL SOURCE:
    ( A ) ORGANISM: Homo sapiens ( x i ) SEQUENCE DESCRIPTION: SEQ ID NO:38:

ATTGTGACCT TAATTTTGTG ATCTCTTGAT TTTTATTTCA G    41

( 2 ) INFORMATION FOR SEQ ID NO:39:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:39:

TCCCCGCCTG CCGCTCTC    18

( 2 ) INFORMATION FOR SEQ ID NO:40:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:40:

GCAGCGGCGG CTCCCGTG    18

( 2 ) INFORMATION FOR SEQ ID NO:41:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:41:

GTGAACGGCT CTCATGCTGC    20

( 2 ) INFORMATION FOR SEQ ID NO:42:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:42:

ACGTGCGGGG AGGAATGGA    19

( 2 ) INFORMATION FOR SEQ ID NO:43:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:43:

ATGATATCTT ACCAAATGAT ATAC    24

( 2 ) INFORMATION FOR SEQ ID NO:44:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:44:

TTATTCCTAC TTCTTCTATA CAG    23

( 2 ) INFORMATION FOR SEQ ID NO:45:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:45:

TACCCATGCT GGCTCTTTTT C    21

( 2 ) INFORMATION FOR SEQ ID NO:46:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:46:

TGGGGCCATC TTGTTCCTGA    20

( 2 ) INFORMATION FOR SEQ ID NO:47:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
                   ( A ) ORGANISM: Homo sapiens ( x i ) SEQUENCE DESCRIPTION: SEQ ID NO:47:

ACATTAGGCA CAAAGCTTGC AA                                                                          22

( 2 ) INFORMATION FOR SEQ ID NO:48:

( i ) SEQUENCE CHARACTERISTICS:
                   ( A ) LENGTH: 22 base pairs
                   ( B ) TYPE: nucleic acid
                   ( C ) STRANDEDNESS: single
                   ( D ) TOPOLOGY: linear ( i i ) MOLECULE TYPE: cDNA ( v i ) ORIGINAL SOURCE:
                   ( A ) ORGANISM: Homo sapiens ( x i ) SEQUENCE DESCRIPTION: SEQ ID NO:48:

ATCAAGCTCC AGTAAGAAGG TA                                                                          22

( 2 ) INFORMATION FOR SEQ ID NO:49:

( i ) SEQUENCE CHARACTERISTICS:
                   ( A ) LENGTH: 19 base pairs
                   ( B ) TYPE: nucleic acid
                   ( C ) STRANDEDNESS: single
                   ( D ) TOPOLOGY: linear ( i i ) MOLECULE TYPE: cDNA ( v i ) ORIGINAL SOURCE:
                   ( A ) ORGANISM: Homo sapiens ( x i ) SEQUENCE DESCRIPTION: SEQ ID NO:49:

TGCGGCTCCT GGGTTGTTG                                                                              19

( 2 ) INFORMATION FOR SEQ ID NO:50:

( i ) SEQUENCE CHARACTERISTICS:
                   ( A ) LENGTH: 20 base pairs
                   ( B ) TYPE: nucleic acid
                   ( C ) STRANDEDNESS: single
                   ( D ) TOPOLOGY: linear ( i i ) MOLECULE TYPE: cDNA ( v i ) ORIGINAL SOURCE:
                   ( A ) ORGANISM: Homo sapiens ( x i ) SEQUENCE DESCRIPTION: SEQ ID NO:50:

GCCCCTTCCT TTCTGAGGAC                                                                             20

( 2 ) INFORMATION FOR SEQ ID NO:51:

( i ) SEQUENCE CHARACTERISTICS:
                   ( A ) LENGTH: 21 base pairs
                   ( B ) TYPE: nucleic acid
                   ( C ) STRANDEDNESS: single
                   ( D ) TOPOLOGY: linear ( i i ) MOLECULE TYPE: cDNA ( v i ) ORIGINAL SOURCE:
                   ( A ) ORGANISM: Homo sapiens ( x i ) SEQUENCE DESCRIPTION: SEQ ID NO:51:

TTTTCTCCTG CCTCTTACTG C                                                                           21

( 2 ) INFORMATION FOR SEQ ID NO:52:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:52:

ATGACACCCC CCATTCCCTC　　　　　　　　　　　　　　　　　　　　　　20

( 2 ) INFORMATION FOR SEQ ID NO:53:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:53:

CCACTTAAAG CACATATATT TAGT　　　　　　　　　　　　　　　　　　　　24

( 2 ) INFORMATION FOR SEQ ID NO:54:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:54:

GTATGGAAAA TAGTGAAGAA CC　　　　　　　　　　　　　　　　　　　　　22

( 2 ) INFORMATION FOR SEQ ID NO:55:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:55:

TTCTTAAGTC CTGTTTTTCT TTTG　　　　　　　　　　　　　　　　　　　　24

( 2 ) INFORMATION FOR SEQ ID NO:56:

( i ) SEQUENCE CHARACTERISTICS:
        ( A ) LENGTH: 23 base pairs
        ( B ) TYPE: nucleic acid
        ( C ) STRANDEDNESS: single (D) TOPOLOGY: linear (ii) MOLECULE TYPE: cDNA (vi) ORIGINAL SOURCE:
  (A) ORGANISM: Homo sapiens (xi) SEQUENCE DESCRIPTION: SEQ ID NO:56:

TTTAGAACCT TTTTGTGTT GTG  23

(2) INFORMATION FOR SEQ ID NO:57:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:57:

CTCAGATTAT ACACTAAGCC TAAC  24

(2) INFORMATION FOR SEQ ID NO:58:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:58:

CATGTCTCTT ACAGTAGTAC CA  22

(2) INFORMATION FOR SEQ ID NO:59:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:59:

AGGTCCAAGG GTAGCCAAGG  20

(2) INFORMATION FOR SEQ ID NO:60:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:60:

TAAAAATGGA TAAACTACAA TTAAAAG 27

( 2 ) INFORMATION FOR SEQ ID NO:61:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:61:

AAATACAGAA TCATGTCTTG AAGT 24

( 2 ) INFORMATION FOR SEQ ID NO:62:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:62:

ACACCTAAAG ATGACAATTT GAG 23

( 2 ) INFORMATION FOR SEQ ID NO:63:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:63:

TAACTTAGAT AGCAGTAATT TCCC 24

( 2 ) INFORMATION FOR SEQ ID NO:64:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:64:

ACAATAAACT GGAGTACACA AGG 23

( 2 ) INFORMATION FOR SEQ ID NO:65:

( i ) SEQUENCE CHARACTERISTICS:
        ( A ) LENGTH: 23 base pairs ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( x i ) SEQUENCE DESCRIPTION: SEQ ID NO:65:

ATAGGTCATT GCTTCTTGCT GAT 23

( 2 ) INFORMATION FOR SEQ ID NO:66:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( x i ) SEQUENCE DESCRIPTION: SEQ ID NO:66:

TGAATTTTAA TGGATTACCT AGGT 24

( 2 ) INFORMATION FOR SEQ ID NO:67:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( x i ) SEQUENCE DESCRIPTION: SEQ ID NO:67:

CTTTTTTTGC TTTTACTGAT TAACG 25

( 2 ) INFORMATION FOR SEQ ID NO:68:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( x i ) SEQUENCE DESCRIPTION: SEQ ID NO:68:

TGTAATTCAT TTTATTCCTA ATAGCTC 27

( 2 ) INFORMATION FOR SEQ ID NO:69:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( x i ) SEQUENCE DESCRIPTION: SEQ ID NO:69:

GGTAGCCATA GTATGATTAT TTCT                24

( 2 ) INFORMATION FOR SEQ ID NO:70:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:70:

CTACCTATTT TTATACCCAC AAAC                24

( 2 ) INFORMATION FOR SEQ ID NO:71:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:71:

AAGAAAGCCT ACACCATTTT TGC                 23

( 2 ) INFORMATION FOR SEQ ID NO:72:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:72:

GATCATTCTT AGAACCATCT TGC                 23

( 2 ) INFORMATION FOR SEQ ID NO:73:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:73:

ACCTATAGTC TAAATTATAC CATC                24

( 2 ) INFORMATION FOR SEQ ID NO:74:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:74:

GTCATGGCAT TAGTGACCAG          20

( 2 ) INFORMATION FOR SEQ ID NO:75:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:75:

AGTCGTAATT TTGTTTCTAA ACTC          24

( 2 ) INFORMATION FOR SEQ ID NO:76:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:76:

TGAAGGACTC GGATTTCACG C          21

( 2 ) INFORMATION FOR SEQ ID NO:77:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:77:

TCATTCACTC ACAGCCTGAT GAC          23

( 2 ) INFORMATION FOR SEQ ID NO:78:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:78:

GCTTTGAAAC ATGCACTACG AT 22

( 2 ) INFORMATION FOR SEQ ID NO:79:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:79:

AAACATCATT GCTCTTCAAA TAAC 24

( 2 ) INFORMATION FOR SEQ ID NO:80:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:80:

TACCATGATT TAAAAATCCA CCAG 24

( 2 ) INFORMATION FOR SEQ ID NO:81:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:81:

GATGATTGTC TTTTCCTCT TGC 23

( 2 ) INFORMATION FOR SEQ ID NO:82:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:82:

CTGAGCTATC TTAAGAAATA CATG 24

( 2 ) INFORMATION FOR SEQ ID NO:83:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:83:

TTTTAAATGA TCCTCTATTC TGTAT    25

( 2 ) INFORMATION FOR SEQ ID NO:84:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:84:

ACAGAGTCAG ACCCTGCCTC AAAG    24

( 2 ) INFORMATION FOR SEQ ID NO:85:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:85:

TTTCTATTCT TACTGCTAGC ATT    23

( 2 ) INFORMATION FOR SEQ ID NO:86:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:86:

ATACACAGGT AAGAAATTAG GA    22

( 2 ) INFORMATION FOR SEQ ID NO:87:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
                ( A ) ORGANISM: Homo sapiens ( x i ) SEQUENCE DESCRIPTION: SEQ ID NO:87:

TAGATGACCC ATATTCTGTT TC    22

( 2 ) INFORMATION FOR SEQ ID NO:88:

( i ) SEQUENCE CHARACTERISTICS:
                ( A ) LENGTH: 22 base pairs
                ( B ) TYPE: nucleic acid
                ( C ) STRANDEDNESS: single
                ( D ) TOPOLOGY: linear ( i i ) MOLECULE TYPE: cDNA ( v i ) ORIGINAL SOURCE:
                ( A ) ORGANISM: Homo sapiens ( x i ) SEQUENCE DESCRIPTION: SEQ ID NO:88:

CAATTAGGTC TTTTTGAGAG TA    22

( 2 ) INFORMATION FOR SEQ ID NO:89:

( i ) SEQUENCE CHARACTERISTICS:
                ( A ) LENGTH: 22 base pairs
                ( B ) TYPE: nucleic acid
                ( C ) STRANDEDNESS: single
                ( D ) TOPOLOGY: linear ( i i ) MOLECULE TYPE: cDNA ( v i ) ORIGINAL SOURCE:
                ( A ) ORGANISM: Homo sapiens ( x i ) SEQUENCE DESCRIPTION: SEQ ID NO:89:

GTTACTGCAT ACACATTGTG AC    22

( 2 ) INFORMATION FOR SEQ ID NO:90:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: cDNA ( v i ) ORIGINAL SOURCE:
                ( A ) ORGANISM: Homo sapiens ( x i ) SEQUENCE DESCRIPTION: SEQ ID NO:90:

GCTTTTTGTT TCCTAACATG AAG    23

( 2 ) INFORMATION FOR SEQ ID NO:91:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: cDNA ( v i ) ORIGINAL SOURCE:
                ( A ) ORGANISM: Homo sapiens ( x i ) SEQUENCE DESCRIPTION: SEQ ID NO:91:

TCTCCCACAG GTAATACTCC C    21

( 2 ) INFORMATION FOR SEQ ID NO:92:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:92:

GCTAGAACTG AATGGGGTAC G        21

( 2 ) INFORMATION FOR SEQ ID NO:93:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:93:

CAGGACAAAA TAATCCTGTC CC        22

( 2 ) INFORMATION FOR SEQ ID NO:94:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:94:

ATTTTCTTAG TTTCATTCTT CCTC        24

( 2 ) INFORMATION FOR SEQ ID NO: 95:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:95:

AGAAGGATCC CTTGTGCAGT GTGGA        25

( 2 ) INFORMATION FOR SEQ ID NO: 96:

( i ) SEQUENCE CHARACTERISTICS:
        ( A ) LENGTH: 24 base pairs
        ( B ) TYPE: nucleic acid
        ( C ) STRANDEDNESS: single ( D ) TOPOLOGY: linear ( i i ) MOLECULE TYPE: cDNA ( v i ) ORIGINAL SOURCE:
                    ( A ) ORGANISM: Homo sapiens ( x i ) SEQUENCE DESCRIPTION: SEQ ID NO:96:

GACAGGATCC TGAAGCTGAG TTTG                                                                              24

( 2 ) INFORMATION FOR SEQ ID NO: 97:

( i ) SEQUENCE CHARACTERISTICS:
                    ( A ) LENGTH: 18 base pairs
                    ( B ) TYPE: nucleic acid
                    ( C ) STRANDEDNESS: single
                    ( D ) TOPOLOGY: linear ( i i ) MOLECULE TYPE: cDNA ( v i ) ORIGINAL SOURCE:
                    ( A ) ORGANISM: Homo sapiens ( x i ) SEQUENCE DESCRIPTION: SEQ ID NO:97:

TCAGAAAGTG CTGAAGAG                                                                                     18

( 2 ) INFORMATION FOR SEQ ID NO: 98:

( i ) SEQUENCE CHARACTERISTICS:
                    ( A ) LENGTH: 19 base pairs
                    ( B ) TYPE: nucleic acid
                    ( C ) STRANDEDNESS: single
                    ( D ) TOPOLOGY: linear ( i i ) MOLECULE TYPE: cDNA ( v i ) ORIGINAL SOURCE:
                    ( A ) ORGANISM: Homo sapiens ( x i ) SEQUENCE DESCRIPTION: SEQ ID NO:98:

GGAATAATTA GGTCTCCAA                                                                                    19

( 2 ) INFORMATION FOR SEQ ID NO: 99:

( i ) SEQUENCE CHARACTERISTICS:
                    ( A ) LENGTH: 21 base pairs
                    ( B ) TYPE: nucleic acid
                    ( C ) STRANDEDNESS: single
                    ( D ) TOPOLOGY: linear ( i i ) MOLECULE TYPE: cDNA ( v i ) ORIGINAL SOURCE:
                    ( A ) ORGANISM: Homo sapiens ( x i ) SEQUENCE DESCRIPTION: SEQ ID NO:99:

GCAAATCCTA AGAGAGAACA A                                                                                 21

( 2 ) INFORMATION FOR SEQ ID NO: 100:

( i ) SEQUENCE CHARACTERISTICS:
                    ( A ) LENGTH: 19 base pairs
                    ( B ) TYPE: nucleic acid
                    ( C ) STRANDEDNESS: single
                    ( D ) TOPOLOGY: linear ( i i ) MOLECULE TYPE: cDNA ( v i ) ORIGINAL SOURCE:
                    ( A ) ORGANISM: Homo sapiens ( x i ) SEQUENCE DESCRIPTION: SEQ ID NO:100:

```
GATGGCAAGC TTGAGCCAG                                                                    19

( 2 ) INFORMATION FOR SEQ ID NO: 101:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: cDNA ( v i ) ORIGINAL SOURCE:
                ( A ) ORGANISM: Homo sapiens ( x i ) SEQUENCE DESCRIPTION: SEQ ID NO:101:

GTTCCAGCAG TGTCACAG                                                                     18

( 2 ) INFORMATION FOR SEQ ID NO: 102:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: cDNA ( v i ) ORIGINAL SOURCE:
                ( A ) ORGANISM: Homo sapiens ( x i ) SEQUENCE DESCRIPTION: SEQ ID NO:102:

GGGAGATTTC GCTCCTGA                                                                     18
```

APC ANTIBODIES

This application is a division, of application Ser. No. 08/289,548, filed Aug. 12, 1994, which is a division of application Ser. No. 07/741,940 filed Aug. 8, 1991 (issued as U.S. Pat. No. 5,352,775).

The U.S. Government has a paid-up license in this invention and the right in limited circumstances to require the patent owner to license others on reasonable terms as provided for by the terms of grants awarded by the National Institutes or Health.

TECHNICAL AREA OF THE INVENTION

The invention relates to the area of cancer diagnostics and therapeutics. More particularly, the invention relates to detection of the germline and somatic alterations of wild-type APC genes. In addition, it relates to therapeutic intervention to restore the function of APC gene product.

BACKGROUND OF THE INVENTION

According to the model of Knudson for tumorigenesis (Cancer Research, Vol. 45, p. 1482, 1985), there are tumor suppressor genes in all normal cells which, when they become non-functional due to mutation, cause neoplastic development. Evidence for this model has been found in the cases of retinoblastoma and colorectal tumors. The implicated suppressor genes in those tumors, RB, p53, DCC and MCC, were found to be deleted or altered in many cases of the tumors studied. (Hansen and Cavenee, Cancer Research, Vol. 47, pp: 5518–5527 (1987); Baker et al., Science, Vol. 244, p. 217 (1989); Fearon et al., Science, Vol. 247, p. 49 (1990); Kinzler et al. Science Vol. 251. p. 1366 (1991).)

In order to fully understand the pathogenesis of tumors, it will be necessary to identify the other suppressor genes that play a role in the tumorigenesis process. Prominent among these is the one(s) presumptively located at 5q21. Cytogenetic (Herrera et al., Am J. Med. Genet., Vol. 25, p. 473 (1986) and linkage (Leppert et al., Science, Vol. 238, p. 1411 (1987); Bodmer et al., Nature, Vol. 328, p. 614 (1987)) studies have shown that this chromosome region harbors the gene responsible for familial adenomatous polyposis (FAP) and Gardner's Syndrome (GS). FAP is an autosomal-dominant, inherited disease in which affected individuals develop hundreds to thousands of adenomatous polyps, some of which progress to malignancy. GS is a variant of FAP in which desmold tumors, osteomas and other soft tissue tumors occur together with multiple adenomas of the colon and rectum. A less severe form of polyposis has been identified in which only a few (2–40) polyps develop. This condition also is familial and is linked to the same chromosomal markers as FAP and GS (Leppert et al., New England Journal of Medicine, Vol. 322, pp. 904–908, 1990.) Additionally, this chromosomal region is often deleted from the adenomas (Vogelstein et al., N. Engl. J. Med., Vol. 319, p. 525 (1988)) and carcinomas (Vogelstein et al., N. Engl. J. Med., Vol. 319, p. 525 (1988); Solomon et al., Nature, Vol. 328, p. 616 (1987); Sasaki et al., Cancer Research, Vol. 49, p. 4402 (1989); Delattre et al., Lancet, Vol. 2, p. 353 (1989); and Ashton-Rickardt et al., Oncogene, Vol. 4, p. 1169 (1989)) of patients without FAP (sporadic tumors). Thus, a putative suppressor gene on chromosome 5q21 appears to play a role in the early stages of colorectal neoplasia in both sporadic and familial tumors.

Although the MCC gene has been identified on 5q21 as a candidate suppressor gene, it does not appear to be altered in FAP or GS patients. Thus there is a need in the art for investigations of this chromosomal region to identify genes and to determine if any of such genes are associated with FAP and/or GS and the process of tumorigenesis.

SUMMARY OF THE INVENTION

It is an object of the present invention to provide a method for diagnosing and prognosing a neoplastic tissue of a human.

It is another object of the invention to provide a method of detecting genetic predisposition to cancer.

It is another object of the invention to provide a method of supplying wild-type APC gene function to a cell which has lost said gene function.

It is yet another object of the invention to provide a kit for determination of the nucleotide sequence of APC alleles by the polymerase chain reaction.

It is still another object of the invention to provide nucleic acid probes for detection of mutations in the human APC gene.

It is still another object of the invention to provide a cDNA molecule encoding the APC gene product.

It is yet another object of the invention to provide a preparation of the human APC protein.

It is another object of the invention to provide a method of screening for genetic prodisposition to cancer.

It is an object of the invention to provide methods of testing therapeutic agents for the ability to suppress neoplasia.

It is still another object of the invention to provide animals carrying mutant APC alleles.

These and other objects of the invention are provided by one or more of the embodiments which are described below. In one embodiment of the present invention a method of diagnosing or prognosing a neoplastic tissue of a human is provided comprising: detecting somatic alteration of wild-type APC genes or their expression products in a sporadic colorectal cancer tissue, said alteration indicating neoplasia of the tissue.

In yet another embodiment a method is provided of detecting genetic predisposition to cancer in a human including familial adenomatous polyposis (FAP) and Gardner's Syndrome (GS), comprising: isolating a human sample selected from the group consisting of blood and fetal tissue; detecting alteration of wild-type APC gene coding sequences or their expression products from the sample, said alteration indicating genetic predisposition to cancer.

In another embodiment of the present invention a method is provided for supplying wild-type APC gene function to a cell which has lost said gene function by virtue of a mutation in the APC gene, comprising: introducing a wild-type APC gene into a cell which has lost said gene function such that said wild-type gene is expressed in the cell.

In another embodiment a method of supplying wild-type APC gene function to a cell is provided comprising: introducing a portion of a wild-type APC gene into a cell which has lost said gene function such that said portion is expressed in the cell, said portion encoding a part of the APC protein which is required for non-neoplastic growth of said cell. APC protein can also be applied to cells or administered to animals to remediate for mutant APC genes. Synthetic peptides or drugs can also be used to mimic APC function in cells which have altered APC expression.

In yet another embodiment a pair of single stranded primers is provided for determination of the nucleotide sequence of the APC gene by polymerase chain reaction. The sequence of said pair of single stranded DNA primers is derived from chromosome 5q band 21, said pair of primers allowing synthesis of APC gene coding sequences.

In still another embodiment of the invention a nucleic acid probe is provided which is complementary to human wild-type APC gene ceding sequences and which can form mismatches with mutant APC genes, thereby allowing their detection by enzymatic or chemical cleavage or by shifts in electrophoretic mobility.

In another embodiment of the invention a method is provided for detecting the presence of a neoplastic tissue in a human. The method comprises isolating a body sample from a human; detecting in said sample alteration of a wild-type APC gene sequence or wild-type APC expression product, said alteration indicating the presence of a neoplastic tissue in the human.

In still another embodiment a cDNA molecule is provided which comprises the coding sequence of the APC gene.

In even another embodiment a preparation of the human APC protein is provided which is substantially free of other human proteins. The amino acid sequence of the protein is shown in FIG. 3 (SEQ ID NOS: 7 and 2).

In yet another embodiment of the invention a method is provided for screening for genetic predisposition to cancer, including familial adenomatous polyposis (FAP) and Gardner's Syndrome (GS), in a human. The method comprises: detecting among kindred persons the presence of a DNA polymorphism which is linked to a mutant APC allele in an individual having a genetic predisposition to cancer, said kindred being genetically related to the individual, the presence of said polymorphism suggesting a predisposition to cancer.

In another embodiment of the invention a method of testing therapeutic agents for the ability to suppress a neoplastically transformed phenotype is provided. The method comprises: applying a test substance to a cultured epithelial cell which carries a mutation in an APC allele; and determining whether said test substance suppresses the neoplastically transformed phenotype of the cell.

In another embodiment of the invention a method of testing therapeutic agents for the ability to suppress a neoplastically transformed phenotype is provided. The method comprises: administering a test substance to an animal which carries a mutant APC allele; and determining whether said test substance prevents or suppresses the growth of tumors.

In still other embodiments of the invention transgenic animals are provided. The animals carry a mutant APC allele from a second animal species or have been genetically engineered to contain an insertion mutation which disrupts an APC allele.

The present invention provides the art with the information that the APC gene, a heretofore unknown gene is, in fact, a target of mutational alterations on chromosome 5q21 and that these alterations are associated with the process of tumorigenesis. This information allows highly specific assays to be performed to assess the neoplastic status of a particular tissue or the predisposition to cancer of an individual. This invention has applicability to Familial Adenomatous Polyposis, sporadic colorectal cancers, Gardner's Syndrome, as well as the less severe familial polyposis discusses above.

BRIEF DESCRIPTION OF THE DRAWINGS

FIG. 1A shows an overview of yeast artificial chromosome (YAC) contigs. Genetic distances between selected RFLP markers from within the contigs are shown in centi-Morgans.

FIGS. 2A and 2B show the sequence of TB1 (FIG. 2A) and TB2 (FIG. 2B) genes. The cDNA sequence of the TB1 gene was determined from the analysis of 11 cDNA clones derived from normal colon and liver, as described in the text. A total of 2314 bp were contained within the overlapping cDNA clones, defining an ORF of 424 amino acids beginning at nucleotide 1. Only the predicted amino acids from the ORF are shown. The carboxy-terminal end of the ORF has apparently been identified, but the 5' end of the TB1 transcript has not yet been precisely determined.

The cDNA sequence of the TB2 gene was determined from the YS-39 clone derived as described in the text. This clone consisted of 2300 bp and defined an ORF of 185 amino acids beginning at nucleotide 1. Only the predicted amino acids are shown. The carboxy terminal end of the ORF has apparently been identified, but the 5' end of the TB2 transcript has not been precisely determined.

FIGS. 3A–3F show the sequence of the APC gene product (SEQ ID NO:7). The cDNA sequence was determined through the analysis of 87 cDNA clones derived from normal colon, liver, and brain. A total of 8973 bp were contained within overlapping cDNA clones, defining an ORF of 2842 amino acids. In frame stop codons surrounded this ORF, as described in the text, suggesting that the entire APC gene product was represented in the ORF illustrated. Only the predicted amino acids are shown.

FIGS. 4A and 4B show the local similarity between human APC (SEQ ID NO:2) and ral2 (SEQ ID NO:8) of yeast. FIG. 4A shows amino acids 203 to 233 of APC, and FIG. 4B shows amino acids 453 to 481 of APC. Local similarity among the APC (SEQ ID NO:2) and MCC genes (SEQ ID NO:10) genes and the m3 muscarinic acetylcholine receptor (SEQ ID NO:9) is shown. The region of the mAChR shown corresponds to that responsible for coupling the receptor to G proteins. The connecting lines indicate identities; dots indicate related amino acids residues.

Figure 5:
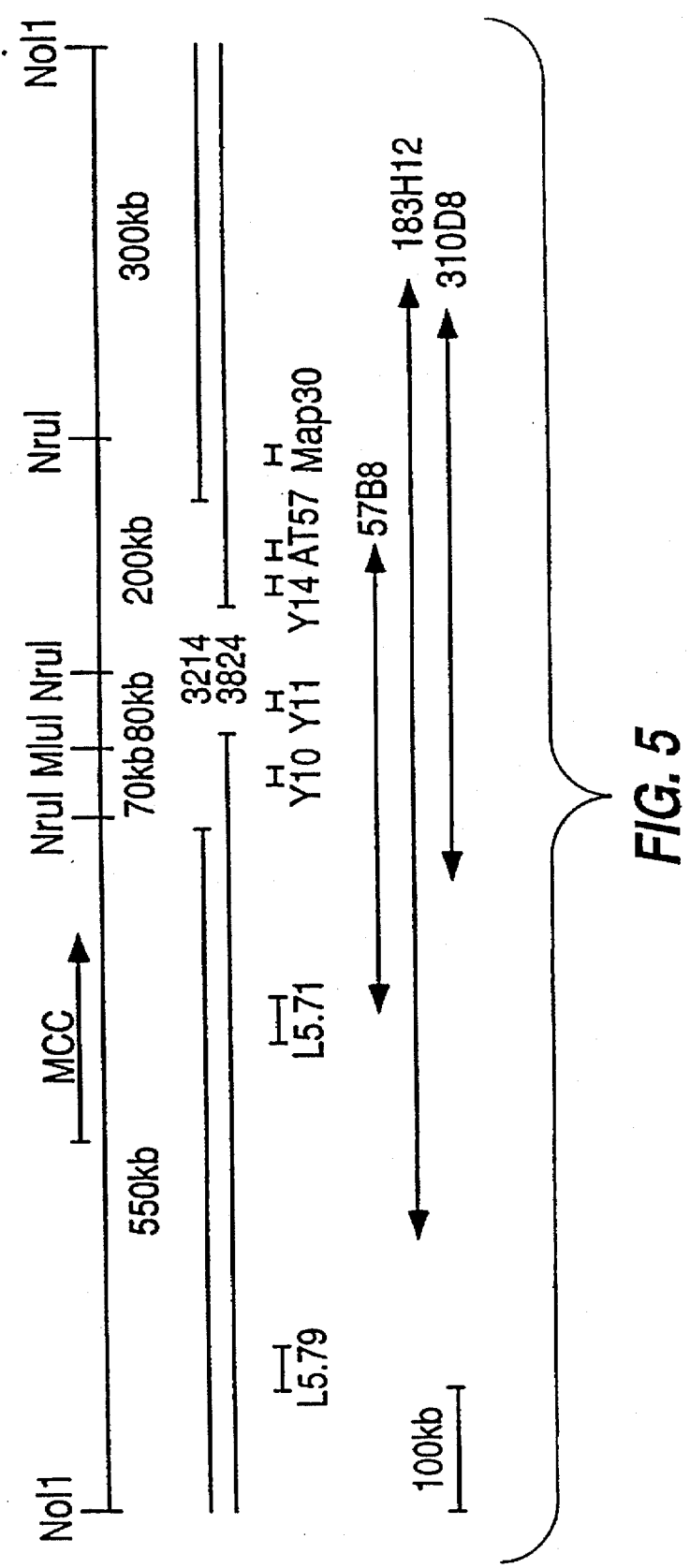
Figures 2, 7B:
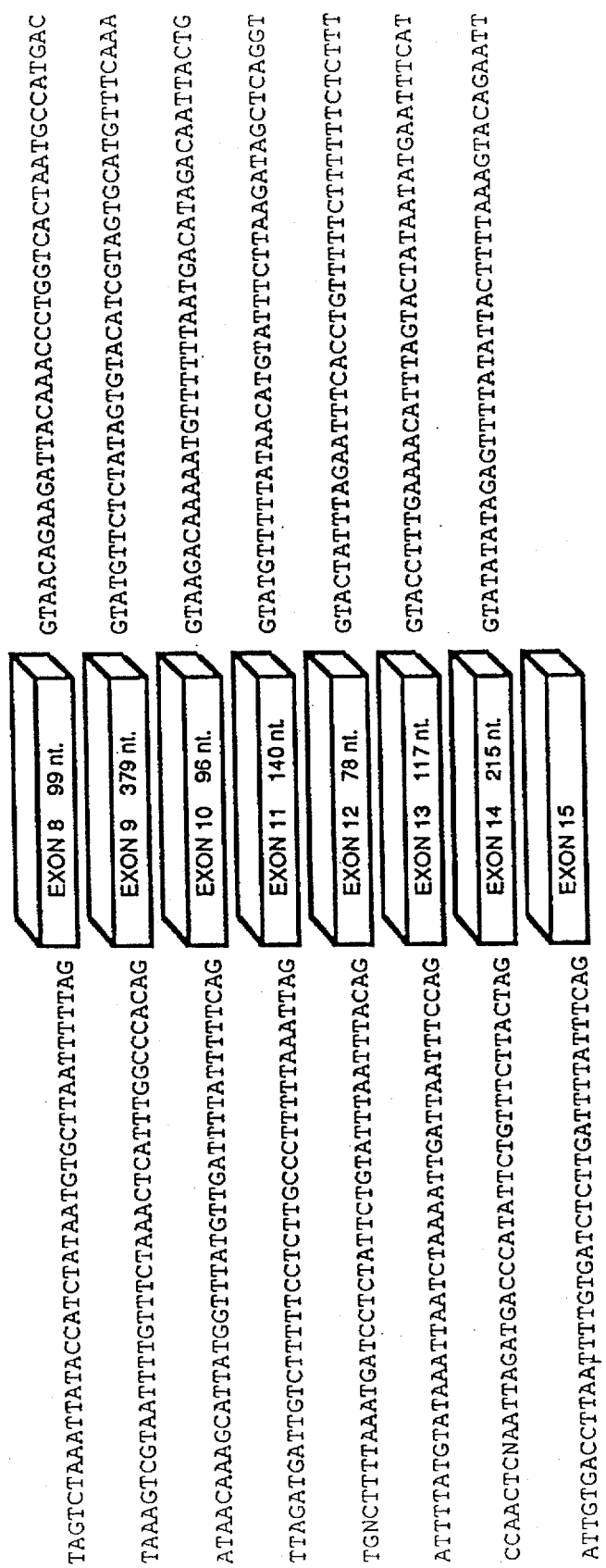

FIG. 5 shows the genomic map of the 1200 kb NotI fragment at the FAP locus. The NotI fragment is shown as a bold line. Relevant parts of the deletion chromosomes from patients 3214 and 3824 are shown as stippled lines. Probes used to characterize the NotI fragment and the deletions, and three YACs from which subclones were obtained, are shown below the restriction map. The chimeric end of YAC 183H12 is indicated by a dotted line. The orientation and approximate position of MCC are indicated above the map.

FIG. 6A–6D show the DNA sequence (SEQ ID NO:3) and predicted amino acid sequence of DP1 (TB2) (SEQ ID NO:4). The nucleotide numbering begins at the most 5' nucleotide isolated. A proposed initiation methionine (base 77) is indicated in bold type. The entire coding sequence is presented.

FIG. 7A, FIG. 7B-1, and FIG. 7B-2 show the arrangement of exons in DP2.5 (APC). (A) Exon 9 corresponds to nucleotides 933–1312; exon 9a corresponds to nucleotides 1236–1312. The stop codon in the cDNA is at nucleotide 8535. (B) Partial intronic sequence surrounding each exon is shown (SEQ ID NO: 11–38). 5' intron sequences of exons 2, 3, 4, 5, 6, 7, 8, 9, 10, 11, 12, 13, 14, and 15 are shown in SEQ ID NOS: 12, 14, 16, 18, 20, 22, 24, 26, 28, 30, 32, 34, 36, 38, respectively. 3' intron sequences of exons 1, 2, 3, 4, 5, 6, 7, 8, 9, 10, 11, 12, 13, and 14 are shown in SEQ ID NOS: 11, 13, 15, 17, 19, 21, 23, 25, 27, 29, 31, 33, 35, 37, respectively.

DETAILED DESCRIPTION

It is a discovery of the present invention that mutational events associated with tumorigenesis occur in a previously unknown gene on chromosome 5q named here the APC (Adenomatous Polyposis Coil) gene. Although it was previously known that deletion of alleles on chromosome 5q were common in certain types of cancers, it was not known that a target gene of these deletions was the APC gene. Further it was not known that other types of mutational events in the APC gene are also associated with cancers. The mutations of the APC gene can involve gross rearrangements, such as insertions and deletions. Point mutations have also been observed.

According to the diagnostic and prognostic method of the present invention, alteration of the wild-type APC gene is detected. "Alteration of a wild-type gene" according to the present invention encompasses all forms of mutations— including deletions. The alteration may be due to either rearrangements such as insertions, inversions, and deletions, or to point mutations. Deletions may be of the entire gene or only a portion of the gene. Somatic mutations are those which occur only in certain tissues, e.g., in the tumor tissue, and are not inherited in the germline. Germline mutations can be found in any of a body's tissues. If only a single allele is somatically mutated, an early neoplastic state is indicated. However, if both alleles are mutated then a late neoplastic state is indicated. The finding of APC mutations thus provides both diagnostic and prognostic information. An APC allele which is not deleted (e.g., that on the sister chromosome to a chromosome carrying an APC deletion) can be screened for other mutations, such as insertions, small deletions, and point mutations. It is believed that many mutations found in tumor tissues will be those leading to decreased expression of the APC gene product. However, mutations leading to non-functional gene products would also lead to a cancerous state. Point mutational events may occur in regulatory regions, such as in the promoter of the gene, leading to loss or diminution of expression of the mRNA. Point mutations may also abolish proper RNA processing, leading to loss of expression of the APC gene product.

In order to detect the alteration of the wild-type APC gene in a tissue, it is helpful to isolate the tissue free from surrounding normal tissues. Means for enriching a tissue preparation for tumor cells are known in the art. For example, the tissue may be isolated from paraffin or cryostat sections. Cancer cells may also be separated from normal cells by flow cytometry. These as well as other techniques for separating tumor from normal cells are well known in the art. If the tumor tissue is highly contaminated with normal cells, detection of mutations is more difficult.

Detection of point mutations may be accomplished by molecular cloning of the APC allele (or alleles) and sequencing that allele(s) using techniques well known in the art. Alternatively, the polymerase chain reaction (PCR) can be used to amplify gene sequences directly from a genomic DNA preparation from the tumor tissue. The DNA sequence of the amplified sequences can then be determined. The polymerase chain reaction itself is well known in the art. See, e.g., Saiki et al., Science, Vol. 239, p. 487, 1988; U.S. Pat. No. 4,683,203; and U.S. Pat. No. 4,683,195. Specific primers which can be used in order to amplify the gene will be discussed in more detail below. The ligase chain reaction, which is known in the art, can also be used to amplify APC sequences. See Wu et al., Genomics, Vol. 4, pp. 560–569 (1989). In addition, a technique known as allele specific PCR can be used. (See Ruano and Kidd, Nucleic Acids Research, Vol. 17, p. 8392, 1989.) According to this technique, primers are used which hybridize at their 3' ends to a particular APC mutation. If the particular APC mutation is not present, an amplification product is not observed. Amplification Refractory Mutation System (ARMS) can also be used as disclosed in European Patent Application Publication No. 0332435 and in Newton et al., Nucleic Acids Research, Vol. 17, p.7, 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening among kindred persons of an affected individual for the presence of the APC mutation found in that individual. Single stranded conformation polymorphism (SSCP) analysis can also be used to detect base change variants of an allele. (Orita et al., Proc. Natl. Acad. Sci. USA Vol. 86, pp. 2766–2770, 1989, and Genomics, Vol. 5, pp. 874–879, 1989.) Other techniques for detecting insertions and deletions as are known in the art can be used.

Figures 1, 1B, 2:
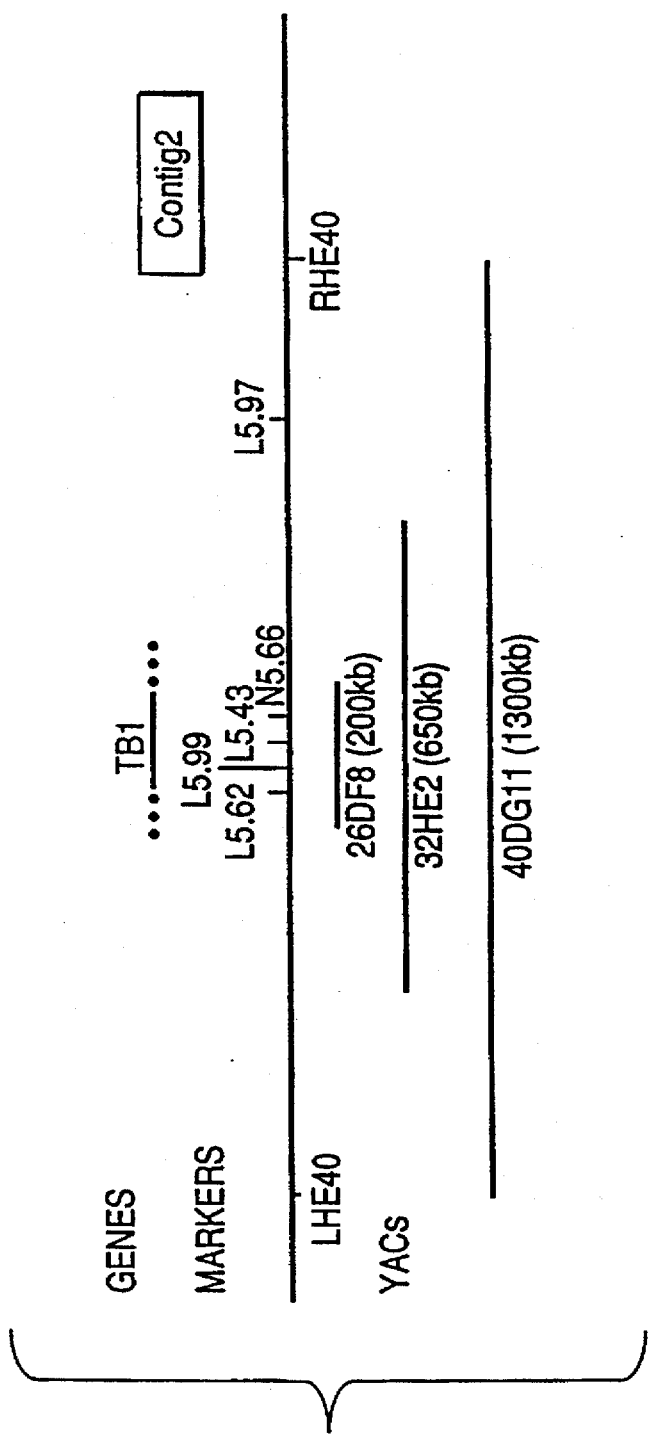
FIGS. 1B-1, 1B-2 and 1B-3 show a detailed map of the three central contigs. The position of the six identified genes from within the FAP region is shown; the 5' and 3' ends of the transcripts from these genes have in general not yet been isolated, as indicated by the string of dots surrounding the bars denoting the genes' positions. Selected restriction endonuclease recognition sites are indicated. B, BssH2; S, SstII; M, MluI; N, NruI.
Figures 1, 1B, 2, 3:
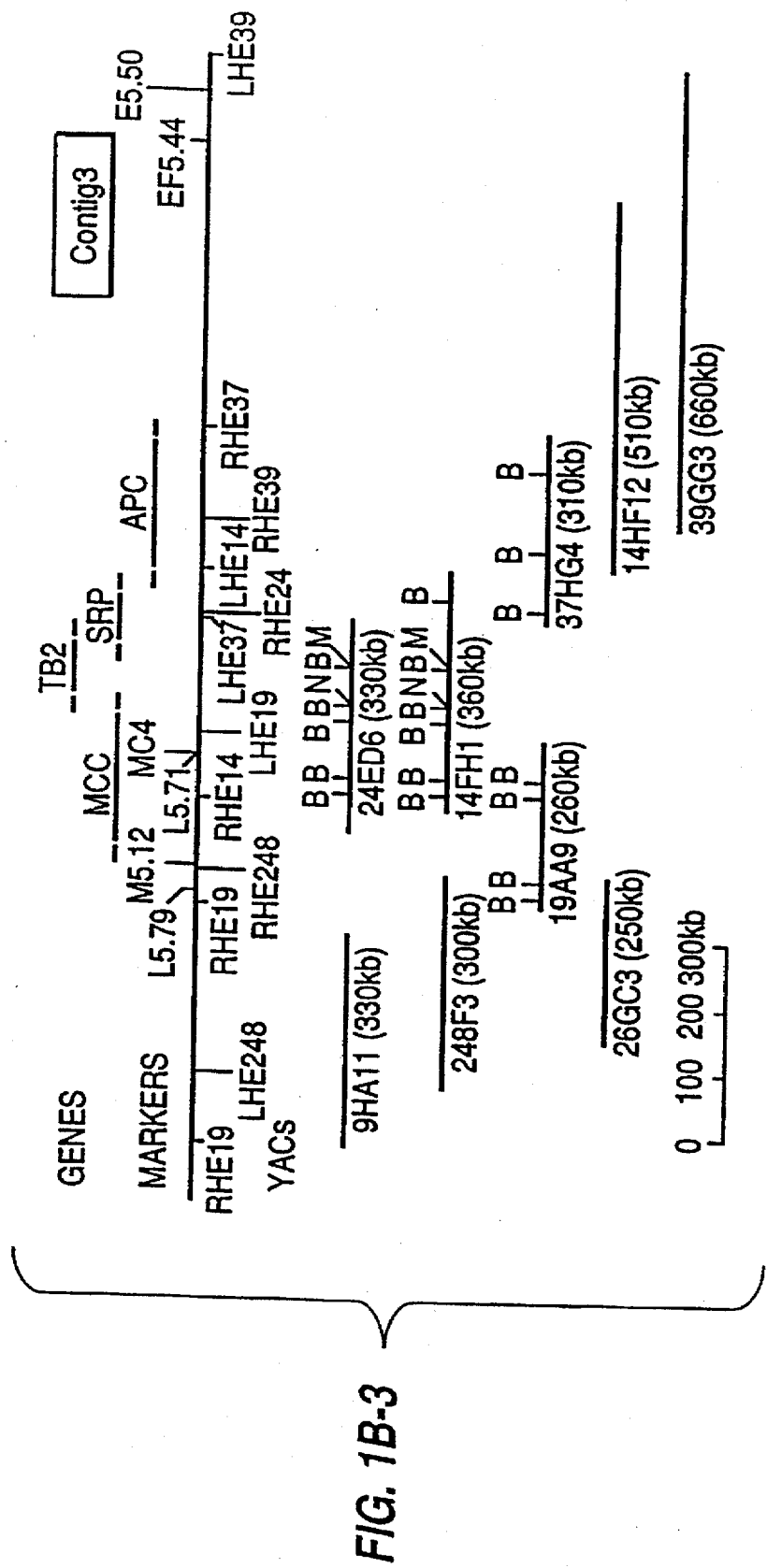

Alteration of wild-type genes can also be detected on the basis of the alteration of a wild-type expression product of the gene. Such expression products include both the APC mRNA as well as the APC protein product. The sequences of these products are shown in FIG. 3. Point mutations may be detected by amplifying and sequencing the mRNA or via molecular cloning of cDNA made from the mRNA. The sequence of the cloned cDNA can be determined using DNA sequencing techniques which are well known in the art. The cDNA can also be sequenced via the polymerase chain reaction (PCR) which will be discussed in more detail below.

Mismatches, according to the present invention are hybridized nucleic acid duplexes which are not 100% homologous. The lack of total homology may be due to deletions, insertions, inversions, substitutions or frameshift mutations. Mismatch detection can be used to detect point mutations in the gene or its mRNA product. While these techniques are less sensitive than sequencing, they are simpler to perform on a large number of tumor samples. An example of a mismatch cleavage technique is the RNase protection method, which is described in detail in Winter et al., Proc. Natl. Acad. Sci. USA, Vol. 82, p. 7575, 1985 and Meyers et al., Science, Vol. 230, p. 1242, 1985. In the practice of the present invention the method involves the use of a labeled riboprobe which is complementary to the human wild-type APC gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mRNA or DNA. The riboprobe need not be the full length of the APC mRNA or gene but can be a segment of either. If the riboprobe comprises only a segment of the APC mRNA or gene it will be desirable to use a number of these probes to screen the whole mRNA sequence for mismatches.

In similar fashion, DNA probes can be used to detect mismatches, through enzymatic or chemical cleavage. See, e.g., Cotton et al., Proc. Natl. Acad. Sci. USA, Vol. 85, 4397, 1988; and Shenk et al., Proc. Natl. Acad. Sci. USA, Vol. 72, p. 989, 1975. Alternatively, mismatches can be detected by shifts in the electrophoretic mobility of mismatched duplexes relative to matched duplexes. See, e.g., Cariello, Human Genetics, Vol. 42, p. 726, 1988. With either riboprobes or DNA probes, the cellular mRNA or DNA which might contain a mutation can be amplified using PCR (see below) before hybridization. Changes in DNA of the APC gene can also be detected using Southern hybridization, especially if the changes are gross rearrangements, such as deletions and insertions.

DNA sequences of the APC gene which have been amplified by use of polymerase chain reaction may also be screened using allele-specific probes. These probes are nucleic acid oligomers, each of which contains a region of the APC gene sequence harboring a known mutation. For example, one oligomer may be about 30 nucleotides in length, corresponding to a portion of the A PC gene sequence. By use of a battery of such allele-specific probes, PCR amplification products can be screened to identify the presence of a previously identified mutation in the APC gene. Hybridization of allele-specific probes with amplified APC sequences can be performed, for example, on a nylon filter. Hybridization to a particular probe under stringent hybridization conditions indicates the presence of the same mutation in the tumor tissue as in the allele-specific probe.

Alteration of APC mRNA expression can be detected by any technique known in the art. These include Northern blot analysis, PCR amplification and RNase protection. Diminished mRNA expression indicates an alteration of the wild-type APC gene. Alteration of wild-type APC genes can also be detected by screening for alteration of wild-type APC protein. For example, monoclonal antibodies immunoreactive with APC can be used to screen a tissue. Lack of cognate antigen would indicate an APC mutation. Antibodies specific for products of mutant alleles could also be used to detect mutant APC gene product. Such immunological assays can be done in any convenient format known in the art. These include Western blots, immunohistochemical assays and ELISA assays. Any means for detecting an altered APC protein can be used to detect alteration of wild-type APC genes. Functional assays can be used, such as protein binding determinations. For example, it is believed that APC protein oligomerizes to itself and/or MCC protein or binds to a G protein. Thus, an assay for the ability to bind to wild type APC or MCC protein or that G protein can be employed. In addition, assays can be used which detect APC biochemical function. It is believed that APC is involved in phospholipid metabolism. Thus, assaying the enzymatic products of the involved phospholipid metabolic pathway can be used to determine APC activity. Finding a mutant APC gene product indicates alteration of a wild-type APC gene.

Mutant APC genes or gene products can also be detected in other human body samples, such as, serum, stool, urine and sputum. The same techniques discussed above for detection of mutant APC genes or gene products in tissues can be applied to other body samples. Cancer cells are sloughed off from tumors and appear in such body samples. In addition, the APC gene product itself may be secreted into the extracellular space and found in these body samples even in the absence of cancer cells. By screening such body samples, a simple early diagnosis can be achieved for many types of cancers. In addition, the progress of chemotherapy or radiotherapy can be monitored more easily by testing such body samples for mutant APC genes or gene products.

The methods of diagnosis of the present invention are applicable to any tumor in which APC has a role in tumorigenesis. Deletions of chromosome arm 5q have been observed in tumors of lung, breast, colon, rectum, bladder, liver, sarcomas, stomach and prostate, as well as in leukemias and lymphomas. Thus these are likely to be tumors in which APC has a role. The diagnostic method of the present invention is useful for clinicians so that they can decide upon an appropriate course of treatment. For example, a tumor displaying alteration of both APC alleles might suggest a more aggressive therapeutic regimen than a tumor displaying alteration of only one APC allele.

The primer pairs of the present invention are useful for determination of the nucleotide sequence of a particular APC allele using the polymerase chain reaction. The pairs of single stranded DNA primers can be annealed to sequences within or surrounding the APC gene on chromosome 5q in order to prime amplifying DNA synthesis of the APC gene itself. A complete set of these primers allows synthesis of all of the nucleotides of the APC gene coding sequences, i.e., the exons. The set of primers preferably allows synthesis of both intron and exon sequences. Allele specific primers can also be used. Such primers anneal only to particular APC mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from APC sequences or sequences adjacent to APC except the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of the APC open reading frame shown in FIG. 3 (SEQ ID NO:1), design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the APC gene or mRNA using other techniques. Mismatches can be detected using either enzymes (e.g., S1 nuclease), chemicals (e.g., hydroxylamine or osmium tetroxide and piperidine), or changes in electrophoretic mobility of mismatched hybrids as compared to totally matched hybrids. These techniques are known in the art. See, Cotton, supra, Shenk, supra, Myers, supra, Winter, supra, and Novack et al., Proc. Natl. Acad. Sci. USA, Vol. 83, p. 586, 1986. Generally, the probes are complementary to APC gene coding sequences, although probes to certain introns are also contemplated. An entire battery of nucleic acid probes is used to compose a kit for detecting alteration of wild-type APC genes. The kit allows for hybridization to the entire APC gene. The probes may overlap with each other or be contiguous.

If a riboprobe is used to detect mismatches with mRNA, it is complementary to the mRNA of the human wild-type APC gene. The riboprobe thus is an anti-sense probe in that it does not code for the APC protein because it is of the opposite polarity to the sense strand. The riboprobe generally will be labeled with a radioactive, colorimetric, or fluorometric material, which can be accomplished by any means known in the art. If the riboprobe is used to detect mismatches with DNA it can be of either polarity, sense or anti-sense. Similarly, DNA probes also may be used to detect mismatches.

Nucleic acid probes may also be complementary to mutant alleles of the APC gene. These are useful to detect similar mutations in other patients on the basis of hybridization rather than mismatches. These are discussed above and referred to as allele-specific probes. As mentioned above, the A PC probes can also be used in Southern hybridizations to genomic DNA to detect gross chromosomal changes such as deletions and insertions. The probes can also be used to select cDNA clones of APC genes from tumor and normal tissues. In addition, the probes can be used to detect APC mRNA in tissues to determine if expression is diminished as a result of alteration of wild-type APC genes.

According to the present invention a method is also provided of supplying wild-type APC function to a cell which carries mutant APC alleles. Supplying such function should suppress neoplastic growth of the recipient cells. The wild-type APC gene or a part of the gene may be introduced into the cell in a vector such that the gene remains extrachromosomal. In such a situation the gene will be expressed by the cell from the extrachromosomal location. If a gene portion is introduced and expressed in a cell carrying a mutant APC allele, the gene portion should encode a part of the APC protein which is required for non-neoplastic growth of the cell. More preferred is the situation where the wild-type APC gene or a part of it is introduced into the mutant cell in such a way that it recombines with the endogenous mutant APC gene present in the cell. Such recombination requires a double recombination event which results in the correction of the APC gene mutation. Vectors for introduction of genes beth for recombination and for extrachromosomal maintenance are known in the art and any suitable vector may be used. Methods for introducing DNA into cells such as electroporation, calcium phosphate co-precipitation and viral transduction are known in the art and the choice of method is within the competence of the routineer. Cells transformed with the wild-type A PC gene can be used as model systems to study cancer remission and drug treatments which promote such remission.

Similarly, cells and animals which carry a mutant APC allele can be used as model systems to study and test for substances which have potential as therapeutic agents. The cells are typically cultured epithelial cells. These may be isolated from individuals with APC mutations, either somatic or germline. Alternatively, the cell line can be engineered to carry the mutation in the APC allele. After a test substance is applied to the cells, the neoplastically transformed pheno-type of the cell will be determined. Any trait of neoplastically transformed cells can be assessed, including anchorage-independent growth, tumorigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant A PC alleles, usually from a second animal species, as well as insertion of disrupted homologous genes. Alternatively, the endogenous APC gene(s) of the animals may be disrupted by insertion or deletion mutation. After test substances have been administered to the animals, the growth of tumors must be assessed. If the test substance prevents or suppresses the growth of tumors, then the test substance is a candidate therapeutic agent for the treatment of FAP and/or sporadic cancers.

Polypeptides which have APC activity can be supplied to cells which carry mutant or missing APC alleles. The sequence of the APC protein is disclosed in FIG. 3 (SEQ ID NO:7). These two sequences differ slightly and appear to be indicate the existence of two different forms of the APC protein. Protein can be produced by expression of the cDNA sequence in bacteria, for example, using known expression vectors. Alternatively, APC can be extracted from APC-producing mammalian cells such as brain cells. In addition, the techniques of synthetic chemistry can be employed to synthesize APC protein. Any of such techniques can provide the preparation of the present invention which comprises the APC protein. The preparation is substantially free of other human proteins. This is most readily accomplished by synthesis in a microorganism or in vitro.

Active APC molecules can be introduced into cells by microinjection or by use of liposomes, for example. Alternatively, some such active molecules may be taken up by cells, actively or by diffusion. Extracellular application of APC gene product may be sufficient to affect tumor growth. Supply of molecules with APC activity should lead to a partial reversal of the neoplastic state. Other molecules with APC activity may also be used to effect such a reversal, for example peptides, drugs, or organic compounds.

The present invention also provides a preparation of antibodies immunoreactive with a human APC protein. The antibodies may be polyclonal or monoclonal and may be raised against native APC protein, APC fusion proteins, or mutant APC proteins. The antibodies should be immunoreactive with APC epitopes, preferably epitopes not present on other human proteins. In a preferred embodiment of the invention the antibodies will immunoprecipitate APC proteins from solution as well as react with APC protein on Western or immunoblots of polyacrylamide gels. In another preferred embodiment, the antibodies will detect APC proteins in paraffin or frozen tissue sections, using immunocytochemical techniques. Techniques for raising and purifying antibodies are well known in the art and any such techniques may be chosen to achieve the preparation of the invention.

Predisposition to cancers as in FAP and GS can be ascertained by testing any tissue of a human for mutations of the APC gene. For example, a person who has inherited a germline APC mutation would be prone to develop cancers. This can be determined by testing DNA from any tissue of the person's body. Most simply, blood can be drawn and DNA extracted from the cells of the blood. In addition, prenatal diagnosis can be accomplished by testing fetal cells, placental cells, or amniotic fluid for mutations of the APC gene. Alteration of a wild-type APC allele, whether for example, by point mutation or by deletion, can be detected by any of the means discussed above.

Molecules of cDNA according to the present invention are intron-free, APC gene ceding molecules. They can be made by reverse transcriptase using the APC mRNA as a template. These molecules can be propagated in vectors and cell lines as is known in the art. Such molecules have the sequence shown in SEQ ID NO:3. The cDNA can also be made using the techniques of synthetic chemistry given the sequence disclosed herein.

A short region of homology has been identified between APC and the human m3 muscarinic acetylcholine receptor (mAChR). This homology was largely confined to 29 residues in which 6 out of 7 amino acids (EL(GorA)GLQA) were identical (See FIG. 4 (SEQ ID NO: 9)). Initially, it was not known whether this homology was significant, because many other proteins had higher levels of global homology (though few had six out of seven contiguous amino acids in common). However, a study on the sequence elements controlling G protein activation by mAChR subtypes (Lechleiter et al., EMBO J., p. 4381 (1990)) has shown that a 21 amino acid region from the m3 mAChR completely mediated G protein specificity when substituted for the 21 amino acids of m2 mA ChR at the analogous protein position. These 21 residues overlap the 19 amino acid homology between APC and m3 mA ChR.

This connection between APC and the G protein activating region of mAChR is intriguing in light of previous investigations relating G proteins to cancer. For example, the RAS oncogenes, which are often mutated in colorectal cancers (Vogelstein, et al., N. Engl. J. Med., Vol. 319, p. 525 (1988); Bos et al., Nature Vol. 327, p. 293 (1987)), are members of the (1 protein family (Bourne, et al, Nature, Vol. 348, p. 125 (1990)) as is an in vitro transformation suppressor (Noda et al., Proc. Natl. Acad. Sci. USA, Vol. 86, p. 162 (1989)) and genes mutated in hormone producing tumors (Candis et al., Nature, Vol. 340, p. 692 (1989); Lyons et al., Science, Vol. 249, p. 655 (1990)). Additionally, the gene responsible for neurofibromatosis (presumably a tumor suppressor gene) has been shown to activate the GTPase activity of RAS (Xu et al., Cell, Vol. 63, p. 835 (1990); Martin et al., Cell, Vol. 63, p. 843 (1990); Ballester et al., Cell, Vol. 63, p. 851 (1990)). Another interesting link between G proteins and colon cancer involves the drug sulindac. This agent has been shown to inhibit the growth of benign colon tumors in patients with FAP, presumably by virtue of its activity as a cyclooxygenase inhibitor (Waddell et al., J. Surg. Oncology 24(1), 83 (1983); Wadell, et al., Am. J. Surg., 157(1), 175 (1989); Charneau et al., Gastroenterologie Clinique at Biologique 14(2), 153 (1990)). Cyclooxygenase is required to convert arachidonic acid to prostaglandins and other biologically active molecules. G proteins are known to regulate phospholipase A2 activity, which generates arachidonic acid from phospholipids (Role et al., Proc. Natl. Acad. Sci. USA, Vol. 84, p. 3623 (1987); Kurachi et al., Nature, Vol. 337, 12 555 (1989)). Therefore we propose that wild-type APC protein functions by interacting with a G protein and is involved in phospholipid metabolism.

The following are provided for exemplification purposes only and are not intended to limit the scope of the invention which has been described in broad terms above.

EXAMPLE 1

This example demonstrates the isolation of a 5.5 Mb region of human DNA linked to the FAP locus. Six genes are identified in this region, all of which are expressed in normal colon cells and in colorectal, lung, ad bladder tumors.

The cosmid markers YN5.64 and YN5.48 have previously been shown to delimit an 8 cM region containing the locus for FAP (Nakamura et al., Am. J. Hum. Genet. Vol. 43, p. 638 (1988)). Further linkage and pulse-field gel electrophoresis (PFGE) analysis with additional markers has shown that the FAP locus is contained within a 4 cM region bordered by cosmids EF5.44 and L5.99. In order to isolate clones representing a significant portion of this locus, a yeast artificial chromosome (YAC) library was screened with various 5q21 markers. Twenty-one YAC clones, distributed within six contigs and including 5.5 Mb from the region between YN5.64 and YN5.48, were obtained (FIG. 1A).

Three contigs encompassing approximately 4 Mb were contained within the central portion of this region. The YAC's constituting these contigs, together with the markers used for their isolation and orientations, are shown in FIG. 1. These YAC contigs were obtained in the following way. To initiate each contig, the sequence of a genomic marker cloned from chromosome 5q21 was determined and used to design primers for PCR. PCR was then carried out on pools of YAC clones distributed in microtiter trays as previously described (Anand et al., Nucleic Acids Research, Vol. 18, p. 1951 (1980)). Individual YAC clones from the positive pools were identified by further PCR or hybridization based assays, and the YAC sizes were determined by PFGE.

To extend the areas covered by the original YAC clones, "chromosomal walking" was performed. For this purpose, YAC termini were isolated by a PCR based method and sequenced (Riley et al., Nucleic Acids Research, Vol. 18, p. 2887 (1990)). PCR primers based on these sequences were then used to rescreen the YAC library. For example, the sequence from an intron of the FER gene (Hao et al., Mol. Cell. Biol., Vol. 9, p. 1587 (1989)) was used to design PCR primers for isolation of the 28EC1 and 5EH8 YACs. The termini of the 28EC1 YAC were sequenced to derive markers RHE28 and LHE28, respectively. The sequences of these two markers were then used to isolate YAC clones 15CH12 (from RHE28) and 40CF1 and 29EF1 (from LHE28). These five YAC's formed a contig encompassing 1200 kb (contig 1, FIG. 1B).

Similarly, contig 2 was initiated using cosmid N5.66 sequences, and contig 3 was initiated using sequences both from the MCC gene and from cosmid EF5.44. A walk in the telomeric direction from YAC 14FH1 and a walk in the opposite direction from YAC 39GG3 allowed connection of the initial contig 3 clones through YAC 37HG4 (FIG. 1B). YAC37HG4 was deposited at the National Collection of Industrial and Marine Bacteria (NCIMB), P.O. Box 31, 23 St. Machar Drive, Aberdeen AB2 1RY, Scotland, under Accession No. 40353 on Dec. 17, 1990.

Multipoint linkage analysis with the various markers used to define the contigs, combined with PFGE analysis, showed that contigs 1 and 2 were centromeric to contig 3. These contigs were used as tools to orient and/or identify genes which might be responsible for FAP. Six genes were found to lie within this cluster of YAC's, as follows:

Contig #1: FER—The FER gene was discovered through its homology to the viral oncogene ABL (Hao et al., supra). It has an intrinsic tyrosine kinase activity, and in situ hybridization with an FER probe showed that the gene was located at 5q11-23 (Morris et al., Cytogenet. Cell. Genet., Vol. 53, p. 4, (1990)). Because of the potential role of this oncogene-related gene in neoplasia, we decided to evaluate it further with regards to the FAP locus. A human genomic clone from FER was isolated (MF 2.3) and used to define a restriction fragment length polymorphism (RFLP), and the RFLP in turn used to map FER by linkage analysis using a panel of three generation families. This showed that FER was very tightly linked to previously defined polymorphic markers for the FAP locus. The genetic mapping of FER was complemented by physical mapping using the YAC clones derived from FER sequences (FIG. 1B). Analysis of YAC contig 1 showed that FER was within 600 kb of cosmid marker M5.28, which maps to within 1.5 Mb of cosmid L5.99 by PFGE of human genomic DNA. Thus, the YAC mapping results were consistent with the FER linkage data and PFGE analyses.

Contig 2: TB1—TB1 was identified through a cross-hybridization approach. Exons of genes are often evolutionarily conserved while introns and intergenic regions are much less conserved. Thus, it a human probe cross-hybridizes strongly to the DNA from non-primate species, there is a reasonable chance that it contains exon sequences. Subclones of the cosmids shown in FIG. 1 were used to screen Southern blots containing rodent DNA samples. A subclone of cosmid N5.66 (p 5.66–4) was shown to strongly hybridize to rodent DNA, and this clone was used to screen cDNA libraries derived from normal adult colon and fetal liver. The ends of the initial cDNA clones obtained in this screen were then used to extend the cDNA sequence. Eventually, 11 cDNA clones were isolated, covering 2314 bp. The gene detected by these clones was named TB1. Sequence analysis of the overlapping clones revealed an open reading frame (ORF) that extended for 1302 bp starting from the most 5' sequence data obtained (FIG. 2A). If this entire open reading frame were translated, it would encode 434 amino acids (SEQ ID NO:5). The product of this gene was not globally homologous to any other sequence in the current database but showed two significant local similarities to a family of ADP, ATP carrier/translocator proteins and mitochondrial brown fat uncoupling proteins which are widely distributed from yeast to mammals. These conserved regions of TB1 (underlined in FIG. 2A) may define a predictive motif for this sequence family. In addition, TB1 appeared to contain a signal peptide (or mitochondrial targeting sequence) as well as at least 7 transmembrane domains.

Contig 3: MCC, TB2, SRP and APC—The MCC gene was also discovered through a cross-hybridization approach, as described previously (Kinzler et al., Science Vol. 251, p. 1366 (1991)). The MCC gene was considered a candidate for causing FAP by virtue of its tight genetic linkage to FAP susceptibility and its somatic mutation in sporadic colorectal carcinomas. However, mapping experiments suggested that the ceding region of MCC was approximately 50 kb proximal to the centromeric end of a 200 kb deletion found in an FAP patient. MCC cDNA probes detected a 10 kb mRNA transcript on Northern blot analysis of which 4151 bp, including the entire open reading frame, have been cloned. Although the 3' non-translated portion or an alternatively spliced form of MCC might have extended into this deletion, it was possible that the deletion did not affect the MCC gene product. We therefore used MCC sequences to initiate a YAC contig, and subsequently used the YAC clones to identify genes 50 to 250 kb distal to MCC that might be contained within the deletion.

In a first approach, the insert from YAC24ED6 (FIG. 1B) was radiolabelled and hybridized to a cDNA library from normal colon. One of the cDNA clones (YS39) identified in this manner detected a 3.1 kb mRNA transcript when used as a probe for Northern blot hybridization. Sequence analysis of the YS39 clone revealed that it encompassed 2283 nucleotides and contained an ORF that extended for 555 bp from the most 5' sequence data obtained. If all of this ORF were translated, it would encode 185 amino acids (SEQ ID NO:6) (FIG. 2B). The gene detected by YS39 was named TB2. Searches of nucleotide and protein databases revealed that the TB2 gene was not identical to any previously reported sequences nor were there any striking similarities.

Another clone (YS11) identified through the YAC 24ED6 screen appeared to contain portions of two distinct genes. Sequences from one end of YS11 were identical to at least 180 bp of the signal recognition particle protein SRP19 (Lingelbach et al. Nucleic Acids Research, Vol. 16, p. 9431 (1988). A second ORF, from the opposite end of clone YS11, proved to be identical to 78 bp of a novel gene which was independently identified through a second YAC-based approach. For the latter, DNA from yeast cells containing YAC 14FH1 (FIG. 1B) was digested with EcoRI and subcloned into a plasmid vector. Plasmids that contained human DNA fragments were selected by colony hybridization using total human DNA as a probe. These clones were then used to search for cross-hybridizing sequences as described above for TB1, and the cross-hybridizing clones were subsequently used to screen cDNA libraries. One of the cDNA clones discovered in this way (FH38) contained a long ORF (2496 bp), 78 bp of which were identical to the above-noted sequences in YS11. The ends of the FH38 cDNA clone were then used to initiate cDNA walking to extend the sequence. Eventually, 85 cDNA clones were isolated from normal colon, brain and liver cDNA libraries and found to encompass 8973 nucleotides of contiguous transcript. The gene corresponding to this transcript was named APC. When used as probes for Northern blot analysis, APC cDNA clones hybridized to a single transcript of approximately 9.5 kb, suggesting that the great majority of the gene product was represented in the cDNA clones obtained. Sequences from the 5' end of the APC gene were found in YAC 37HG4 but not in YAC 14FH1. However, the 3' end of the APC gene was found in 14FH1 as well as 37HG4. Analogously, the 5' end of the MCC ceding region was found in YAC clones 19AA9 and 266C3 but not 24ED6 or 14FH1, while the 3' end displayed the opposite pattern. Thus, MCC and APC transcription units pointed in opposite directions, with the direction of transcription going from centromeric to telomeric in the case of MCC, and telomeric to centromeric in the case of APC. PFGE analysis of YAC DNA digested with various restriction endonucleases showed that TB2 and SRP were between MCC and APC, and that the 3' ends of the ceding regions of MCC and APC were separated by approximately 150 kb (FIG. 1B).

Sequence analysis of the APC cDNA clones revealed an open reading frame of 8,535 nucleotides. The 5' end of the ORF contained a methionine codon (codon 1) that was preceded by an in-frame stop codon 9 bp upstream, and the 3' end was followed by several in-frame stop codons. The protein produced by initiation at codon 1 would contain 2,842 amino acids (SEQ ID NO:7) (FIG. 3). The results of database searching with the APC gene product were quite complex due to the presence of large segments with locally biased amino acid compositions. In spite of this, APC could be roughly divided into two domains. The N-terminal 25% of the protein had a high content of leucine residues (12%) and showed local sequence similarities to myosins, various intermediate filament proteins (e.g., desmin, vimentin, neurofilaments) and Drosophila armadillo/human plakoglobin. The latter protein is a component of adhesive junctions (desmosomes) joining epithelial cells (Franke et al., Proc. Natl. Acad. Sci. U.S.A., Vol. 86, p. 4027 (1989); Perfer et al., Cell, Vol. 63, p. 1167 (1990)) The C-terminal 75% of APC (residues 731–2832) is 17% serine by composition with serine residues more or less uniformly distributed. This large domain also contains local concentrations of charged (mostly acidic) and proline residues. There was no indication of potential signal peptides, transmembrane regions, or nuclear targeting signals in APC, suggesting a cytoplasmic localization.

To detect short similarities to APC, a database search was performed using the PAM-40 matrix (Altschul. J. Mol. Bio., Vol. 219, p. 555 (1991)). Potentially interesting matches to several proteins were found. The most suggestive of these involved the ral2 gene product of yeast, which is implicated in the regulation of ras activity (Fukui et al., Mol. Cell. Biol., Vol. 9, p. 5617 (1989)). Little is known about how ral2 might interact with ras but it is interesting to note the positively-charged character of this region in the context of the negatively-charged GAP interaction region of ras. A specific electrostatic interaction between ras and GAP-related proteins has been proposed.

Because of the proximity of the MCC and APC genes, and the fact that both am implicated in colorectal tumorigenesis, we searched for similarities between the two predicted proteins. Bourne has previously noted that MCC has the potential to form alpha helical coiled coils (Nature, Vol. 351, p. 188 (1991). Lupas and colleagues have recently developed a program for predicting coiled coil potential from primary sequence data (Science, Vol. 252, p. 1162 (1991) and we have used their program to analyze both MCC and APC. Analysis of MCC indicated a discontinuous pattern of coiled-coil domains separated by putative "hinge" or "sparer" regions similar to those seen in laminin and other intermediate filament proteins. Analysis of the APC sequence revealed two regions in the N-terminal domain which had strong coiled coil-forming potential, and these regions corresponded to those that showed local similarities with myosin and IF proteins on database searching. In addition, one other putative coiled coil region was identified in the central region of APC. The potential for both APC and MCC to form coiled coils is interesting in that such structures often mediate homo- and hetero-oligomerization.

Finally, it had previously been noted that MCC shared a short similarity with the region of the m3 muscarinic acetylcholine receptor (mAChR) known to regulate specificity of G-protein coupling. The APC gene also contained a local similarity to the region of the m3 mAChR (SEQ ID NO:9) that overlapped with the MCC similarity (SEQ ID NO:10) (FIG. 4B). Although the similarities to ral2 (SEQ ID NO:8) (FIG. 4A) and m3 mAChR (SEQ ID NO:9) (FIG. 4B) were not statistically significant, they were intriguing in light of previous observations relating G-proteins to neoplasia.

Each of the six genes described above was expressed in normal colon mucosa, as indicated by their representation in colon cDNA libraries. To study expression of the genes in neoplastic colorectal epithelium, we employed reverse transcription-polymerase chain reaction (PCR) assays. Primers based on the sequences of FER, TB1, TB2, MCC, and APC were each used to design primers for PCR performed with cDNA templates. Each of these genes was found to be expressed in normal colon, in each of ten cell lines derived from colorectal cancers, and in tumor cell lines derived from lung and bladder tumors. The ten colorectal cancer cell lines included eight from patients with sporadic CRC and two from patients with FAP.

EXAMPLE 2

This example demonstrates a genetic analysis of the role of the FER gene in FAP and sporadic colorectal cancers.

We considered FER as a candidate because of its proximity to the FAP locus as judged by physical and genetic criteria (see Example 1), and its homology to known tyrosine kinases with oncogenic potential. Primers were designed to PCR-amplify the complete coding sequence of FER from the RNA of two colorectal cancer cell lines derived from FAP patients. cDNA was generated from RNA and used as a template for PCR. The primers used were 5'-AGAAGGATCCCTTGTGCAGTGTGGA-3' (SEQ ID NO:95) and 5'-GACAGGATCCTGAAGCTGAGTTTG-3' (SEQ ID NO:96). The underlined nucleotides were altered from the true FER sequence to create BamHI sites. The cell lines used were JW and Difi, both derived from colorectal cancers of FAP patients. (C. Paraskeva, B. G. Buckle, D. Sheer, C. B. Wigley, Int. J. Cancer 34, 49 (1984); M. E. Gross et al., Cancer Res. 51, 1452 (1991). The resultant 2554 basepair fragments were cloned and sequenced in their entirety. The PCR products were cloned in the BamHI site of Bluescript SK (Stratagene) and pools of at least 50 clones were sequenced en masse using T7 polymerase, as described in Nigro et al., Nature 342, 705 (1989).

Only a single conservative amino acid change (GTG→CTG, creating a val to leu substitution at codon 439) was observed. The region surrounding this codon was then amplified from the DNA of individuals without FAP and this substitution was found to be a common polymorphism, not specifically associated with FAP. Based on these results, we considered it unlikely (though still possible) the FER gene was responsible for FAP. To amplify the regions surrounding codon 439, the following primers were used: 5'-TCAGAAAGTGCTGAAGAG-3' (SEQ ID NO:97) and 5'-GGAATAATTAGGTCTCCAA-3' (SEQ ID NO:98). PCR products were digested with PstI, which yields a 50 bp fragment if codon 439 is leucine, but 26 and 24 bp fragments if it is valine. The primers used for sequencing were chosen from the FER cDNA sequence in Hao et al., supra.

EXAMPLE 3

This example demonstrates the genetic analysis of MCC, TB2, SRP and APC in FAP and sporadic colorectal tumors. Each of these genes is linked and encompassed by contig 3 (see FIG. 1).

Several lines of evidence suggested that this contig was of particular interest. First, at least three of the four genes in this contig were within the deleted region identified in two FAP patients. (See Example 5 infra.) Second, allelic deletions of chromosome 5q21 in sporadic cancers appeared to be centered in this region. (Ashton-Rickardt et al., Oncogene, in press; and Miki et al., Japn. J. Cancer Res., in press.) Some tumors exhibited loss of proximal RFLP markers (up to and potentially including the 5' end of MCC), but no loss of markers distal to MCC. Other tumors exhibited loss of markers distal to and perhaps including the 3' end of MCC, but no loss of sequences proximal to MCC. This suggested either that different ends of MCC were affected by loss in all such cases, or alternatively, that two genes (one proximal to and perhaps including MCC, the other distal to MCC) were separate targets of deletion. Third, clones from each of the six FAP region genes were used as probes on Southern blots containing tumor DNA from patients with Sporadic CRC. Only two examples of somatic changes were observed in over 200 tumors studied: a rearrangement/deletion whose centromeric end was located within the MCC gene (Kinzler et al., supra) and an 800 bp insertion within the APC gene between nucleotides 4424 and 5584. Fourth, point mutations of MCC were observed in two tumors (Kinzler et al.) supra strongly suggesting that MCC was a target of mutation in at least some sporadic colorectal cancers.

Based on these results, we attempted to search for subtle alterations of contig 3 genes in patients with FAP. We chose to examine MCC and APC, rather than TB2 or SRP, because of the somatic mutations in MCC and APC noted above. To facilitate the identification of subtle alterations, the genomic sequences of MCC and APC exons were determined (see Table I, SEQ ID NO:24–38).

TABLE I

APC EXONS

| EXON NUCLEOTIDES[1] | EXON BOUNDARY SEQUENCE[2] |
|---|---|
| 822 to 930 | catgatgttatctgtatttacctatagtctaaattataccatctataatgtgcttaatttttag/GGTTCA . . . (SEQ ID NO: 24) |
| | . . . ACCAAG/gtaacagaagattacaaaccctggtcactaatgccatgactactttgctaag (SEQ ID NO: 25) |
| 931 to 1309 | ggatattaaagtcgtaattttgtttctaaactcatttggcccacag/GTGGAA . . . (SEQ ID NO: 26) |
| | . . . ATCCAA/gtatgttctctatagtgtacatcgtagtgcatg (SEQ ID NO: 27) |
| 1310 to 1405 | catcattgctcttcaaataacaaagcattatggtttatgttgattttattttcag/TGCCAG . . . (SEQ ID NO: 28) |
| | . . . AACTAG/gtaagacaaaaatgttttttaatgacatagacaattactggtg (SEQ ID NO: 29) |
| 1406 to 1545 | tagatgattgtcttttcctcttgcccttttaaattag/GGGGAC . . . (SEQ ID NO: 30) |
| | . . . AACAAG/gtatgtttttataacatgtatttcttaaggatagctcaggtatga (SEQ ID NO: 31) |
| 1546 to 1623 | gcttggcttcaagttgtcttttaatgatcctctattctgtatttaatttacag/GCTACG . . . (SEQ ID NO: 32) |
| | . . . CAGCAG/gtactatttagaatttcacctgtttttctttttctctttttctttgaggcagggtctcactctg (SEQ ID NO: 33) |
| 1624 to 1740 | gcaactagtatgatttatgtataaattaatctaaaattgattaatttgacag/GTTATT . . . (SEQ ID NO: 34) |
| | . . . AAAAAG/gtacctttgaaaacatttagtactataatatgaatttcatgt (SEQ ID NO: 35) |
| 1741 to 1955 | caactctaattagatgacccatattcagaaaacttactag/GAATCA . . . (SEQ ID NO: 36) |
| | . . . CCACAG/gtatatatagagtttatattacttttaaagtacagaattcatactctcaaaaa (SEQ ID NO: 37) |
| 1956 to 8973 | tcttgattttatttcag/GCAAAT . . . (SEQ ID NO: 38) |
| | . . . GGTATTTATGCAAAAAAAAATGTTTTTGT (SEQ ID NO: 1) |

[1]Relative to predicted translation initiation site
[2]Small case letters represent introns, large case letters represent exons
The entire 3' end of the cloned APC cDNA (nt 1956–8973) appeared to be encoded in this exon, as indicated by restriction endonuclease mapping and sequencing of the cloned genomic DNA. The ORF ended at nt 8535. The extreme 3' end of the APC transcript has not yet been identified.

These sequences were used to design primers for PCR analysis of constitutional DNA from FAP patients.

We first amplified eight exons and surrounding introns of the MCC gene in affected individuals from 90 different FAP kindreds. The PCR products were analyzed by a ribonuclease (RNase) protein assay. In brief, the PCR products were hybridized to in vitro transcribed RNA probes representing the normal genomic sequences. The hybrids were digested with RNase A, which can cleave at single base pair mismatches within DNA-RNA hybrids, and the cleavage products were visualized following denaturing gel electrophoresis. Two separate RNase protection analyses were performed for each exon, one with the sense and one with the antisense strand. Under these conditions, approximately 40% of all mismatches are detectable. Although some amino acid variants of MCC were observed in FAP patients, all such variants were found in a small percentage of normal individuals. These variants were thus unlikely to be responsible for the inheritance of FAP.

We next examined three exons of the APC gene. The three exons examined included those containing nt 822–930, 931–1309, and the first 300 nt of the most distal exon (nt 1956–2256). PCR and RNase protection analysis were performed as described in Kinzler et al. supra, using the primers underlined in Table I (SEQ ID NO:24–38). The primers for nt 1956–2256 were 5'-GCAAATCCTAAGAGAGAACAA-3' (SEQ ID NO:99) and 5'-GATGGCAAGCTTGAGCCAG-3' (SEQ ID NO:100).

In 90 kindreds, the RNase protection method was used to screen for mutations and in an additional 13 kindreds, the PCR products were cloned and sequenced to search for mutations not detectable by RNase protection. PCR products were cloned into a Bluescript vector modified as described in T. A. Holton and M. W. Graham, Nucleic Acids Res. 19, 1156 (1991). A minimum of 100 clones were pooled and sequenced. Five variants were detected among the 103 kindreds analyzed. Cloning and subsequent DNA sequencing of the PCR product of patient P21 indicated a C to T transition in codon 413 that resulted in a change from arginine to cysteine. This amino acid variant was not observed in any of 200 DNA samples from individuals without FAP. Cloning and sequencing of the PCR product from patients P24 and P34, who demonstrated the same abnormal RNase protection pattern indicated that both had a C to T transition at codon 801 that resulted in a change from arginine (CGA) to a stop codon (TGA). This change was not present in 200 individuals without FAP. As this point mutation resulted in the predicted loss of the recognition site for the enzyme Taq I, appropriate PCR products could be digested with Taq I to detect the mutation. This allowed us to determine that the stop codon co-segragated with disease phenotype in members of the family of P24. The inheritance of this change in affected members of the pedigree provides additional evidence for the importance of the mutation.

Cloning and sequencing of the PCR product from FAP patient P93 indicated a C to G transversion at codon 279, also resulting in a stop codon (change from TCA to TGA). This mutation was not present in 200 individuals without FAP. Finally, one additional mutation resulting in a serine (TCA) to stop codon (TGA) at codon 712 was detected in a single patient with FAP (patient P60).

The five germline mutations identified are summarized in Table IIA, as well as four others discussed in Example 9.

TABLE IIA

Germline mutations of the APC gene in FAP and GS Patients

| EXTRA-COLONIC PATIENT DISEASE | CODON | NUCLEOTIDE CHANGE | AMINO ACID CHANGE | AGE | |
|---|---|---|---|---|---|
| 93 | 279 | TCA->TGA | Ser->Stop | 39 | Mandibular |
| Osteoma | | | | | |
| 24 | 301 | CGA->TGA | Arg->Stop | 46 | None |
| 34 | 301 | CGA->TGA | Arg->Stop | 27 | Desmoid |
| Tumor | | | | | |
| 21 | 413 | CGC->TGC | Arg->Cys | 24 | Mandibular |

TABLE IIA-continued

Germline mutations of the APC gene in FAP and GS Patients

| EXTRA-COLO-NIC PATIENT DISEASE | CODON | NUCLEO-TIDE CHANGE | AMINO ACID CHANGE | AGE | |
|---|---|---|---|---|---|
| Osteoma | | | | | |
| 60 | 712 | TCA->T<u>G</u>A | Ser->Stop | 37 | Mandibular |
| Osteoma | | | | | |
| 3746 | 243 | CAGAG->CAG | splice-junction | | |
| 3460 | 301 | CGA->T<u>G</u>A | Arg->Stop | | |
| 3827 | 456 | CTTTCA->CTTCA | frameshift | | |
| 3712 | 500 | T-><u>G</u> | Tyr->Stop | | |

*The mutated nucleotides are underlined.

In addition to these germline mutations, we identified several somatic mutations of MCC and APC in sporadic CRC's. Seventeen MCC exons were examined in 90 sporadic colorectal cancers by RNase protection analysis. In each case where an abnormal RNase protection pattern was observed, the corresponding PCR products were cloned and sequenced. This led to the identification of six point mutations (two described previously) (Kinzler et al., supra), each of which was not found in the germline of these patients (Table IIB).

TABLE IIB

Somatic Mutations in Sporadic CRC Patients

| PATIENT | CODON[1] | NUCLEOTIDE CHANGE | AMINO ACID CHANGE |
|---|---|---|---|
| T35 | MCC 12 | GAG/gtaaga-> GAG/gtaaaa | (Splice Donor) |
| T16 | MCC 145 | ctcag/GGA-> atcag/GGA | (Splice Acceptor) |
| T47 | MCC 267 | CGG->C<u>T</u>G | Arg->Leu |
| T81 | MCC 490 | TCG->T<u>T</u>G | Ser->Leu |
| T35 | MCC 506 | CGG->C<u>A</u>G | Arg->Gln |
| T91 | MCC 698 | GCT->G<u>T</u>T | Ala->Val |
| T34 | APC 288 | CCAGT->CCC<u>AGCC</u>AGT | (Insertion) |
| T27 | APC 331 | CGA->T<u>G</u>A | Arg->Stop |
| T135 | APC 437 | CAA/gtaa->CAA/g<u>c</u>aa | (Splice Donor) |
| T201 | APC 1338 | CAG->T<u>A</u>G | Gln->Stop |

For splice site mutations, the codon nearest to the mutation is listed
The underlined nucleotides were mutant; small case letters represent introns, large case letters represent exons Four of the mutations resulted in amino acid substitutions and two resulted in the alteration of splice site consensus elements. Mutations at analogous splice site positions in other genes have been shown to alter RNA processing in vivo and in vitro.

Three exons of APC were also evaluated in sporadic tumors. Sixty tumors were screened by RNase protection, and an additional 98 tumors were evaluated by sequencing. The exons examined included nt 822–930, 931–1309, and 1406–1545 (Table I). A total of three mutations were identified, each of which proved to be somatic. Tumor T27 contained a somatic mutation of CGA (arginine) to TGA (stop codon) at codon 33. Tumor T135 contained a GT to GC change at a splice donor site. Tumor T34 contained a 5 bp insertion (CAGCC between codons 288 and 289) resulting in a stop at codon 291 due to a frameshift.

We serendipitously discovered one additional somatic mutation in a colorectal cancer. During our attempt to define the sequences and splice patterns of the MCC and APC gene products in colorectal epithelial cells, we cloned cDNA from the colorectal cancer cell line SW480. The amino acid sequence of the MCC gene from SW480 was identical to that previously found in clones from human brain. The sequence of APC in SW480 cells, however, differed significantly, in that a transition at codon 1338 resulted in a change from glutamine (CAG) to a stop codon (TAG). To determine if this mutation was somatic, we recovered DNA from archival paraffin blocks of the original surgical specimen (T201) from which the tumor cell line was derived 28 years ago.

DNA was purified from paraffin sections as described in S. E. Goelz, S. R. Hamilton, and B. Vogelstein. Biochem. Biophys. Res. Comm. 130, 118 (1985). PCR was performed as described in reference 24, using the primers 5'-GTTCCAGCAGTGTCACAG-3' (SEQ ID NO:101) and 5'-GGGAGATTTCGCTCCTGA-3' (SEQ ID NO:102). A PCR product containing codon 1338 was amplified from the archival DNA and used to show that the stop codon represented a somatic mutation present in the original primary tumor and in cell lines derived from the primary and metastatic tumor sites, but not from normal tissue of the patient.

The ten point mutations in the MCC and APC genes so far discovered in sporadic CRCs are summarized in Table IIB. Analysis of the number of mutant and wild-type PCR clones obtained from each of these tumors showed that in eight of the ten cases, the wild-type sequence was present in approximately equal proportions to the mutant. This was confirmed by RFLP analysis using flanking markers from chromosome 5q which demonstrated that only two of the ten tumors (T135 and T201) exhibited an allelic deletion on chromosome 5q. These results are consistent with previous observations showing that 20–40% of sporadic colorectal tumors had allelic deletions of chromosome 5q. Moreover, these data suggest that mutations of 5q21 genes are not limited to those colorectal tumors which contain allelic deletions of this chromosome.

EXAMPLE 4

This example characterizes small, nested deletions in DNA from two unrelated FAP patients.

DNA from 40 FAP patients was screened with cosmids that has been mapped into a region near the APC locus to identify small deletions or rearrangements. Two of these cosmids, L5.71 =nd L5.79, hybridized with a 1200 kb NotI fragment in DNAs from most of the FAP patients screened.

The DNA of one FAP patient, 3214, showed only a 940 kb NotI fragment instead of the expected 1200 kb fragment. DNA was analyzed from four other members of the patient's immediate family; the 940 kb fragment was present in her affected mother (4711), but not in the other, unaffected family members. The mother also carried a normal 1200 kb NotI fragment that was transmitted to her two unaffected offspring. These observations indicated that the mutant polyposis allele is on the same chromosome as the 940 kb NotI fragment. A simple interpretation is that APC patients 3214 and 4711 each carry a 260 kb deletion within the APC locus.

If a deletion were present, then other enzymes might also be expected to produce fragments with altered mobilities. Hybridization of L5.79 to NruI-digested DNAs from both affected members of the family revealed a novel NruI fragment of 1300 kb, in addition to the normal 1200 kb NruI fragment. Furthermore, MluI fragments in patients 3214 and 4711 also showed an increase in size consistent with the deletion of an MluI site. The two chromosome 5 homologs of patient 3214 were segregated in somatic cell hybrid lines; HHW1155 (deletion hybrid) carried the abnormal homolog and HHW1159 (normal hybrid) carried the normal homolog.

Because patient 8214 showed bray a 940 kb NotI fragment, she had not inherited the 1200 kb fragment present in the unaffected father's DNA. This observation suggests that he must be heterozygous for, and have transmitted, either a deletion of the L5.79 probe region or a variant NotI fragment too large to resolve on the gel system. As expected, the hybrid cell line HHW1159, which carries the paternal homolog, revealed no resolved Not fragment when probed with L5.79. However, probing of HHW1159 DNA with L5.79 following digestion with other enzymes did reveal restriction fragments, demonstrating the presence of DNA homologous to the probe. The father is, therefore, interpreted as heterozygous for a polymorphism at the NotI site, with one chromosome 5 having a 1200 kb NotI fragment and the other having a fragment too large to resolve consistently on the gel. The latter was transmitted to patient 3214.

When double digests were used to order restriction sites within the 1200 kb NotI fragment, L5.71 and L5.79 were both found to lie on a 550 kb NotI-NruI fragment and, therefore, on the same side of an NruI site in the 1200 kb NotI fragment. To obtain genomic representation of sequences present over the entire 1200 kb NotI fragment, we constructed a library of small-fragment inserts enriched for sequences from this fragment. DNA from the somatic cell hybrid HHW141, which contains about 40% of chromosome 5, was digested with NotI and electrophoresed under pulsed-field gel (PFG) conditions; EcoRI fragments from the 1200 kb region of this gel were cloned into a phage vector. Probe Map30 was isolated from this library. In normal individuals probe Map30 hybridizes to the 1200 kb NotI fragment and to a 200 kb NruI fragment. This latter hybridization places Map30 distal, with respect to the locations of L5.71 and L5.79, to the NruI site of the 550 kb NotI-NruI fragment.

Because Map30 hybridized to the abnormal, 1300 kb NruI fragment of patient 3214, the locus defined by Map30 lies outside the hypothesized deletion. Furthermore, in normal chromosomes Map30 identified a 200 kb NruI fragment and L5.79 identified a 1200 kb NruI fragment; the hypothesized deletion must, therefore, be removing an NruI site, or sites, lying between Map30 and L5.79, and these two probes must flank the hypothesized deletion. A restriction map of the genomic region, showing placement of these probes, is shown in FIG. 5.

A NotI digest of DNA from another FAP patient, 3824, was probed with L5.79. In addition to the 1200 kb normal NotI fragment, a fragment of approximately 1100 kb was observed, consistent with the presence of a 100 kb deletion in one chromosome 5. In this case, however, digestion with NruI and MluI did not reveal abnormal bands, indicating that if a deletion were present, its boundaries must lie distal to the NruI and MluI sites of the fragments identified by L5.79. Consistent with this expectation, hybridization of Map30 to DNA from patient 3824 identified a 760 kb MluI fragment in addition to the expected 860 kb fragment, supporting the interpretation of a 100 kb deletion in this patient. The two chromosome 5 homologs of patient 3824 were segregated in somatic cell hybrid lines; HHW1291 was found to carry only the abnormal homolog and HHW1290 only the normal homolog.

That the 860 kb MluI fragment identified by Map30 is distinct from the 830 kb MluI fragment identified previously by L5.79 was demonstrated by hybridization of Map30 and L5.79 to a NotI-MluI double digest of DNA from the hybrid cell (HHW1159) containing the nondeleted chromosome 5 homolog of patient 3214. As previously indicated, this hybrid is interpreted as missing one of the NotI sites that define the 1200 kb fragment. A 620 kb NotI-MluI fragment was seen with probe L5.79, and an 860 kb fragment was seen with Map30. Therefore, the 830 kb MluI fragment recognized by probe L5.79 must contain a NotI site in HHW1159 DNA; because the 860 kb MluI fragment remains intact, it does not carry this NotI site and must be distinct from the 830 kb MluI fragment.

EXAMPLE 5

This example demonstrates the isolation of human sequences which span the region deleted in the two unrelated FAP patients characterized in Example 4.

A strong prediction of the hypothesis that patients 8214 and 3824 carry deletions is that some sequences present on normal chromosome 5 homologs would be missing from the hypothesized deletion homologs. Therefore, to develop genomic probes that might confirm the deletions, as well as to identify genes from the region, YAC clones from a contig seeded by cosmid L5.79 were localized from a library containing seven haploid human genome equivalents (Albertsen et al., Proc. Natl. Acad. Sci. U.S.A., Vol. 87, pp. 4256–4260 (1990)) with respect to the hypothesized deletions. Three clones, YACs 57B8, 310D8, and 183H12, were found to overlap the deleted region.

Importantly, one end of YAC 57B8 (clone AT57) was found to lie within the patient 3214 deletion. Inverse polymerase chain reaction (PCR) defined the end sequences of the insert of YAC 57B8. PCR primers based on one of these end sequences repeatedly failed to amplify DNA from the somatic cell hybrid (HHW1155) carrying the deleted homolog of patient 3214, but did amplify a product of the expected size from the somatic cell hybrid (HHW1159) carrying the normal chromosome 5 homolog. This result supported the interpretation that the abnormal restriction fragments found in the DNA of patient 3214 result from a deletion.

Additional support for the hypothesis of deletion in DNA from patient 3214 came from subcloned fragments of YAC 183H12, which spans the region in question. Y11, an EcoRI fragment cloned from YAC 183H12, hybridized to the normal, 1200 kb NotI fragment of patient 4711, but failed to hybridize to the abnormal, 940 kb NotI fragment of 4711 or to DNA from deletion cell line HHW1155. This result confirmed the deletion in patient 3214.

Two additional EcoRI fragments from YAC 183H12, Y10 and Y14, were localized within the patient 3214 deletion by their failure to hybridize to DNA from HHW1155. Probe Y10 hybridizes to a 150 kb NruI fragment in normal chromosome 5 homologs. Because the 3214 deletion creates the 1300 kb NruI fragment seen with the probes L5.79 and Map30 that flank the deletion, these NruI sites and the 150 kb NruI fragment lying between must be deleted in patient 3214. Furthermore, probe Y10 hybridizes to the same 620 kb NotI-MluI fragment seen with probe L5.79 in normal DNA, indicating its location as L5.79-proximal to the deleted MluI site and placing it between the MluI site and the L5.79-proximal NruI site. The MluI site must, therefore, lie between the NruI sites that define the 150 kb NruI fragment (see FIG. 5).

Probe Y11 also hybridized to the 150 kb NruI fragment in the normal chromosome 5 homolog, but failed to hybridize to the 620 kb NotI-MluI fragment, placing it L5.79-distal to the MluI site, but proximal to the second NruI site. Hybridization to the same (860 kb) MluI fragment as Map30 confirmed the localization of probe Y11 L5.79-distal to the MluI site.

Probe Y14 was shown to be L5.79-distal to both deleted NruI sites by virtue of its hybridization to the same 200 kb NruI fragment of the normal chromosome 5 seen with Map30. Therefore, the order of these EcoRI fragments derived from YAC 183H12 and deleted in patient 3214, with respect to L5.79 and Map30, is L5.79-Y10-Y11-Y14-Map30.

The 100 kb deletion of patient 3824 was confirmed by the failure of aberrant restriction fragments in this DNA to hybridize with probe Y11, combined with positive hybridizations to probes Y10 and/or Y14. Y10 and Y14 each hybridized to the 1100 kb NotI fragment of patient 3824 as well as to the normal 1200 kb NotI fragment, but Y11 hybridized to the 1200 kb fragment only. In the MluI digest, probe Y14 hybridized to the 860 kb and 760 kb fragments of patient 3824 DNA, but probe Y11 hybridized only to the 860 k13 fragment. We conclude that the basis for the alteration in fragment size in DNA from patient 3824 is, indeed, a deletion. Furthermore, because probes Y10 and Y14 are missing from the deleted 3214 chromosome, but present on the deleted 3824 chromosome, and they have been shown to flank probe Y11, the deletion in patient 3824 must be nested within the patient 3214 deletion.

Probes Y10, Y11, Y14 and Map30 each hybridized to YAC 310D8, indicating that this YAC spanned the patient 3824 deletion and at a minimum, most of the 3214 deletion. The YAC characterizations, therefore, confirmed the presence of deletions in the patients and provided physical representation of the deleted region.

EXAMPLE 6

This example demonstrates that the MCC coding sequence maps outside of the region deleted in the two FAP patients characterized in Example 4.

An intriguing FAP candidate gene, MCC, recently was ascertained with cosmid L5.71 and was shown to have undergone mutation in colon carcinomas (Kinzler et al., supra). It was therefore of interest to map this gene with respect to the deletions in APC patients. Hybridization of MCC probes with an overlapping series of YAC clones extending in either direction from L5.71 showed that the 3' end of MCC must be oriented toward the region of the two APC deletions.

Therefore, two 3' cDNA clones from MCC were mapped with respect to the deletions: clone 1CI (bp 2378–4181) and clone 7 (bp 2890–3560). Clone 1CI contains sequences from the C-terminal end of the open reading frame, which stops at nucleotide 2708, as well as 3' untranslated sequence. Clone 7 contains sequence that is entirely 3' to the open reading frame. Importantly, the entire 3' untranslated sequence contained in the cDNA clones consists of a single 2.5 kb exon. These two clones were hybridized to DNAs from the YACs spanning the FAP region. Clone 7 fails to hybridize to YAC 310D8, although it does hybridize to YACs 183H12 and 57B8; the same result was obtained with the cDNA 1CI. Furthermore, these probes did show hybridization to DNAs from both hybrid cell lines (HWW1159 and HWW1155) and the lymphoblastoid cell line from patient 3214, confirming their locations outside the deleted region. Additional mapping experiments suggested that the 3' end of the MCC cDNA clone contig is likely to be located more than 45 kb from the deletion of patient 3214 and, therefore, more than 100 kb from the deletion of patient 3824.

EXAMPLE 7

This example identifies three genes within the deleted region of chromosome 5 in the two unrelated FAP patients characterized in Example 4.

Genomic clones were used to screen cDNA libraries in three separate experiments. One screening was done with a phage clone derived from YAC 310D8 known to span the 260 kb deletion of patient 3214. A large-insert phage library was constructed from this YAC; screening with Y11 identified λ205, which mapped within both deletions. When clone λ205 was used to probe a random-, plus oligo(dT)-, primed fetal brain cDNA library (approximately 300,000 phage), six cDNA clones were isolated and each of them mapped entirely within both deletions. Sequence analysis of these six clones formed a single cDNA contig, but did not reveal an extended open reading frame. One of the six cDNAs was used to isolate more cDNA clones, some of which crossed the L5.71-proximal breakpoint of the 3824 deletion, as indicated by hybridization to both chromosome of this patient. These clones also contained an open reading frame, indicating a transcriptional orientation proximal to distal with respect to L5.71. This gene was named DP1 (deleted in polyposis 1). This gene is identical to TB2 described above.

cDNA walks yielded a cDNA contig of 3.0–3.5 kb, and included two clones containing terminal poly(A) sequences. This size corresponds to the 3.5 kb band seen by Northern analysis. Sequencing of the first 3163 bp of the cDNA contig revealed an open reading frame extending from the first base to nucleotide 631, followed by a 2.5 kb 3' untranslated region. The sequence surrounding the methionine codon at base 77 conforms to the Kozak consensus of an initiation methionine (Kozak, 1984). Failed attempts to walk farther, coupled with the similarity of the lengths of isolated cDNA and mRNA, suggested that the $NH_2$-terminus of the DP1 protein had been reached. Hybridization to a combination of genomic and YAC DNAs cut with various enzymes indicated the genomic coverage of DP1 to be approximately 30 kb.

Two additional probes for the locus, YS-11 and YS-39, which had been ascertained by screening of a cDNA library with an independent YAC probe identified with MCC sequences adjacent to L5.71, were mapped into the deletion region. YS-39 was shown to be a cDNA identical in sequence to DP1. Partial characterization of YS-11 had shown that 200 bp of DNA sequence at one end was identical to sequence coding for the 19 kd protein of the ribosomal signal recognition particle, SRP19 (Lingelbach et al., supra). Hybridization experiments mapped YS-11 within beth deletions. The sequence of this clone, however, was found to be complex. Although 454 bp of the 1032 bp sequence of YS-11 were identical to the GenBank entry for the SRP19 gene, another 578 bp appended 5' to the SRP19 sequence was found to consist of previously unreported sequence containing no extended open reading frames. This suggested that YS-11 was either a chimeric clone containing two independent inserts or a clone of an incompletely processed or aberrant message. If YS-11 were a conventional chimeric clone, the independent segments would not be expected to map to the same physical region. The segments resulting from anomalous processing of a continuous transcript, however, would map to a single chromosomal region.

Inverse PCR with primers specific to the two ends of YS-11, the SRP19 ,end and the unidentified region, verified that both sequences map within the YAC 310D8; therefore, YS-11 is most likely a clone of an immature or anomalous mRNA species. Subsequently, both ends were shown to lie with the deleted region of patient 3824, and YS-11 was used to screen for additional cDNA clones.

Of the 14 cDNA clones selected from the fetal brain library, one clone, V5, was of particular interest in that it contained an open reading frame throughout, although it included only a short identity to the first 78 5' bases of the YS-11 sequence. Following the 78 bp of identical sequence, the two cDNA sequences diverged at an AG. Furthermore, divergence from genomic sequence was also seen after these 78 bp, suggesting the presence of a splice junction, and supporting the view that YS-11 represents an irregular message.

Starting with V5, successive 5' and 3' walks were performed; the resulting cDNA contig consisted of more than 100 clones, which defined a new transcript, DP2. Clones walking in the 5' direction crossed the 3824 deletion breakpoint farthest from L5.71; since its 3' end is closer to this cosmid than its 5' end, the transcriptional orientation of DP2 is opposite to that of MCC and DP1.

The third screening approach relied on hybridization with a 120 kb MluI fragment from YAC 57B8. This fragment hybridizes with probe Y11 and completely spans the 100 kb deletion in patient 3824. the fragment was purified on two preparative PFGs, labeled, and used to screen a fetal brain cDNA library. A number of cDNA clones previously identified in the development of the DP1 and DP2 contigs were reascertained. However, 19 new cDNA clones mapped into the patient 3824 deletion. Analysis indicated that these 19 formed a new contig, DP3, containing a large open reading frame.

A clone from the 5' end of this new cDNA contig hybridized to the same EcoRI fragment as the 3' end of DP2. Subsequently, the DP2 and DP3 contigs were connected by a single 5' walking step from DP3, to form the single contig DP2.5. The complete nucleotide sequence of DP2.5 is shown in FIG. 9.

The consensus cDNA sequence of DP2.5 suggests that the entire coding sequence of DP2.5 has been obtained and is 8532 bp long. The most 5' ATG codon occurs two codons from an in-frame stop and conforms to the Kozak initiation consensus (Kozak, Nucl. Acids. Res., Vol. 12, p. 857–872 1984). The 3' open reading frame breaks down over the final 1.8 kb, giving multiple stops in all frames. A poly(A) sequence was found in one clone approximately 1 kb into the 3' untranslated region, associated with a polyadenylation signal 33 bp upstream (position 9530). The open reading frame is almost identical to that identified as APC above.

An alternatively spliced exon at nucleotide 934 of the DP2.5 transcript is of potential interest. it was first discovered by noting that two classes of cDNA had been isolated. The more abundant cDNA class contains a 303 bp exon not included in the other. The presence in vivo of the two transcripts was verified by an exon connection experiment. Primers flanking the alternatively spliced exon were used to amplify, by PCR, cDNA prepared from various adult tissues. Two PCR products that differed in size by approximately 300 bases were amplified from all the tissues tested; the larger product was always more abundant than the smaller.

EXAMPLE 8

This example demonstrates the primers used to identify subtle mutations in DP1, SRP19, and DP25.

To obtain DNA sequence adjacent to the exons of the genes DP1, DP2.5, and SRP19, sequencing substrate was obtained by inverse PCR amplification of DNAs from two YACs, 310D8 and 183H12, that span the deletions. Ligation at low concentration cyclized the restriction enzyme-digested YAC DNAs. Oligonucleotides with sequencing tails, designed in inverse orientation at intervals along the cDNAs, primed PCR amplification from the cyclized templates. Comparison of these DNA sequences with the cDNA sequences placed exon boundaries at the divergence points. SRP19 and DP1 were each shown to have five exons. DP2.5 consisted of 15 exons. The sequences of the oligonucleotides synthesized to provide PCR amplification primers for the exons of each of these genes are listed in Table III SEQ ID NO:39–94.

TABLE III

Sequences of Primers Used for SSCP Analyses

| Exon | Primer 1 | Primer 2 |
|---|---|---|
| | DP1 | |
| | UP-TCCCCGCCTGCCGCTCTC | RP-GCAGCGGCGGCTCCCGTG |
| | UP-GTGAACGGCTCTCATGCTGC | RP-ACGTGCGGGGAGGAATGGA |
| | UP-ATGATATCTTACCAAATGATATAC | RP-TTATTCCTACTTCTTCTATACAG |
| | UP-TACCCATGCTGGCTCTTTTTC | RP-TGGGGCCATCTTGTTCCTGA |
| | UP-ACATTAGGCACAAAGCTTGCAA | RP-ATCAAGCTCCAGTAAGAAGGTA |
| | SRP19 | |
| | UP-TGCGGCTCCTGGGTTGTTG | RP-GCCCCTTCCTTTCTGAGGAC |
| | UP-TTTTCTCCTGCCTCTTACTGC | RP-ATGACACCCCCCATTCCCTC |
| | UP-CCACTTAAAGCACATATATTTAGT | RP-GTATGGAAAATAGTGAAGAACC |
| | UP-TTCTTAAGTCCTGTTTTTCTTTTG | RP-TTTAGAACCTTTTTTGTGTTGTG |
| | UP-CTCAGATTATACACTAAGCCTAAC | RP-CATGTCTCTTACAGTAGTACCA |
| | DP2.5 | |
| | UP-AGGTCCAAGGGTAGCCAAGG* | RP-TAAAAATGGATAAACTACAATTAAAAG |
| | UP-AAATACAGAATCATGTCTTGAAGT | RP-ACACCTAAAGATGACAATTTGAG |
| | UP-TAACTTAGATAGCAGTAATTTCCC* | RP-ACAATAAACTGGAGTACACAAGG |
| | UP-ATAGGTCATTGCTTCTTGCTGAT* | RP-TGAATTTTAATGGATTACCTAGGT |
| | UP-CTTTTTTTGCTTTTACTGATTAACG | RP-TGTAATTCATTTTATTCCTAATACCTC |
| | UP-GGTAGCCATAGTATGATTATTTCT | RP-CTACCTATTTTTATACCCACAAAC |

TABLE III-continued

Sequences of Primers Used for SSCP Analyses

| Exon | Primer 1 | Primer 2 |
|---|---|---|
| | UP-AAGAAAGCCTACACCATTTTTGC | RP-GATCATTCTTAGAACCATCTTGC |
| | UP-ACCTATAGTCTAAATTATACCATC | RP-GTCATGGCATTACTGACCAG |
| | UP-AGTCGTAATTTTGTTTCTAAACTC | RP-TGAAGGACTCCGATTTTCACCC* |
| | UP-TCATTCACTCACAGCCTGATGAC* | RP-GCTTTGAAACATGCACTACGAT |
| | UP-AAACATCATTGCTCTTCAAATAAC | RP-TACCATGATTTAAAAATCCACCAG |
| | UP-GATGATTGTCTTTTTCCTCTTTGC | RP-CTGAGCTATCTTAAGAAATACATG |
| | UP-TTTTAAATGATCCTCTATTCTGTAT | RP-ACAGAGTCAGACCCTCCCTCAAAG |
| | UP-TTTCTATTCTTACTGCTAGCATT | RP-ATACACAGGTAAGAAATTAGGA |
| | UP-TAGATGACCCATATTCTCTTTC | RP-CAATTAGGTCTTTTTGAGAGTA |
| 3-A | UP-GTTACTGCATACACATTGTGAC | RP-GCTTTTTGTTTCGTAACATGAAG* |
| -B | UP-AGTACAAGGATGCCAATATTATG* | RP-ACTTCTATCTTTTTCAGAACGAG* |
| -C | UP-ATTTGAATACTACAGTGTTACCC* | RP-CTTGTATTCTAATTTGGCATAAGG* |
| -D | UP-CTGCCCATACACATTCAAACAC* | RP-TGTTTGCGTCTTGCCCATCTT* |
| -E | UP-AGTCTTAAATATTCAGATGAGCAG* | RP-GTTTCTCTTCATTATATTTTATGCTA* |
| -F | UP-AAGCCTACCAATTATAGTGAACG* | RP-AGCTGATGACAAAGATGATAATC* |
| -G | UP-AAGAAACAATACAGACTTATTGTG* | RP-ATGAGTGGGGTCTCCTGAAC* |
| -H | UPATCTCCCTCCAAAAGTGGTGC* | RP-TCCATCTGGAGTACTTTCTGTG* |
| -I | UP-AGTAAATGCTGCAGTTCAGAGG* | RP-CCGTGGCATATCATCCCCC* |
| -J | UP-CCCAGACTGCTTCAAAATTACC* | RP-GAGCCTCATCTGTACTTCTGC* |
| -K | UP-CCCTCCAAATGAGTTAGCTGC* | RP-TTGTGGTATAGGTTTTACTGGTG* |
| -L | UP-ACCCAACAAAAATCAGTTAGATG* | RP-GTGGCTGGTAACTTTAGCCTC* |
| -N | UP-ATGATGTTGACCTTTCCAGGG* | RP-ATTGTGTAACTTTTCATCAGTTGC* |
| -M | UP-AAAGACATACCAGACAGAGGG* | RP-CTTTTTTGGCATTGCGGAGCT* |
| -O | UP-AAGATGACCTGTTGCAGGAATG* | RP-GAATCAGACCAAGCTTGTCTAGAT* |
| -P | UP-CAATAGTAAGTAGTTTACATCAAG* | RP-AAACAGGACTTGTACTGTAGGA* |
| -Q | UP-CAGCCCCTTCAAGCAAACATC* | RP-GAGGACTTATTCCATTTCTACC* |
| -R | UP-CAGTCTCCTGGCCGAAACTC* | RP-GTTGACTGGCGTACTAATACAG* |
| -S | UP-TGGTAATGGAGCCAATAAAAAGG* | RP-TGGGACTTTTCGCCATCCAC* |
| -T | UP-TGTCTCTATCCACACATTCGTC* | RP-ATGTTTTTCATCCTCACTTTTTGC* |
| -U | UP-GGAGAAGAACTGGAAGTTCATC* | RP-TTGAATCTTTAATGTTTGGATTTGC* |
| -V | UP-TCTCCCACAGGTAATACTCCC | RP-GCTACAACTGAATGGGGTACG |
| -W | UP-CAGGACAAAATAATCCTGTCCC | RP-ATTTTCTTACTTTCATTCTTCCTC |

All primers are read in the 5' to 3' direction, the first primer in each pair lies 5' of the exon it amplifies: the second primer lies 3' of the exon it amplifies. Primers that lie within the exon are identified by an asterisk.
UP represents the -21M13 universal primer sequence:
RP represents the M13 reverse primer sequence.

With the exception of exons 1, 3, 4, 9, and 15 of DP2.5 (see below), the primer sequences were located in intron sequences flanking the exons. The 5' primer of exon 1 is complementary to the cDNA sequence, but extends just into the 5' Kozak consensus sequence for the initiator methionine, allowing a survey of the translated sequences. The 5' primer of exon 3 is actually in the 5' coding sequences of this exon, as three separate intronic primers simply would not amplify. The 5' primer of exon 4 just overlaps the 5' end of this exon, and we thus fail to survey the 19 most 5' bases of this exon. For exon 9, two overlapping primer sets were used, such that each had one end within the exon. For exon 15, the large 3' exon of DP2.5, overlapping primer pairs were placed along the length of the exon; each pair amplified a product of 250–400 bases.

EXAMPLE 9

This example demonstrates the use of single stranded conformation polymorphism (SSCP) analysis as described by Orita et al. Proc. Natl. Acad. Sci. U.S.A., Vol. 86, pp. 2766–70 (1989) and Genomics, Vol. 5, pp. 874–879 (1989) as applied to DP1, SRP19 and DP2.5.

SSCP analysis identifies most single- or multiple-base changes in DNA fragments up to 400 bases in length. Sequence alterations are detected as shifts in electrophoretic mobility of single-stranded DNA on nondenaturing acrylamide gels; the two complementary strands of a DNA segment usually resolve as two SSCP conformers of distinct mobilities. However, if the sample is from an individual heterozygous for a base-pair variant within the amplified segment, often three or more bands are seen. In some cases, even the sample from a homozygous individual will show multiple bands. Base-pair-change variants are identified by differences in pattern among the DNAs of the sample set.

Exons of the candidate genes were amplified by PCR from the DNAs of 61 unrelated FAP patients and a control set of 12 normal individuals. The five exons from DP1 revealed no unique conformers in the FAP patients, although common conformers were observed with exons 2 and 3 in some individuals of both affected and control sets, indicating the presence of DNA sequence polymorphisms. Likewise, none of the five exons of SRP19 revealed unique conformers in DNA from FAP patients in the test panel.

Testing of exons 1 through 14 and primer sets A through N of exon 15, of the DP2.5 gene, however, revealed variant conformers specific to FAP patients in exons 7, 8, 10, 11, and 15. These variants were in the unrelated patients 3746, 3460, 3827, 3712, and 3751, respectively. The PCR-SSCP procedure was repeated for each of these exons in the five affected individuals and in an expanded set of 48 normal controls. The variant bands were reproducible in the FAP patients but were not observed in any of the control DNA samples. Additional variant conformers in exons 11 and 15 of the DP2.5 gene were seen; however, each of these was found in both the affected and control DNA sets. The five sets of conformers unique to the FAP patients were sequenced to determine the nucleotide changes responsible for their altered mobilities. The normal conformers from the host individuals were sequenced also. Bands were cut from the dried acrylamide gels, and the DNA was eluted. PCR amplification of these DNAs provided template for sequencing.

The sequences of the unique conformers from exons 7, 8, 10, and 11 of DP2.5 revealed dramatic mutations in the DP2.5 gene. The sequence of the new mutation creating the exon 7 conformer in patient 3746 was shown to contain a deletion of two adjacent nucleotides, at positions 730 and 731 in the cDNA sequence (FIG. 7, SEQ ID NO:1). The normal sequence at this splice junction is CAGGGTCA (intronic sequence underlined), with the intron-exon boundary between the two repetitions of AG. The mutant allele in this patient has the sequence CAGGTCA. Although this change is at the 5' splice site, comparison with known consensus sequences of splice junctions would suggest that a functional splice junction is maintained. If this new splice junction were functional, the mutation would introduce a frameshift that creates a stop codon 15 nucleotides downstream. If the new splice junction were not functional, messenger processing would be significantly altered.

To confirm the 2-base deletion, the PCR product from FAP patient 3746 and a control DNA were electrophoresed on an acrylamide-urea denaturing gel, along with the products of a sequencing reaction. The sample from patient 3746 showed two bands differing in size by 2 nucleotides, with the larger band identical in mobility to the control sample; this result was independent confirmation that patient, 3746 is heterozygous for a 2 bp deletion.

The unique conformer found in exon 8 of patient 3460 was found to carry a C-T transition, at position 904 in the cDNA sequence of DP2.5 (shown in FIG. 7), which replaced the normal sequence of CGA with TGA. This point mutation, when read in frame, results in a stop codon replacing the normal arginine codon. This single-base change had occurred within the context of a CG dimer, a potential hot spot for mutation (Barker et al., 1984).

The conformer unique to FAP patient 3827 in exon 10 was found to contain a deletion of one nucleotide (1367, 1368, or 1369) when compared to the normal sequence found in the other bands on the SSCP gel. This deletion, occurring within a set of three T's, changed the sequence from CTTTCA to CTTCA; this 1 base frameshift creates a downstream stop within 30 bases. The PCR product amplified from this patient's DNA also was electrophoresed on an acrylamide-urea denaturing gel, along with the PCR product from a control DNA and products from a sequencing reaction. The patient's PCR product showed two bands differing by 1 bp in length, with the larger identical in mobility to the PCR product from the normal DNA; this result confirmed the presence of a 1 bp deletion in patient 3827.

Sequence analysis of the variant conformer of exon 11 from patient 3712 revealed the substitution of a T by a G at position changing the normal tyrosine codon to a stop codon.

The pair of conformers observed in exon 15 of the DP2.5 gene for FAP patient 3751 also was sequenced. These conformers were found to carry a nucleotide substitution of C to G at position 5253, the third base of a valine codon. No amino acid change resulted from this substitution, suggesting that this conformer reflects a genetically silent polymorphism.

The observation of distinct inactivating mutations in the DP2.5 gene in four unrelated patients strongly suggested that DP2.5 is the gene involved in FAP. These mutations are summarized in Table IIA.

EXAMPLE 10

This example demonstrates that the mutations identified in the DP2.5 (APC) gene segregate with the FAP phenotype.

Patient 3746, described above as carrying an APC allele with a frameshift mutation, is an affected offspring of two normal parents. Colonoscopy revealed no polyps in either parent nor among the patient's three siblings.

DNA samples from both parents, from the patient's wife, and from their three children were examined. SSCP analysis of DNA from both of the patient's parents displayed the normal pattern of conformers for exon 7, as did DNA from the patients's wife and one of his off-spring. The two other children, however, displayed the same new conformers as their affected father. Testing of the patient and his parents with highly polymorphic VNTR (variable number of tandem repeat) markers showed a 99.98% likelihood that they are his biological parents.

These observations confirmed that this novel conformer, known to reflect a 2 bp deletion mutation in the DP2.5 gene, appeared spontaneously with FAP in this pedigree and was transmitted to two of the children of the affected individual.

EXAMPLE 11

This example demonstrates polymorphisms in the APC gene which appear to be unrelated to disease (FAP).

Sequencing of variant conformers found among controls as well as individuals with APC has revealed the following polymorphisms in the APC gene: first, in exon 11, at position 1458, a substitution of T to C creating an RsaI restriction site but no amino acid change; and second, in exon 15, at positions 5037 and 5271, substitutions of A to G and G to T, respectively, neither resulting in amino acid substitutions. These nucleotide polymorphisms in the APC gene sequence may be useful for diagnostic purposes.

EXAMPLE 12

This example shows the structure of the APC gene.

The structure of the APC gene is schematically shown in FIG. 8, with flanking intron sequences indicated (SEQ ID NO:11–38).

The continuity of the very large (6.5 kb), most 3' exon in DP2.5 was shown in two ways. First, inverse PCR with primers spanning the entire length of this exon revealed no divergence of the cDNA sequence from the genomic sequence. Second, PCR amplification with converging primers placed at intervals along the exon generated products of the same size whether amplified from the originally isolated cDNA, cDNA from various tissues, or genomic template. Two forms of exon 9 were found in DP2.5: one is the complete exon; and the other, labeled exon 9A, is the result of a splice into the interior of the exon that deletes bases 934 to 1236 in the mRNA and removes 101 amino acids from the predicted protein (see FIG. 3, SEQ ID NO:1 and 2).

EXAMPLE 13

This example demonstrates the mapping of the FAP deletions with respect to the APC exons.

Somatic cell hybrids carrying the segregated chromosomes 5 from the 100 kb (HHW1291) and 260 kb (HHW1155) deletion patients were used to determine the distribution of the APC genes exons across the deletions. DNAs from these cell lines were used as template, along with genomic DNA from a normal control, for PCR-based amplification of the APC exons.

PCR analysis of the hybrids from the 260 kb deletion of patient 3214 showed that all but one (exon 1) of the APC exons are removed by this deletion. PCR analysis of the somatic cell hybrid HHW1291, carrying the chromosome 5 homolog with the 100 kb deletion from patient 3824, revealed that exons 1 through 9 are present but exons 10 through 15 are missing. This result placed the deletion breakpoint either between exons 9 and 10 or within exon 10.

EXAMPLE 14

This example demonstrates the expression of alternately spliced APC messenger in normal tissues and in cancer cell lines.

Tissues that express the APC gene were identified by PCR amplification of cDNA made to mRNA with primers located within adjacent APC exons. In addition, PCR primers that flank the alternatively spliced exon 9 were chosen so that the expression pattern of both splice forms could be assessed. All tissue types tested (brain, lung, aorta, spleen, heart, kidney, liver, stomach, placenta, and colonic mucosa) and cultured cell lines (lymphoblasts, HL60, and choriocarcinoma) expressed both splice forms of the APC gene. We note, however, that expression by lymphocytes normally residing in some tissues, including colon, prevents unequivocal assessment of expression. The large mRNA, containing the complete exon 9 rather than only exon 9A, appears to be the more abundant message.

Northern analysis of poly(A)-selected RNA from lymphoblasts revealed a single band of approximately 10 kb, consistent with the size of the sequenced cDNA.

EXAMPLE 15

This example discusses structural features of the APC protein predicted from the sequence.

The cDNA consensus sequence of APC predicts that the longer, more abundant form of the message codes for a 2842 or 2844 amino acid peptide with a mass of 311.8 kd. This predicted APC peptide was compared with the current data bases of protein and DNA sequences using both Intelligenetics and GCG software packages. No genes with a high degree of amino arid sequence similarity were found. Although many short (approximately 20 amino arid) regions of sequence similarity were uncovered, none was sufficiently strong to reveal which, if any, might represent functional homology. Interestingly, multiple similarities to myosins and keratins did appear. The APC gene also was scanned for sequence motifs of known function; although multiple glycosylation, phosphorylation, and myristoylation sites were seen, their significance is uncertain.

Analysis of the APC peptide sequence did identify features important in considering potential protein structure. Hydropathy plots (Kyte and Doolittle, J. Mol. Biol. Vol. 157, pp. 105–132 (1982)) indicate that the APC protein is notably hydrophilic. No hydrophobic domains suggesting a signal peptide or a membrane-spanning domain were found. Analysis of the first 1000 residues indicates that α-helical rods may form (Cohen and Parry, Trends Biochem, Sci. Vol. 77, pp. 245–248 (1986); there is a scarcity of proline residues and, there are a number of regions containing heptad repeats (apolar-X-X-apolar-X-X-X). Interestingly, in exon 9A, the deleted form of exon 9, two heptad repeat regions are reconnected in the proper heptad repeat frame, deleting the intervening peptide region. After the first 1000 residues, the high proline content of the remainder of the peptide suggests a compact rather than a rod-like structure.

The most prominent feature of the second 1000 residues is a 20 amino acid repeat that is iterated seven times with semiregular spacing (Table 4). The intervening sequences between the seven repeat regions contained 114, 116, 151, 205, 107, and 58 amino acids, respectively. Finally, residues 2200–24000 contain a 200 amino acid basic domain.

TABLE IV

Seven Different Versions of the 20-Amino Acid Repeat

| Consensus: | F * V E * T P * C F S R * S S L S S L S |
|---|---|
| 1262: | Y C V E D T P I C F S R C S S L S S L S |
| 1376: | H T V Q E T P L M F S R C T S V S S L D |
| 1492: | F A T E S T P D G F S C S S S L S A L S |
| 1643: | Y C V E G T P I N F S T A T S L S D L T |
| 1848: | T P I E G T P Y C F S R N D S L S S L D |
| 1953: | F A I E N T P V C P S H N S S L S S L S |
| 2013: | R H V E D T P V C F S R N S S L S S L S |

Numbers denote the first amino acid of each repeat. The consensus sequence at the top reflects a majority amino acid at a given position.

---

We claim:

1. A preparation of antibodies which specifically binds to a human APC (adenomatous polyposis coli) protein having an amino acid sequence as shown in SEQ ID NO:1, 2, or 7, and does not specifically bind to other human proteins.

2. A preparation of antibodies which specifically binds to a human APC protein which is the product of a mutant allele found in a tumor, wherein the antibodies do not specifically bind to other human proteins, and wherein the human APC protein is a mutant form of the amino acid sequence shown in SEQ ID NOS:2 and 7, and the mutant allele is a mutant form of the nucleotide sequence shown in SEQ ID NO:1.

3. The preparation of claim 2 wherein the mutant allele contains a mutation selected from the group consisting of mutations at codons 243, 279, 288, 301,331,413,437, 456, 500, 712, and 1338.

4. The preparation of claim 2 wherein the mutant allele contains a premature stop codon.

5. The preparation of claim 2 wherein the mutant allele contains a missense mutation.

6. The preparation of claim 2 wherein the mutant allele contains a frameshift mutation.

7. The preparation of claim 2 wherein the mutant allele contains a splice junction mutation.

8. The preparation of claim 2 wherein the mutant allele contains an insertion mutation.

* * * * *